US012655433B2

(12) United States Patent　　(10) Patent No.: US 12,655,433 B2

Shoshan-Barmatz　　(45) Date of Patent: Jun. 16, 2026

(54) VDAC1 SILENCING MOLECULES AND USE THEREOF

(71) Applicant: NATIONAL INSTITUTE FOR BIOTECHNOLOGY IN THE NEGEV LTD., Beer-Sheva (IL)

(72) Inventor: Varda Shoshan-Barmatz, Omer (IL)

(73) Assignee: NATIONAL INSTITUTE FOR BIOTECHNOLOGY IN THE NEGEV LTD., Beer-Sheva (IL)

( * ) Notice: Subject to any disclaimer, the term of this patent is extended or adjusted under 35 U.S.C. 154(b) by 1136 days.

(21) Appl. No.: 17/289,822

(22) PCT Filed: Oct. 31, 2019

(86) PCT No.: PCT/IL2019/051181

§ 371 (c)(1),
(2) Date: Apr. 29, 2021

(87) PCT Pub. No.: WO2020/089906

PCT Pub. Date: May 7, 2020

(65) Prior Publication Data

US 2021/0395752 A1　　Dec. 23, 2021

Related U.S. Application Data

(60) Provisional application No. 62/867,234, filed on Jun. 27, 2019, provisional application No. 62/754,007, filed on Nov. 1, 2018.

(51) Int. Cl.

| | |
|---|---|
| *C12N 15/113* | (2010.01) |
| *A61K 31/713* | (2006.01) |
| *A61K 45/06* | (2006.01) |
| *A61P 35/00* | (2006.01) |

(52) U.S. Cl.
CPC ........ *C12N 15/1138* (2013.01); *A61K 31/713* (2013.01); *A61K 45/06* (2013.01); *A61P 35/00* (2018.01); *C12N 2310/14* (2013.01); *C12N 2310/321* (2013.01); *C12N 2320/31* (2013.01)

(58) Field of Classification Search
CPC ............ C12N 15/1138; C12N 2310/14; C12N 2310/321; C12N 2320/31; C12N 15/113; A61K 31/713; A61K 45/06; A61K 31/712; A61P 35/00
See application file for complete search history.

(56) References Cited

U.S. PATENT DOCUMENTS

| | | |
|---|---|---|
| 3,687,808 A | 8/1972 | Merigan, Jr. |
| 4,469,863 A | 9/1984 | Ts o |
| 4,476,301 A | 10/1984 | Mbach |
| 5,023,243 A | 6/1991 | Tullis |
| 5,034,506 A | 7/1991 | Summerton |
| 5,166,315 A | 11/1992 | Summerton |
| 5,177,196 A | 1/1993 | Meyer, Jr. |
| 5,185,444 A | 2/1993 | Summerton |
| 5,188,897 A | 2/1993 | Suhadolnik |
| 5,214,134 A | 5/1993 | Weis |
| 5,216,141 A | 6/1993 | Benner |
| 5,235,033 A | 8/1993 | Summerton |
| 5,264,423 A | 11/1993 | Cohen |
| 5,264,562 A | 11/1993 | Matteucci |
| 5,264,564 A | 11/1993 | Matteucci |
| 5,276,019 A | 1/1994 | Cohen |
| 5,278,302 A | 1/1994 | Caruthers |
| 5,286,717 A | 2/1994 | Cohen |
| 5,321,131 A | 6/1994 | Agrawal |
| 5,399,676 A | 3/1995 | Froehler |
| 5,405,938 A | 4/1995 | Summerton |
| 5,405,939 A | 4/1995 | Suhadolnik |
| 5,434,257 A | 7/1995 | Matteucci |
| 5,453,496 A | 9/1995 | Caruthers |
| 5,455,233 A | 10/1995 | Spielvogel |
| 5,464,764 A | 11/1995 | Capecchi |
| 5,466,677 A | 11/1995 | Baxter |
| 5,470,967 A | 11/1995 | Huie |
| 5,476,925 A | 12/1995 | Letsinger |
| 5,487,992 A | 1/1996 | Capecchi |
| 5,489,677 A | 2/1996 | Sanghvi |
| 5,519,126 A | 5/1996 | Hecht |
| 5,536,821 A | 7/1996 | Agrawal |
| 5,539,082 A | 7/1996 | Nielsen |
| 5,541,306 A | 7/1996 | Agrawal |

(Continued)

FOREIGN PATENT DOCUMENTS

| | | |
|---|---|---|
| WO | 2013012806 A2 | 1/2013 |
| WO | 2013035095 A1 | 3/2013 |

(Continued)

OTHER PUBLICATIONS

Fakhr, Elham, F. Zare, and Ladan Teimoori-Toolabi. "Precise and efficient siRNA design: a key point in competent gene silencing." Cancer gene therapy 23.4 (2016): 73-82. (Year: 2016).*

GenBank (Year: 2017).*

GenBank1, Rattus norvegicus voltage-dependent anion channel 1 (Vdac1), mRNA, https://www.ncbi.nlm.nih.gov/nuccore/13786199?sat=46&satkey=70388656, revision Apr. 16, 2017, retrieved Jul. 29, 2024 (Year: 2017).*

Arif, Tasleem, et al. "Silencing VDAC1 expression by siRNA inhibits cancer cell proliferation and tumor growth in vivo." Molecular Therapy-Nucleic Acids 3 (2014). (Year: 2014).*

(Continued)

*Primary Examiner* — Ekaterina Poliakova-Georgantas
*Assistant Examiner* — John Charles Mckillop
(74) *Attorney, Agent, or Firm* — FULLER IP LAW LLC; Rodney J. Fuller; Michael Scher

(57) ABSTRACT

The present invention relates to the field of cancer therapy, specifically to potent RNA inhibitory molecules silencing the expression of Voltage-Dependent Ion Chanel- (VDAC1) and to the use of RNA inhibitory molecules for treating cancer.

3 Claims, 27 Drawing Sheets

Specification includes a Sequence Listing.

(56) References Cited

U.S. PATENT DOCUMENTS

| | | | |
|---|---|---|---|
| 5,541,307 A | 7/1996 | Cook | |
| 5,550,111 A | 8/1996 | Suhadolnik | |
| 5,561,225 A | 10/1996 | Maddry | |
| 5,563,253 A | 10/1996 | Agrawal | |
| 5,571,799 A | 11/1996 | Tkachuk | |
| 5,587,361 A | 12/1996 | Cook | |
| 5,596,086 A | 1/1997 | Matteucci | |
| 5,602,240 A | 2/1997 | De Mesmaeker | |
| 5,608,046 A | 3/1997 | Cook | |
| 5,610,289 A | 3/1997 | Cook | |
| 5,618,704 A | 4/1997 | Sanghvi | |
| 5,623,070 A | 4/1997 | Cook | |
| 5,625,050 A | 4/1997 | Beaton | |
| 5,633,360 A | 5/1997 | Bischofberger | |
| 5,663,312 A | 9/1997 | Chaturvedula | |
| 5,677,437 A | 10/1997 | Teng | |
| 5,677,439 A | 10/1997 | Weis | |
| 5,714,331 A | 2/1998 | Buchardt | |
| 5,719,262 A | 2/1998 | Buchardt | |
| 6,303,374 B1 | 10/2001 | Zhang | |
| 8,093,369 B2 | 1/2012 | Shoshan-Barmatz | |
| 2012/0164730 A1 | 6/2012 | Shoshan-Barmatz | |
| 2012/0322851 A1* | 12/2012 | Hardee | A61K 9/0053 |
| | | | 514/44 R |
| 2017/0051286 A1* | 2/2017 | Smith | C12N 15/113 |
| 2018/0327753 A1* | 11/2018 | Shoshan-Barmatz | |
| | | | C12N 15/1138 |

FOREIGN PATENT DOCUMENTS

| | | | | |
|---|---|---|---|---|
| WO | WO-2017081686 A1 * | 5/2017 | | A61K 31/713 |
| WO | 2020110111 A1 | 6/2020 | | |
| WO | 2020110112 A1 | 6/2020 | | |

OTHER PUBLICATIONS

Pan M, Ni J, He H, Gao S, Duan X. New paradigms on siRNA local application. BMB Rep. Mar. 2015;48(3):147-52. (Year: 2015).*

Abu-Hamad et al., (2006) The expression level of the voltage-dependent anion channel controls life and death of the cell. Proc Natl Acad Sci U S A 103(15): 5787-5792. With correction.

Alfaleh et al., (2017) Targeting mesothelin receptors with drug-loaded bacterial nanocells suppresses human mesothelioma tumour growth in mouse xenograft models. PLoS One 12(10): e0186137; 21 pages.

Alley et al., (2017) Clinical safety and activity of pembrolizumab in patients with malignant pleural mesothelioma (KEYNOTE-028): preliminary results from a non-randomised, open-label, phase 1b trial. Lancet Oncol 18(5): 623-630.

Arif et al., (2014) Silencing VDAC1 Expression by siRNA Inhibits Cancer Cell Proliferation and Tumor Growth In Vivo. Mol Ther Nucleic Acids 3(4): e159; 14 pages.

Arif et al., (2017) VDAC1 is a molecular target in glioblastoma, with its depletion leading to reprogrammed metabolism and reversed oncogenic properties. Neuro Oncol 19(7): 951-964. With corrigendum.

Arif et al., (2018) Mitochondrial VDAC1 Silencing Leads to Metabolic Rewiring and the Reprogramming of Tumour Cells into Advanced Differentiated States. Cancers (Basel) 10(12): 499; 26 pages.

Arif et al., (2019) Metabolic Reprograming Via Silencing of Mitochondrial VDAC1 Expression Encourages Differentiation of Cancer Cells. Mol Ther Nucleic Acids 17: 24-37. With supplemental information.

Brahimi-Horn et al., (2012) Expression of a truncated active form of VDAC1 in lung cancer associates with hypoxic cell survival and correlates with progression to chemotherapy resistance. Cancer Res 72(8): 2140-2150.

Brahimi-Horn et al., (2015) Local mitochondrial-endolysosomal microfusion cleaves voltage-dependent anion channel 1 to promote survival in hypoxia. Mol Cell Biol 35(9): 1491-1505.

Burger et al., (2013) Epidemiology and risk factors of urothelial bladder cancer. Eur Urol 63(2): 234-241.

Das et al., (2012) Assessment of drug delivery and anticancer potentials of nanoparticles-loaded siRNA targeting STAT3 in lung cancer, in vitro and in vivo. Toxicol Lett 225(3): 454-466.

Gilboa et al., (1986) Transfer and expression of cloned genes using retroviral vectors. BioTechniques 4(6): 504-512.

Gurley et al., (2015) Induction of Lung Tumors in Mice with Urethane. Cold Spring Harb Protoc 2015(9): pdb. prot077446; pp. 811-813.

Hassan et al., (2016) Avelumab (MSB0010718C; anti-PD-L1) in patients with advanced unresectable mesothelioma from the JAVELIN solid tumor phase Ib trial: Safety, clinical activity, and PD-L1 expression. Journal of Clinical Oncology 34(15 suppl): 8503-8503.

Hecht (2002) Cigarette smoking and lung cancer: chemical mechanisms and approaches to prevention. Lancet Oncol 3(8): 461-469.

Koren et al., (2010) Downregulation of voltage-dependent anion channel-1 expression by RNA interference prevents cancer cell growth in vivo. Cancer Biol Ther 9(12): 1046-1052.

Maemondo et al., (2010) Gefitinib or chemotherapy for non-small-cell lung cancer with mutated EGFR. N Engl J Med 362(25): 2380-2388.

Pleasance et al., (2013) A small-cell lung cancer genome with complex signatures of tobacco exposure. Nature 463 (7278): 184-190.

Ramazzini (2016) The global health dimensions of asbestos and asbestos-related diseases. J Occup Health 58(2): 220-223.

Reck et al., (2014) Metastatic non-small-cell lung cancer (NSCLC): ESMO Clinical Practice Guidelines for diagnosis, treatment and follow-up. Ann Oncol 25 Suppl 3: iii27-iii39.

Redente et al., (2007) Tumor signaling to the bone marrow changes the phenotype of monocytes and pulmonary macrophages during urethane-induced primary lung tumorigenesis in A/J mice. Am J Pathol 170(2): 693-708.

Shoshan-Barmatz et al., (2015) The mitochondrial voltage-dependent anion channel 1 in tumor cells. Biochim Biophys Acta 1848(10 Pt B): 2547-2575.

Shoshan-Barmatz et al., (2017) Voltage-Dependent Anion Channel 1 As an Emerging Drug Target for Novel Anti-Cancer Therapeutics. Front Oncol 7: 154; 24 pages.

Thun et al., (2008) Lung cancer occurrence in never-smokers: an analysis of 13 cohorts and 22 cancer registry studies. PLoS Med 5(9): e185; 15 pages.

Travis (2012) Update on small cell carcinoma and its differentiation from squamous cell carcinoma and other non-small cell carcinomas. Mod Pathol 25 Suppl 1: S18-S30.

Travis et al., (2011) International Association for the Study of Lung Cancer/American Thoracic Society/European Respiratory Society: international multidisciplinary classification of lung adenocarcinoma: executive summary. Proc Am Thorac Soc 8(5): 381-385.

Travis et al., (2011) International Association for the Study of Lung Cancer/American Thoracic Society/European Respiratory Society International Multidisciplinary Classification of Lung Adenocarcinoma. Journal of Thoracic Oncology 6(2): 244-285.

Vansteenkiste et al., (2013) Early and locally advanced non-small-cell lung cancer (NSCLC): ESMO Clinical Practice Guidelines for diagnosis, treatment and follow-up. Ann Oncol 24 Suppl 6: vi89-vi98.

Yu et al., (2016) MicroRNA-320a inhibits breast cancer metastasis by targeting metadherin. Oncotarget 7(25): 38612-38625.

Zabala et al., (2004) Optimization of the Tet-on system to regulate interleukin 12 expression in the liver for the treatment of hepatic tumors. Cancer Res 64(8): 2799-2804.

Arif et al., (2017) Supplementary Data of VDAC1 is a molecular target in glioblastoma, with its depletion leading to reprogrammed metabolism and reversed oncogenic properties. Neuro Oncol 19(7): 951-964; Retrieved from the Internet: https://www.ncbi.nlm.nih. gov/pmc/articles/PMC5570220/bin/now297_suppl_Supplementary_ Data_FINAL.pdf [retrieved on Jul. 12, 2022]. 25 pages.

Singhal et al., (2003) Gene expression profiling of malignant mesothelioma. Clin Cancer Res 9(8): 3080-3097.

(56)         References Cited

OTHER PUBLICATIONS

Namir et al., (2018) Abstract B24: Met and VDAC1 as target for
breast cancer therapy. Mol Cancer Res 16 (8_Supplement): B24. In:
Proceedings of the AACR Special Conference: Advances in Breast
Cancer Research; Oct. 7-10, 2017; Hollywood, CA. Retrieved from
the Internet: URL: https://aacrjournals.org/mcr/article/16/8_Supplement/
B24/236274/Abstract-B24-Met-and-VDAC1-as-target-for-breast
[retrieved on Jul. 11, 2022]. 5 pages.

* cited by examiner mRNA level, fold of change

CD133  0.2
ALDH1  0.4
KLF4   0.1
SOX2   0.1 si-NT    si-hVDAC1    RU

SEQUENCE LISTING

```
<160> NUMBER OF SEQ ID NOS: 115

<210> SEQ ID NO 1
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 1
gaauagcagc caaguaucag                                              20

<210> SEQ ID NO 2
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 2
ugauacuugg cugcuauuc                                               19

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 3
gaauagcagc caaguaucag tt                                           22

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
ugauacuugg cugcuauuct t                                            21

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: 2'-O-methyl modification
<220> FEATURE:
<221> NAME/KEY: misc_feature
```

```
<222> LOCATION: (14)..(14)
<223> OTHER INFORMATION: 2'-O-methyl modification
<220> FEATURE:
<221> NAME/KEY: misc_feature
<222> LOCATION: (17)..(17)
<223> OTHER INFORMATION: 2'-O-methyl modification

<400> SEQUENCE: 5
gaauagcagc caaguaucag tt                                                        22

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: 2'-O-methyl modification
<220> FEATURE:
<221> NAME/KEY: misc_feature
<222> LOCATION: (13)..(13)
<223> OTHER INFORMATION: 2'-O-methyl modification

<400> SEQUENCE: 6
ugauacuugg cugcuauuct t                                                         21

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: 2'-O-methyl modification
<220> FEATURE:
<221> NAME/KEY: misc_feature
<222> LOCATION: (9)..(9)
<223> OTHER INFORMATION: 2'-O-methyl modification
<220> FEATURE:
<221> NAME/KEY: misc_feature
<222> LOCATION: (15)..(15)
<223> OTHER INFORMATION: 2'-O-methyl modification

<400> SEQUENCE: 7
gaauagcagc caaguaucag tt                                                        22

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: 2'-O-methyl modification
<220> FEATURE:
<221> NAME/KEY: misc_feature
<222> LOCATION: (9)..(9)
<223> OTHER INFORMATION: 2'-O-methyl modification
<220> FEATURE:
<221> NAME/KEY: misc_feature
<222> LOCATION: (17)..(17)
<223> OTHER INFORMATION: 2'-O-methyl modification

<400> SEQUENCE: 8
gaauagcagc caaguaucag tt                                                        22
```

```
<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: 2'-O-methyl modification
<220> FEATURE:
<221> NAME/KEY: misc_feature
<222> LOCATION: (17)..(17)
<223> OTHER INFORMATION: 2'-O-methyl modification

<400> SEQUENCE: 9
gaauagcagc caaguaucag tt                                             22

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: 2'-O-methyl modification
<220> FEATURE:
<221> NAME/KEY: misc_feature
<222> LOCATION: (13)..(13)
<223> OTHER INFORMATION: 2'-O-methyl modification
<220> FEATURE:
<221> NAME/KEY: misc_feature
<222> LOCATION: (17)..(17)
<223> OTHER INFORMATION: 2'-O-methyl modification

<400> SEQUENCE: 10
ugauacuugg cugcuauuct t                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: 2'-O-methyl modification
<220> FEATURE:
<221> NAME/KEY: misc_feature
<222> LOCATION: (8)..(8)
<223> OTHER INFORMATION: 2'-O-methyl modification
<220> FEATURE:
<221> NAME/KEY: misc_feature
<222> LOCATION: (13)..(13)
<223> OTHER INFORMATION: 2'-O-methyl modification

<400> SEQUENCE: 11
ugauacuugg cugcuauuct t                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<220> FEATURE:
```

```
<221> NAME/KEY: misc_feature
<222> LOCATION: (10)..(10)
<220> FEATURE:
<221> NAME/KEY: misc_feature
<222> LOCATION: (18)..(18)

<400> SEQUENCE: 12
ugauacuugg cugcuauuct t                                                           21

<210> SEQ ID NO 13
<211> LENGTH: 19
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: 2'-O-methyl modification
<220> FEATURE:
<221> NAME/KEY: misc_feature
<222> LOCATION: (13)..(13)
<223> OTHER INFORMATION: 2'-O-methyl modification
<220> FEATURE:
<221> NAME/KEY: misc_feature
<222> LOCATION: (17)..(17)
<223> OTHER INFORMATION: 2'-O-methyl modification

<400> SEQUENCE: 13
gcaaacaucc cagaggguau                                                            19

<210> SEQ ID NO 14
<211> LENGTH: 19
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: 2'-O-methyl modification
<220> FEATURE:
<221> NAME/KEY: misc_feature
<222> LOCATION: (11)..(11)
<223> OTHER INFORMATION: 2'-O-methyl modification

<400> SEQUENCE: 14
auaccucugg gauguuugc                                                             19

<210> SEQ ID NO 15
<211> LENGTH: 19
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 2'-O-methyl modification
<220> FEATURE:
<221> NAME/KEY: misc_feature
<222> LOCATION: (8)..(8)
<223> OTHER INFORMATION: 2'-O-methyl modification
<220> FEATURE:
<221> NAME/KEY: misc_feature
<222> LOCATION: (13)..(13)
<223> OTHER INFORMATION: 2'-O-methyl modification
<220> FEATURE:
<221> NAME/KEY: misc_feature
<222> LOCATION: (17)..(17)
<223> OTHER INFORMATION: 2'-O-methyl modification

<400> SEQUENCE: 15
```
acacuaggca ccgagauua                                                  19

<210> SEQ ID NO 16
<211> LENGTH: 19
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification

<400> SEQUENCE: 16
uaaucucggu gccuagugu                                                  19

<210> SEQ ID NO 17
<211> LENGTH: 283
<212> TYPE: PRT
<213> ORGANISM: Homo sapiens

<400> SEQUENCE: 17

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
                20                  25                  30

Thr Lys Ser Glu Asn Gly Leu Glu Phe Thr Ser Ser Gly Ser Ala Asn
            35                  40                  45

Thr Glu Thr Thr Lys Val Thr Gly Ser Leu Glu Thr Lys Tyr Arg Trp
        50                  55                  60

Thr Glu Tyr Gly Leu Thr Phe Thr Glu Lys Trp Asn Thr Asp Asn Thr
65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
            100                 105                 110

Lys Ile Lys Thr Gly Tyr Lys Arg Glu His Ile Asn Leu Gly Cys Asp
        115                 120                 125

Met Asp Phe Asp Ile Ala Gly Pro Ser Ile Arg Gly Ala Leu Val Leu
    130                 135                 140

Gly Tyr Glu Gly Trp Leu Ala Gly Tyr Gln Met Asn Phe Glu Thr Ala
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190

Ser Ile Tyr Gln Lys Val Asn Lys Lys Leu Glu Thr Ala Val Asn Leu
        195                 200                 205

Ala Trp Thr Ala Gly Asn Ser Asn Thr Arg Phe Gly Ile Ala Ala Lys
    210                 215                 220

Tyr Gln Ile Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

-continued

```
Leu Thr Leu Ser Ala Leu Leu Asp Gly Lys Asn Val Asn Ala Gly Gly
        260                 265                 270

His Lys Leu Gly Leu Gly Leu Glu Phe Gln Ala
        275                 280

<210> SEQ ID NO 18
<211> LENGTH: 1838
<212> TYPE: DNA
<213> ORGANISM: Homo sapiens

<400> SEQUENCE: 18
gactcacgca ggtcctcccg cgcgcccgca acacgcccgc aggctcctgt gtctgctgcc      60 gggggcagcgg ggcccggaag gcagaagatg gctgtgccac ccacgtatgc cgatcttggc    120
aaatctgcca gggatgtctt caccaagggc tatggatttg gcttaataaa gcttgatttg     180
aaaacaaaat ctgagaatgg attggaattt acaagctcag gctcagccaa cactagacca     240
ccaaagtgac gggcagtctg gaaaccaagt acagatggac tgagtacggc ctgacgttta     300
cagagaaatg gaataccgac aatacactag gcaccgagat tactgtggaa gatcagcttg     360
cacgtggact gaagctgacc ttcgattcat ccttctcacc taacactggg aaaaaaaatg     420
ctaaaatcaa gacagggtac aagcgggagc acattaacct gggctgcgac atggatttcg     480
acattgctgg gccttccatc cggggtgctc tggtgctagg ttacgagggc tggctggccg     540
gctaccagat gaattttgag actgcaaaat cccgagtgac ccagagcaac tttgcagttg     600
gctacaagac tgatgaattc cagcttcaca ctaatgtgaa tgacgggaca gagtttggcg     660
gctccattta ccagaaagtg aacaagaagt tggagaccgc tgtcaatctt gcctggacag     720
caggaaacag taacacgcgc ttcggaatag cagccaagta tcagattgac cctgacgcct     780
gcttctcggc taaagtgaac aactccagcc tgataggttt aggatacact cagactctaa     840
agccaggtat taaactgaca ctgtcagctc ttctggatgg caagaacgtc aatgctggtg     900
gccacaagct tggtctagga ctggaatttc aagcataaat gaatactgta caattgttta     960
attttaaact attttgcagc atagctacct tcagaattta gtgtatcttt taatgttgta    1020
tgtctgggat gcaagtattg ctaaatatgt tagccctcca ggttaaagtt gattcagctt    1080
taagatgtta cccttccaga ggtacagaag aaacctattt ccaaaaaagg tcctttcagt    1140
ggtagactcg gggagaactt ggtggcccct ttgagatgcc aggtttcttt tttatctaga    1200
aatggctgca agtggaagcg gataatatgt aggcactttg taaattcata ttgagtaaat    1260
gaatgaaatt gtgatttcct gagaatcgaa ccttggttcc ctaaccctaa ttgatgagag    1320
gctcgctgct tgatggtgtg tacaaactca cctgaatggg acttttttag acagatcttc    1380
atgacctgtt cccaccccag ttcatcatca tctcttttac accaaaaggt ctgcaggtg     1440 tggtaactgt ttcttttgtg ccattttggg gtggagaagg tggatgtgat gaagccaata    1500
attcaggact tattccttct tgtgttgtgt tttttttttgg cccttgcacc agagtatgaa    1560
atagcttcca ggagctccag ctataagctt ggaagtgtct gtgtgattgt aatcacatgg    1620
tgacaacact cagaatctaa attggacttc tgttgtattc tcaccactca atttgttttt    1680
tagcagttta atgggtacat tttagagtct tccattttgt tggaattaga tcctcccctt    1740
caaatgctgt aattaacaac acttaaaaaa cttgaataaa atattgaaac ctcatccttc    1800
ttctgttgtc tttattaata aaatataaat aaacaggg                           1838

<210> SEQ ID NO 19
<211> LENGTH: 19
```

```
<212> TYPE: RNA
<213> ORGANISM: Artificial Sequence
<220> FEATURE:
<223> OTHER INFORMATION: Synthetic oligonucleotide

<400> SEQUENCE: 19
acacuaggca ccgagauua                                             19

<210> SEQ ID NO 20
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 20
uaaucucggu gccuagugu                                             19

<210> SEQ ID NO 21
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 21
cuugauuuga aaacaaaauc u                                          21

<210> SEQ ID NO 22
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 22
auuuuguuuu caaaucaagc u                                          21

<210> SEQ ID NO 23
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 23
gaauggauug gaauuuacaa g                                          21

<210> SEQ ID NO 24
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 24
uguaaauucc aauccauucu c                                          21

<210> SEQ ID NO 25
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 25
```

```
cguuuacaga gaaauggaau a                                            21

<210> SEQ ID NO 26
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 26
uuccauuucu cguaaacgu c                                             21

<210> SEQ ID NO 27
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 27
caaaaucuga gaauggauug g                                            21

<210> SEQ ID NO 28
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 28
aauccauucu cagauuuugu u                                            21

<210> SEQ ID NO 29
<211> LENGTH: 2108
<212> TYPE: DNA
<213> ORGANISM: Mus musculus

<400> SEQUENCE: 29
gacccagctt cctccgccga gaggacgaac tccaggcacg gccatgccct ggatccccca      60 gccctacac gccctagccg gcccacgccc ggagtaggtg gcgccgggtc cctcccgcgc     120
atgccagtgt cttcccgggc ggaacgggct gccctgagtg gacttaggcc gcaggaacag     180
ggacctgggc ctggactgag agcgagaccc catagggagc catacgcttg gcctccttgg     240
cctcggggac ggagtccgtg ttctgtgtcg ccaaatgcaa ctgtgcattc tggaaactgt     300
tttcagggcc tgacatcaga ttggaggccc gcaactctac acggtttgtc caaggtcaca     360
ctgaacatgg ccgtgcctcc cacatacgcc gatcttggca agtccgccag ggatgtcttc     420
accaagggct acggctttgg cttaataaaa cttgatttga aaacgaagtc agagaatgga     480
ttggaattta ccagctcagg ctctgccaac acggaaacca ccaaagtgaa cggcagcctg     540
gaaaccaagt acagatggac tgagtatggg ctgacgttta cagagaagtg gaacacagac     600
aacaccctgg gcactgagat cactgtggaa gaccagcttg ctcgtggact gaagctcacc     660
tttgattcgt cattctcgcc gaacactggg aaaaaaaatg ctaaaatcaa gacagggtac     720
aagagggagc acatcaacct cggctgtgac gtggactttg acatcgctgg gccctcgatc     780
cggggcgctc tggtgcttgg ctatgagggt tggctggctg gctaccagat gaattttgag     840
acctcgaagt cccgagtgac ccagagcaac ttcgcagttg gctataagac ggatgaattc     900
cagcttcata ctaatgtgaa tgacgggaca gagtttggtg gctccattta ccagaaggtg     960
aacaagaagt tggagactgc tgtcaatctc gcctggactg caggaaacag taacactcgc    1020
```

```
ttcggaatag cagccaagta tcaggtcgac cctgatgcct gcttttcggc caaagtgaac     1080
aactctagcc tgattggctt agggtacact cagaccctaa aaccaggtat caaactgacg     1140
ttgtcagccc tgctcgatgg caagaacgtc aatgcgggtg ccacaagct tggcctagga      1200 ctggaatttc aagcataaat gaatattgta caatcgttta attttaaact attttgcagc     1260
atagctacct tcagaattta gtgtacctttt taatgttgta tgttggggat gcgagagttg    1320
ataaatacca cgttagacct ccaggctaag gatgactcgg ctttaaggtg tttaccattt     1380
cagaggtaca gcagaaaccc cattccagaa agggtccttt ttagctgtag gcgtgggttg     1440
gggaggagcc cctgtagaga tgccaggcta caagtggaaa gctgggaaca tgtgggtcct     1500
ttgtaaatct gtatccagtc cccagatgaa attgtgactt cccgagcatc gaaccctggt     1560
gtccagatcc tatctgctcg gaagcatgta cacacctgcg tgaaagggat gttttttagac   1620 tgatcctcac accctgttcc catcgtgccc tgttcccatc ctagcccatc acttaacctg     1680
ttttacacca aaagtagtct ttagggtgtg gttagctatt tcttttgtgc cattttaggg     1740
tggagagggt gggcgtgatg gagccagtca ttcaggactt aattcttcct tgtgttgtgg     1800
tgtggttttc tttcttcttc ttctttttttt tttttaattc cttctttcgc cattgcacca    1860
gagtatgaaa tagcttccgg gttctccggc tctgagctgg gcggtgattg tggtcacacc     1920
ctgacaacac tagggatctc aactgactcc tcttgtagcc tcaccactat tttttagcag     1980
tttaatgggt acattataga gtcttccatt ttgtgtggaa ttagctcctc cccttcaaat     2040
gctgtaatta acatcactta aaataaaact tgaataaaat actgaaacct caaaaaaaaa     2100
aaaaaaaa                                                              2108

<210> SEQ ID NO 30
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 30
cuauggauuu ggcuuaauaa a                                                21

<210> SEQ ID NO 31
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 31
uauuaagcca aauccauagc c                                                21

<210> SEQ ID NO 32
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 32
gcuugauuug aaaacaaaau c                                                21

<210> SEQ ID NO 33
<211> LENGTH: 21
<212> TYPE: RNA
```

-continued

```
<213> ORGANISM: Artificial Sequence
<220> FEATURE:
<223> OTHER INFORMATION: Synthetic oligonucleotide

<400> SEQUENCE: 33
uuuuguuuuc aaaucaagcu u                                          21

<210> SEQ ID NO 34
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 34
cugagaaugg auuggaauuu a                                          21

<210> SEQ ID NO 35
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 35
aauuccaauc cauucucaga u                                          21

<210> SEQ ID NO 36
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 36
cagagaaaug gaauaccgac a                                          21

<210> SEQ ID NO 37
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 37
ucgguauucc auuucucugu a                                          21

<210> SEQ ID NO 38
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 38
ccuaacacug ggaaaaaaaa u                                          21

<210> SEQ ID NO 39
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 39
uuuuuuuccc aguguuaggu g                                          21
```

```
<210> SEQ ID NO 40
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 40
ggaaaaaaaa ugcuaaaauc a                                                21

<210> SEQ ID NO 41
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 41
auuuuagcau uuuuuuuccc a                                                21

<210> SEQ ID NO 42
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 42
gcuacaagac ugaugaauuc c                                                21

<210> SEQ ID NO 43
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 43
aauucaucag ucuuguagcc a                                                21

<210> SEQ ID NO 44
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 44
ccauuuacca gaaagugaac a                                                21

<210> SEQ ID NO 45
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 45
uucacuuucu gguaaaugga g                                                21

<210> SEQ ID NO 46
<211> LENGTH: 21
<212> TYPE: RNA
<213> ORGANISM: Artificial Sequence
<220> FEATURE:
```

-continued

<223> OTHER INFORMATION: Synthetic oligonucleotide

<400> SEQUENCE: 46
cagaaaguga acaagaaguu g                                              21

<210> SEQ ID NO 47
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 47
acuucuuguu cacuuucugg u                                              21

<210> SEQ ID NO 48
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 48
gauacacuca gacucuaaag c                                              21

<210> SEQ ID NO 49
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 49
uuuagagucu gaguguaucc u                                              21

<210> SEQ ID NO 50
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 50
cucuaaagcc agguauuaaa c                                              21

<210> SEQ ID NO 51
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 51
uuaauaccug gcuuuagagu c                                              21

<210> SEQ ID NO 52
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 52
cagagaaugg auuggaauuu a                                              21

-continued

```
<210> SEQ ID NO 53
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 53
aauuccaauc cauucucuga c                                              21

<210> SEQ ID NO 54
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 54
gaauuccagc uucauacuaa u                                              21

<210> SEQ ID NO 55
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 55
uaguaugaag cuggaauuca u                                              21

<210> SEQ ID NO 56
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 56
gcuucauacu aaugugaaug a                                              21

<210> SEQ ID NO 57
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 57
auucacauua guaugaagcu g                                              21

<210> SEQ ID NO 58
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 58
cuggaauuuc aagcauaaau g                                              21

<210> SEQ ID NO 59
<211> LENGTH: 21
<212> TYPE: RNA
<213> ORGANISM: Artificial Sequence
<220> FEATURE:
<223> OTHER INFORMATION: Synthetic oligonucleotide
```

-continued

```
<400> SEQUENCE: 59
uuuaugcuug aaauuccagu c                                          21

<210> SEQ ID NO 60
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 60
aagugaacaa cucuagccug a                                          21

<210> SEQ ID NO 61
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 61
ucaggcuaga guuguucacu u                                          21

<210> SEQ ID NO 62
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 62
aacggcagcc uggaaaccaa g                                          21

<210> SEQ ID NO 63
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 63
cuugguuucc aggcugccgu u                                          21

<210> SEQ ID NO 64
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 64
aacacucgcu ucggaauagc a                                          21

<210> SEQ ID NO 65
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 65
ugcuauuccg aagcgagugu u                                          21

<210> SEQ ID NO 66
<211> LENGTH: 21
```

```
<212> TYPE: RNA
<213> ORGANISM: Artificial Sequence
<220> FEATURE:
<223> OTHER INFORMATION: Synthetic oligonucleotide

<400> SEQUENCE: 66
aauggauugg aauuuaccag c                                         21

<210> SEQ ID NO 67
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 67
gcugguaaau uccaauccau u                                         21

<210> SEQ ID NO 68
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 68
aacuucgcag uuggcuauaa g                                         21

<210> SEQ ID NO 69
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 69
cuuauagcca acugcgaagu u                                         21

<210> SEQ ID NO 70
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 70
aagccaggua uuaaacugac a                                         21

<210> SEQ ID NO 71
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 71
ugucaguuua auaccuggcu u                                         21

<210> SEQ ID NO 72
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 72
```

-continued aagcugaccu ucgauucauc c                                          21

<210> SEQ ID NO 73
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 73
ggaugaaucg aaggucagcu u                                          21

<210> SEQ ID NO 74
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 74
aaacaguaac acgcgcuucg g                                          21

<210> SEQ ID NO 75
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 75
ccgaagcgcg uguuacuguu u                                          21

<210> SEQ ID NO 76
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 76
cggaauagca gccaaguuu                                             19

<210> SEQ ID NO 77
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 77
aaacuuggcu gcuauuccg                                             19

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
actcttccag ccttccttcc                                            20

<210> SEQ ID NO 79
<211> LENGTH: 20
<212> TYPE: DNA
<213> ORGANISM: Artificial Sequence

```
<220> FEATURE:
<223> OTHER INFORMATION: Primer

<400> SEQUENCE: 79
tgttggcgta caggtctttg                                              20

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
aatgacggga cagagtttgg                                              20

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
agcgcgtgtt actgtttcct                                              20

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
ggccatcttt tctgttgggg                                              20

<210> SEQ ID NO 83
<211> LENGTH: 19
<212> TYPE: DNA
<213> ORGANISM: Artificial Sequence
<220> FEATURE:
<223> OTHER INFORMATION: Primer

<400> SEQUENCE: 83
tcagcattga attccgccg                                               19

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
tggaaggact catgaccaca                                              20

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
atgatgttct ggagagcccc                                              20
```

<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
gcaggtggtt gagagtgctt                                                          20

<210> SEQ ID NO 87
<211> LENGTH: 20
<212> TYPE: DNA
<213> ORGANISM: Artificial Sequence
<220> FEATURE:
<223> OTHER INFORMATION: Primer

<400> SEQUENCE: 87
gcacccgcct aagattcttc                                                          20

<210> SEQ ID NO 88
<211> LENGTH: 21
<212> TYPE: DNA
<213> ORGANISM: Artificial Sequence
<220> FEATURE:
<223> OTHER INFORMATION: Primer

<400> SEQUENCE: 88
aggaacaggt atcttggctc t                                                        21

<210> SEQ ID NO 89
<211> LENGTH: 20
<212> TYPE: DNA
<213> ORGANISM: Artificial Sequence
<220> FEATURE:
<223> OTHER INFORMATION: Primer

<400> SEQUENCE: 89
ggggtgtaga ttggtgggaa                                                          20

<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90
tcagtctacg ccgcacttac                                                          20

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
gacatctcag cagtcccaca                                                          20

<210> SEQ ID NO 92
<211> LENGTH: 20
<212> TYPE: DNA
<213> ORGANISM: Artificial Sequence
<220> FEATURE:
<223> OTHER INFORMATION: Primer -continued

<400> SEQUENCE: 92
gtctcagtcc agcacgtttg                                                                   20

<210> SEQ ID NO 93
<211> LENGTH: 20
<212> TYPE: DNA
<213> ORGANISM: Artificial Sequence
<220> FEATURE:
<223> OTHER INFORMATION: Primer

<400> SEQUENCE: 93
gaaacgccgg gaatactgtg                                                                   20

<210> SEQ ID NO 94
<211> LENGTH: 18
<212> TYPE: DNA
<213> ORGANISM: Artificial Sequence
<220> FEATURE:
<223> OTHER INFORMATION: Primer

<400> SEQUENCE: 94
tgccccgaat aaccgctg                                                                     18

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
cgttgaactc ctcggtctct                                                                   20

<210> SEQ ID NO 96
<211> LENGTH: 21
<212> TYPE: DNA
<213> ORGANISM: Artificial Sequence
<220> FEATURE:
<223> OTHER INFORMATION: Primer

<400> SEQUENCE: 96
ccatgcaggt tgacaccgtt g                                                                 21

<210> SEQ ID NO 97
<211> LENGTH: 21
<212> TYPE: DNA
<213> ORGANISM: Artificial Sequence
<220> FEATURE:
<223> OTHER INFORMATION: Primer

<400> SEQUENCE: 97
tcggcagact gattcaaata a                                                                 21

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
aatcttggca gaggcagaaa                                                                   20

<210> SEQ ID NO 99

-continued

```
<211> LENGTH: 20
<212> TYPE: DNA
<213> ORGANISM: Artificial Sequence
<220> FEATURE:
<223> OTHER INFORMATION: Primer

<400> SEQUENCE: 99
tttggagcta ttcccattgc                                              20

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
acagtggcat ctgtgagctg                                              20

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
cccacgtccg tagaaaggta                                              20

<210> SEQ ID NO 102
<211> LENGTH: 21
<212> TYPE: DNA
<213> ORGANISM: Artificial Sequence
<220> FEATURE:
<223> OTHER INFORMATION: Primer

<400> SEQUENCE: 102
gtctacccgc cctatctcaa c                                            21

<210> SEQ ID NO 103
<211> LENGTH: 21
<212> TYPE: DNA
<213> ORGANISM: Artificial Sequence
<220> FEATURE:
<223> OTHER INFORMATION: Primer

<400> SEQUENCE: 103
accataatga cagcctgatg c                                            21

<210> SEQ ID NO 104
<211> LENGTH: 20
<212> TYPE: DNA
<213> ORGANISM: Artificial Sequence
<220> FEATURE:
<223> OTHER INFORMATION: Primer

<400> SEQUENCE: 104
tggagatctt cgacatgctg                                              20

<210> SEQ ID NO 105
<211> LENGTH: 20
<212> TYPE: DNA
<213> ORGANISM: Artificial Sequence
<220> FEATURE:
<223> OTHER INFORMATION: Primer

<400> SEQUENCE: 105
```

-continued tccagagact tcagggtgct                                                  20

<210> SEQ ID NO 106
<211> LENGTH: 19
<212> TYPE: DNA
<213> ORGANISM: Artificial Sequence
<220> FEATURE:
<223> OTHER INFORMATION: Primer

<400> SEQUENCE: 106
cctgcagtca acagccagt                                                   19

<210> SEQ ID NO 107
<211> LENGTH: 19
<212> TYPE: DNA
<213> ORGANISM: Artificial Sequence
<220> FEATURE:
<223> OTHER INFORMATION: Primer

<400> SEQUENCE: 107
ttttccttgc cacattgga                                                   19

<210> SEQ ID NO 108
<211> LENGTH: 20
<212> TYPE: DNA
<213> ORGANISM: Artificial Sequence
<220> FEATURE:
<223> OTHER INFORMATION: Primer

<400> SEQUENCE: 108
gttggtggaa atgagctggt                                                  20

<210> SEQ ID NO 109
<211> LENGTH: 20
<212> TYPE: DNA
<213> ORGANISM: Artificial Sequence
<220> FEATURE:
<223> OTHER INFORMATION: Primer

<400> SEQUENCE: 109
aggctctgca aaagcattgt                                                  20

<210> SEQ ID NO 110
<211> LENGTH: 20
<212> TYPE: DNA
<213> ORGANISM: Artificial Sequence
<220> FEATURE:
<223> OTHER INFORMATION: Primer

<400> SEQUENCE: 110
tgggcttgtc ataacaggat                                                  20

<210> SEQ ID NO 111
<211> LENGTH: 20
<212> TYPE: DNA
<213> ORGANISM: Artificial Sequence
<220> FEATURE:
<223> OTHER INFORMATION: Primer

<400> SEQUENCE: 111
ttgcggtaaa actggctaag                                                  20

<210> SEQ ID NO 112
<211> LENGTH: 20
<212> TYPE: DNA

-continued

```
<213> ORGANISM: Artificial Sequence
<220> FEATURE:
<223> OTHER INFORMATION: Primer

<400> SEQUENCE: 112
ccaaagtcct ggaggttgaa                                        20

<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
taactccagg ccatcacaca                                        20

<210> SEQ ID NO 114
<211> LENGTH: 20
<212> TYPE: DNA
<213> ORGANISM: Artificial Sequence
<220> FEATURE:
<223> OTHER INFORMATION: Primer

<400> SEQUENCE: 114
ctggccgtaa actgctttgt                                        20

<210> SEQ ID NO 115
<211> LENGTH: 20
<212> TYPE: DNA
<213> ORGANISM: Artificial Sequence
<220> FEATURE:
<223> OTHER INFORMATION: Primer

<400> SEQUENCE: 115
tcccaagttt tgagccattc                                        20
```

VDAC1 SILENCING MOLECULES AND USE THEREOF

FIELD OF THE INVENTION

The present invention relates to the field of cancer therapy, specifically to highly potent and improved RNA inhibitory molecules silencing the expression of Voltage-Dependent Ion Chanel-1 (VDAC1) and to the use of RNA inhibitory molecules for treating cancer, including cancer diseases unresponsive to standard modalities of cancer therapy.

BACKGROUND OF THE INVENTION

Voltage-dependent anion channel 1 (VDAC1) is a mitochondrial protein controlling cell energy and metabolic homeostasis (Shoshan-Barmatz et al, Frontiers in Oncology, Front Oncol. 2017 Jul. 31; 7:154). VDAC1 is the sole channel located at the outer mitochondrial membrane (OMM) mediating metabolic cross-talk between mitochondria and the cytosol, transporting metabolites, ions, nucleotides, $Ca^{2+}$ and more, thus regulating mitochondrial activity. VDAC1 also plays a key role in apoptosis, participating in the release of apoptotic factors from mitochondria and via interaction with pro- and anti-apoptotic proteins and is considered as a hub protein interacting with many proteins including anti-apoptotic regulators (Shoshan-Barmatz V et al, Front Oncol. 2017 Jul. 31; 7:154.) VDAC1 is also highly expressed in different tumors (Shoshan-Barmatz V, et al. Biochim Biophys Acta. 2015 October; 1848(10 Pt B):2547-2575), pointing to its significance in high energy-demanding cancer cells.

Several studies have shown that down-regulation of VDAC1 expression led to reduced metabolite exchange between mitochondria and the cytosol and inhibition of the growth of various cancer cell types and tumors (Abu-Hamad, S et al. 2006. Proc. Natl. Acad. Sci. USA 103:5787-5792; Koren, I et al. 2010. Cancer Biol. Ther. 9:1046-1052; Arif, T et al. 2014. Mol. Ther. Nucleic Acids 3, e159).

U.S. Pat. No. 8,093,369 and U.S. Patent Application Publication No. 2012/164730 to an inventor of the present invention discloses VDAC1 silencing molecules, including antisense and RNA interference (RNAi) oligonucleotides useful in regulating cell proliferation. Also disclosed are pharmaceutical compositions comprising same useful in the treatment of diseases associated with aberrant cell proliferation, including cancer diseases.

International (PCT) Application Publication No. WO 2017/081686 to an inventor of the present invention discloses the use of RNA inhibitory molecules, particularly siRNA molecules silencing the expression of VDAC1 for induction of metabolic reprograming leading to reduced tumor growth and the disappearance of cancer stem cell possibly via their differentiation and reduction of tumor angiogenesis. The publication further discloses that tumor treatment with VDAC1-directed siRNA also decreased the levels of tumor-associated macrophage (TAM) markers (F4/80, CD68). It is further disclosed that the treated tumors possess less tumorigenic activity. Among the exemplary siRNAs disclosed therein is a molecule corresponding to SEQ ID NO:1 and SEQ ID NO:3 herein. Related findings are described in Arif T et al. 2017. Neuro Oncol. 19(7), 951-964.

International (PCT) Application Publication No. 2013/012806 discloses methods of protecting a cell, specifically protecting a cell from Alu-RNA-induced degeneration comprising inhibiting an inflammasome, MyD88, IL-18, VDAC1, VDAC2, caspase-8, and/or NF-kB of the cell. According to the '806 publication, administering an inhibitor of MyD88, IL-18, VDAC1, VDAC2, caspase-8, and/or NF-κB can protect a cell, in particular a retinal pigment epithelium cell, a retinal photoreceptor cell or a chordial cell, from Alu-RNA-induced degeneration, and thus can be therapeutically useful in the context of age-related macular degeneration and geographic atrophy. Among the inhibitors of VDAC1 and VDAC2, siRNA molecules targeted to VDAC are disclosed.

Publications of the inventors of the present invention, published after the priority date of the present invention, describe that silencing the expression of VDAC1 by siRNA molecule increased the expression levels of prolactin, estrogen and progesterone receptors (PRLR, ER, PR), and of Her2, CD24 and STATS, associated with prolactin receptor activity in MDA-MB-231 tumor xenografts (Arif T et al., 2018. Cancers (Basel). 8:10(12):499; Arif T et al., 2019. Nucleic Acids doi.org/10.1016/j.omtn.2019.05.003).

Although RNAi mechanism have been used to develop agents for treating cancer, RNAi-based drugs are still scarce.

There is an acknowledged need for, and it would be highly advantageous to have additional RNAi molecules suitable for use in treating cancer.

SUMMARY OF THE INVENTION

The present invention relates to highly potent and/or improved gene silencing agents, particularly to RNA interference (RNAi) molecules and use thereof for treating cancer diseases. More specifically, the present invention provides highly potent modified as well as unmodified VDAC1-silencing oligonucleotides, useful in cancer therapy. The present invention further relates to the use of VDAC1-silencing oligonucleotides for treating mesothelioma, and to combination therapies for treating breast cancer (BC) in a subject characterized by having low or non-detectable levels of the estrogen receptor, progesterone receptor and ERBB2/Her2 receptor (i.e., triple negative (TN) breast cancer (TNBC).

The present invention is based, in part, on the unexpected discovery that a human and mouse cross-reactive VDAC1-silencing oligonucleotide, modified by 2'-O methylation (2'-O Me) at specific nucleotide positions, was significantly more effective in reducing VDAC1 expression than the non-modified sequence, as well as compared to other VDAC1-specific siRNAs having different sequences and/or modified at different positions. The modified cross-reactive human-mouse siRNA was further found to be highly effective in inhibiting the proliferation of several cancer cell types, including mesothelioma, bladder and lung cancer cells, and moreover, in reducing the tumor volume of mesothelioma and lung cancer xenografts.

The present invention is also based, in part, on the unexpected discovery that particular siRNA molecules targeted to VDAC1 are significantly more effective in reducing the expression of VDAC1 in cancer cells, and more importantly in reducing cancer cell proliferation compared to corresponding siRNA molecules also designed to target and silenceVDAC1 expression.

The present invention is further based, in part, on the surprising finding that treatment of triple-negative breast cancer (TNBC) MDA-MB-231 cell line, in culture or in xenograft mouse model, using VDAC1-targeted siRNA, increased the levels of ER, PR, and ERBB2/Her2 receptors, as well as that of prolactin. The induced expression of these receptors in TNBC cells upon reduction of VDAC1 expression may provide the means for a combination therapy of VDAC1 targeted siRNA with hormonal receptors (ER and PR)- and/or Her2-based therapy.

According to a first aspect, the present invention provides a modified VDAC1-silencing oligonucleotide comprising:

a. a first oligonucleotide having the sequence as set forth in SEQ ID NO:1 (GAAUAGCAGCCAAGUAUCAG) derivatized by 2'-O-methyl (2'-O-Me) at position 14 and/or at positions 4 and 17 of SEQ ID NO:1, and/or b. a second oligonucleotide having the nucleic acid sequence as set forth in SEQ ID NO:2 (UGAUAC-UUGGCUGCUAUUC) derivatized by 2'-O-Me at positions 7 and 13 of SEQ ID NO:2, and/or c. an oligonucleotide essentially complementary to the first oligonucleotide or to the second oligonucleotide.

According to certain exemplary embodiments, the first and/or the second oligonucleotide further comprises a 3' overhang of 1-5 nucleotides.

According to certain embodiments, the modified VDAC1-silencing oligonucleotide comprises a first oligonucleotide having the sequence as set forth in SEQ ID NO:3 (GAAUAGCAGCCAAGUAUCAGtt), derivatized by 2'-O-Me at position 14, and/or at positions 4 and 17. In other embodiments, the first oligonucleotide does not include 2'-O-Me at positions 6, 9 and/or 15. According to certain exemplary embodiments, the modified first oligonucleotide is derivatized by 2'-O-Me at positions 4, 14 and 17 and not at positions 6, 9 and 15.

According to certain embodiments, the modified VDAC1-silencing oligonucleotide comprises a second oligonucleotide having the nucleic acid sequence as set forth in SEQ ID NO:4 (UGAUACUUGGCUGCUAUUCtt), derivatized by 2'-O-Me at positions 7 and 13. According to certain exemplary embodiments, the modified VDAC1-silencing oligonucleotide comprises a second oligonucleotide having the nucleic acid sequence as set forth in SEQ ID NO:4 (UGAUACUUGGCUGCUAUUCtt), derivatized by 2'-O-Me at positions 4, 10 and 18.

According to certain embodiment, the modified VDAC1-silencing oligonucleotide is an RNA interference (RNAi) oligonucleotide. For example, the RNAi oligonucleotide may be small interfering RNA (siRNA), short-temporal RNA (stRNA), short-hairpin RNA (shRNA), or microRNA (miRNA).

According to certain embodiment, the modified VDAC1-silencing oligonucleotide is an siRNA. According to certain exemplary embodiment, said siRNA comprises a first oligonucleotide as set forth in SEQ ID NO:5, as follows: GAAUAGCAGCCAAGUAUCAGtt (modifications are marked in bold and underlined) and a second oligonucleotide essentially complementary thereto. According to other exemplary embodiments, said siRNA comprises a first oligonucleotide as set forth in SEQ ID NO:6, as follows: UGAUACUUGGCUGCUAUUCtt and a second oligonucleotide essentially complementary thereto. According to certain currently preferred exemplary embodiments, the siRNA molecule comprises a first oligonucleotide comprising the nucleotides set forth in SEQ ID NO:5 and a second oligonucleotide comprising the nucleotides set forth in SEQ ID NO:6.

According to a further aspect, the present invention provides a VDAC1-silencing oligonucleotide comprising a first oligonucleotide having the sequence set forth in any one of SEQ ID NOs:21, 23, 25, and 27 and a second oligonucleotide essentially complementary thereto.

According to certain embodiments, the second oligonucleotide is at least 70%, at least 80%, at least 90% or at least 95% complementary to the first oligonucleotide. According to some embodiments, the second oligonucleotide is fully complementary to the first oligonucleotide. Each possibility represents a separate embodiment of the present invention.

According to certain embodiments, each of the first and the second oligonucleotide independently is unmodified. According to certain embodiments, each of the first and the second oligonucleotide independently is modified. According to certain exemplary embodiments, the modification is a nucleotide derivatized by 2'-O-methyl (2'-O-Me).

According to certain embodiment, the VDAC1-silencing oligonucleotide is an RNA interference (RNAi) oligonucleotide. According to some embodiments, the RNAi oligonucleotide is selected from the group consisting of small interfering RNA (siRNA), short-temporal RNA (stRNA), short-hairpin RNA (shRNA), or microRNA (miRNA). Each possibility represents a separate embodiment of the present invention.

According to certain exemplary embodiments, the RNAi molecule is an siRNA molecule.

According to certain exemplary embodiments, the VDAC1-silencing oligonucleotide comprises a first oligonucleotide comprising the sequence set forth in SEQ ID NO:21 and a second oligonucleotide comprising the sequence set forth in SEQ ID NO:22. According to certain exemplary embodiments, the VDAC1-silencing oligonucleotide comprises a first oligonucleotide comprising the sequence set forth in SEQ ID NO:23 and a second oligonucleotide comprising the sequence set forth in SEQ ID NO:24. According to certain exemplary embodiments, the VDAC1-silencing oligonucleotide comprises a first oligonucleotide comprising the sequence set forth in SEQ ID NO:25 and a second oligonucleotide comprising the sequence set forth in SEQ ID NO:26. According to certain exemplary embodiments, the VDAC1-silencing oligonucleotide comprises a first oligonucleotide comprising the sequence set forth in SEQ ID NO:27 and a second oligonucleotide comprising the sequence set forth in SEQ ID NO:28.

According to certain embodiments, the VDAC1-silencing oligonucleotide molecules of the present invention, particularly siRNA molecules are encapsulated in a particle suitable for the delivery of the siRNA to the site of action in a subject in need thereof. According to certain embodiments, the siRNA is encapsulated in a Poly(D,L-lactide-co-glycolide) (PLGA) based nanoparticle. According to certain exemplary embodiments, the PLGA-based nanoparticle further comprises polyethyleneimine (PEI), designated herein PEI-PLGA nanoparticle.

The present invention further provides a pharmaceutical composition comprising the unmodified and modified VDAC1-silencing oligonucleotides of the invention, a particle comprising same, and one or more pharmaceutically acceptable diluents, carriers or excipients. According to certain embodiment, the composition is formulated for topical, intratumoral, intravenous or pulmonary administration. Each possibility represents a separate embodiment of the invention. According to some embodiment, the formulation comprises an additional anti-cancer agent, including, for examples, chemotherapeutic agent and an immunotherapeutic agent as are known in the art.

The present invention further discloses use of the unmodified and modified VDAC1-silencing oligonucleotide of the invention and pharmaceutical compositions comprising same for treating cancer diseases.

According to additional aspect, the present invention provides a method for treating cancer in a subject in need thereof, comprising administering to the subject a therapeutically effective amount of a VDAC1-silencing oligonucleotide according to the teachings of the present invention.

According to certain embodiments, the method comprises administering a modified VDAC1-silencing oligonucleotide comprising:

a. a first oligonucleotide having the sequence as set forth in SEQ ID NO:1 (GAAUAGCAGCCAAGUAUCAG) derivatized by 2'-O-methyl (2'-O-Me) at position 14 and/or at positions 4 and 17 of SEQ ID NO: 1, and/or b. a second oligonucleotide having the sequence as set forth in SEQ ID NO:2 (UGAUACUUGGCUGC-UAUUC) derivatized by 2'-O-Me at positions 7 and 13 of SEQ ID NO:2, and/or c. an oligonucleotide complementary to the first or the second oligonucleotide.

According to certain embodiments, the first and/or the second oligonucleotide further comprises a 3' overhang of 1-5 nucleotides.

According to certain embodiments, the modified VDAC1-silencing oligonucleotide comprises a first oligonucleotide having the nucleic acid sequence set forth in SEQ ID NO:3 (GAAUAGCAGCCAAGUAUCAGtt), derivatized by 2'-O-Me at position 14, and/or at positions 4 and 17. In other embodiments, the modified VDAC1-silencing oligonucleotide does not include 2'-O-Me at positions 6, 9 and/or 15. According to certain exemplary embodiments, the modified VDAC1-silencing oligonucleotide is derivatized by 2'-O-Me at positions 4, 14 and 17 and not at positions 6, 9 and 15.

According to certain embodiments, the modified VDAC1-silencing oligonucleotide comprises a second oligonucleotide having the sequence as set forth in SEQ ID NO:4 (UGAUACUUGGCUGCUAUUCTT), derivatized by 2'-O-Me at positions 7 and 13. According to certain exemplary embodiments, the modified VDAC1-silencing oligonucleotide comprises a second oligonucleotide having the nucleic acid sequence as set forth in SEQ ID NO:4 (UGAUAC-UUGGCUGCUAUUCtt), derivatized by 2'-O-Me at positions 4, 10 and 18.

According to certain embodiment, the modified VDAC1-silencing oligonucleotide is an siRNA. According to certain exemplary embodiment, said siRNA comprises a first oligonucleotide as set forth in SEQ ID NO:5, as follows: GAAUAGCAGCCAAGUAUCAGtt (modifications are marked in bold and underlined) and a second oligonucleotide essentially complementary thereto. According to other exemplary embodiments, said siRNA comprises a first oligonucleotide as set forth in SEQ ID NO:6, as follows: UGAUACUUGGCUGCUAUUCtt (modifications are marked in bold and underlined) and a second oligonucleotide essentially complementary thereto. According to certain currently preferred exemplary embodiments, the siRNA molecule comprises a first oligonucleotide comprising the nucleotides set forth in SEQ ID NO:5 and a second oligonucleotide comprising the nucleotides set forth in SEQ ID NO:6.

According to certain embodiments, the VDAC1-silencing siRNA molecule comprises a first oligonucleotide having a sequence selected from the group consisting of SEQ ID NOs:21, 23, 25, and 27 and a second oligonucleotide essentially complementary thereto. Each possibility represents a separate embodiment of the present invention.

According to certain embodiments, the second oligonucleotide is at least 70%, at least 80%, at least 90% or at least 95% complementary to the first oligonucleotide. According to some embodiments, the second oligonucleotide is fully complementary to the first oligonucleotide.

According to certain exemplary embodiments, the VDAC1-silencing oligonucleotide is selected from the group consisting of:

1. an siRNA molecule comprising a first oligonucleotide having the sequence set forth in SEQ ID NO:21 and a second oligonucleotide having the sequence set forth in SEQ ID NO:22;

2. an siRNA molecule comprising a first oligonucleotide having the sequence set forth in SEQ ID NO:23 and a second oligonucleotide having the sequence set forth in SEQ ID NO:24;

3. an siRNA molecule comprising a first oligonucleotide having the sequence set forth in SEQ ID NO:25 and a second oligonucleotide having the sequence set forth in SEQ ID NO:26; and 4. an siRNA molecule comprising a first oligonucleotide having the sequence set forth in SEQ ID NO:27 and a second oligonucleotide having the sequence set forth in SEQ ID NO:28.

Each possibility represents a separate embodiment of the present invention.

According to certain embodiments, each of the first and the second oligonucleotide independently is unmodified. According to certain embodiments, each of the first and the second oligonucleotide independently is modified. According to certain exemplary embodiments, the modification is a nucleotide derivatized by 2'-O-methyl (2'-O-Me).

According to certain embodiments, the unmodified and/or modified VDAC1-silencing oligonucleotide is encapsulated within a particle, particularly nanoparticle. According to certain exemplary embodiments, the VDAC1-silencing oligonucleotide is encapsulated within a PGLA-based nanoparticle, particularly PEI-PGLA nanoparticle.

According to certain embodiments, the VDAC1-silencing oligonucleotide or the particle comprising same is administered within a pharmaceutical composition, further comprising pharmaceutically acceptable diluents, carriers or excipients.

According to certain embodiments, the cancer is characterized by VDAC1 over-expression (manifested by at least one tumor exhibiting VDAC1 over-expression in at least a portion of the tumor cells). In various embodiments, the cancer is selected from the group consisting of lung, bladder, mesothelioma, colon, pancreatic, prostate, thyroid, breast, brain, renal, melanoma, B cell chronic lymphocytic leukemia (CLL), liver cancer and acute myeloid leukemia (AML). Each possibility represents a separate embodiment of the invention. According to certain embodiments, the lung cancer includes small-cell lung cancer and non-small cell lung cancer. According to certain embodiments, the cancer is characterized by a tumor comprising cancer stem cells. According to these embodiments, the tumor may be a solid tumor or a non-solid tumor. According to certain exemplary embodiments, the solid tumor comprising cancer stem cells is selected from the group consisting of brain, breast, prostate, cervical, ovary, pancreas, head and neck, sarcoma, lymphoma, melanoma and colon cancer. Each possibility represents a separate embodiment of the present invention. According to further exemplary embodiments, the non-solid tumor comprising cancer stem cells is blood cancer.

According to some embodiments, the cancer is lung cancer. As exemplified herein, the modified siRNA molecule of the present invention is highly effective in treating both small cell lung cancer and non-small cell lung cancer.

According to some embodiments, the cancer is bladder cancer.

According to some embodiments, the cancer is a breast cancer. According to certain embodiments, the cancer is triple negative breast cancer, characterized by having low or non-detectable levels of the estrogen receptor, progesterone receptor and ERBB2/Her2 receptor.

As described and exemplified herein, the invention unexpectedly discloses that the modified, human-mouse cross reactive siRNA of the invention is highly effective in inhibiting the growth of mesothelioma tumors. The present invention demonstrates for the first time that silencing the expression of VDAC1 in mesothelioma tumors results in inhibition of the tumor growth.

Thus, according to a further aspect, the present invention provides a method for treating mesothelioma in a subject in need thereof, the method comprising administrating to the subject a therapeutically effective amount of a VDAC1-silencing oligonucleotide.

As is further described and exemplified herein, silencing the expression of VDAC1 in TNBC MDA-MB-231 cell line, in culture or in xenograft mouse model, increased the levels of ER, PR, and ERBB2/Her2 receptors, as well as that of prolactin.

Thus, according to yet a further aspect, the present invention provides a method for treating breast cancer in a subject in need thereof, comprising: administering to a subject having low or undetectable expression levels of estrogen receptor (ER), progesterone receptor (PR), and ERBB2/Her2 receptor compared to a control an effective amount of VDAC1-silencing oligonucleotide, and administering to the subject a therapeutically effective amount of at least one anti-cancer drug, thereby treating breast cancer in said subject.

According to certain embodiments, the control to which the expression level of estrogen receptor (ER), progesterone receptor (PR), and ERBB2/Her2 receptor of the subject in need thereof is compared is a pre-determined threshold value. According to certain embodiments, the control is the expression level of estrogen receptor (ER), progesterone receptor (PR), and ERBB2/Her2 receptor in a subject having a breast cancer characterized as positive for ER, PR, and/or ERBB2/Her2 receptor expression.

According to certain embodiments, the effective amount of the VDAC1-silencing oligonucleotide is sufficient to sensitize cancer cells of the subject to at least one anti-cancer drug having specific affinity to at least one of the ER, PR and ERBB2/Her2 receptor.

According to certain embodiments, the effective amount of the VDAC1-silencing oligonucleotide is sufficient to increase the expression level of at least one of the ER, PR and ERBB2/Her2 receptor in at least 1% of the cancer cells. According to certain embodiments, the expression is increased compared to the expression detected in cancer cells of the subject before administering the VDAC1-silencing oligonucleotide. According to certain exemplary embodiments, the expression is increased to define the cancer cell as ER, PR, or ERBB2/Her2 receptor positive.

In some exemplary embodiments, the effective amount of the VDAC1-silencing oligonucleotide reduces the expression level of VDAC1 mRNA or protein by from about 50% to about 100% compared to VDAC1 expression level in corresponding breast cancer cells not treated with said VDAC1-silencing oligonucleotide. According to certain embodiments, the effective amount reduces VDAC1 mRNA or protein expression level by from about 60% to about 90%.

In certain embodiments, the VDAC1-silencing oligonucleotide is administered to the subject prior to administering the at least one anti-cancer drug having specific affinity to at least one of ER, PR and ERBB2/Her2 receptor. According to these embodiments, the method optionally further comprises detecting the expression level of the at least one ER, PR and ERBB2/Her2 receptor in cancer cells of the treated subject. In some embodiments, the at least one drug is administered to the subject when the expression level of the at least one ER, PR and ERBB2/Her2 receptor is increased compared to the expression detected in cancer cells of said subject before administering the VDAC1-silencing oligonucleotide.

In certain embodiments, the VDAC1-silencing oligonucleotide is administered to the subject concurrently (e.g., in one composition or in two separate compositions) to administering the at least one anti-cancer drug having specific affinity to at least one of ER, PR and ERBB2/Her2 receptor. According to some exemplary embodiments, the at least one anti-cancer drug is administered from about 1 day to about 25 days after administering the VDAC1-silencing molecule. According to some exemplary embodiments, the at least one anti-cancer drug is administered from about 5 to about 20 days after administering the VDAC1-silencing molecule In some embodiments, the anti-cancer drug is selected from the group consisting of: a hormone-receptor modulator and a hormone receptor down-regulator, wherein the hormone is selected from the group consisting of estrogen and progesterone; ERBB2/Her2 receptor modulator and ERBB2/Her2 receptor down regulator, including ERBB2/Her2 receptor specific antibodies; an aromatase inhibitor; and any combination thereof. Each possibility represents a separate embodiment of the present invention.

In some embodiments, the anti-cancer drug is selected from the group consisting of: trastuzumab (herceptin), trastuzumab emtansine, ado-trastuzumab emtansine (Kadcyla), neratinib (Nerlynx), pertuzumab (Perjeta), and lapatinib (Tykerb). Each possibility represents a separate embodiment of the present invention.

According to certain embodiments, the VDAC1-silencing oligonucleotide for treating mesothelioma or TNBC comprises at least 15 contiguous nucleotides identical to the gene or mRNA encoding human VDAC1 protein or to a polynucleotide complementary thereto.

According to certain embodiments, the VDAC1-silencing oligonucleotide comprises at least 15 contiguous nucleic acids identical to the gene or mRNA encoding human VDAC1 protein or to a complementary polynucleotide thereof, wherein the human VDAC1 protein comprises an amino acid sequence at least 90% identical to the amino acid sequence set forth in SEQ ID NO:17. According to certain exemplary embodiments, the hVDAC1 protein comprises the amino acid sequence set forth in SEQ ID NO:17.

According to certain embodiments the hVDAC1 protein is encoded by a nucleic acid sequence at least 90% identical to the nucleic acid set forth in SEQ ID NO:18. According to certain exemplary embodiments, hVDAC1 protein is encoded by the nucleic acid sequence set forth in SEQ ID NO:18.

According to certain embodiments, the VDAC1-silencing oligonucleotide is an RNAi molecule selected from the group consisting of small interfering RNA (siRNA), short-temporal RNA (stRNA), short-hairpin RNA (shRNA), or microRNA (miRNA). According to certain exemplary embodiments, the RNAi molecule is siRNA. Each possibility represents a separate embodiment of the present invention.

According to certain embodiments, the VDAC1-silencing siRNA molecule comprises a first oligonucleotide having a sequence selected from the group consisting of SEQ ID NOs:1, 3, 5, 7-9, 15, 19, 21, 23, 25, and 27 and a second oligonucleotide essentially complementary thereto. Each possibility represents a separate embodiment of the present invention.

According to certain embodiments, the second oligonucleotide is at least 70%, at least 80%, at least 90%, at least 95%, or identical to the first oligonucleotide.

Specific VDAC1-silencing siRNA molecules to be used with the methods of the invention are as described herein.

According to certain exemplary embodiments, the method of treating mesothelioma comprises administering to a subject in need thereof a therapeutic effective amount of an siRNA molecule comprising a first oligonucleotide having the sequence set forth in SEQ ID NO:5 and a second oligonucleotide having the sequence set forth in SEQ ID NO:6.

According to certain additional or alternative exemplary embodiments, the method of treating mesothelioma comprises administering to a subject in need thereof a therapeutic effective amount of an siRNA molecule comprising a first oligonucleotide having the sequence set forth in SEQ ID NO:15 and a second oligonucleotide having the sequence set forth in SEQ ID NO:16.

According to certain embodiments, the method further comprises administering to the subject additional drug or therapy for treating mesothelioma.

According to certain embodiments, the VDAC1 silencing agent is administered in an amount and under conditions effective to reduce the expression of VDAC1 by at least 70% in mesothelioma tumor cells of said subject. According to certain exemplary embodiments, the method of treating TNBC comprises administering to a subject in need thereof a therapeutic effective amount of an siRNA molecule comprising a first oligonucleotide having the sequence set forth in SEQ ID NO:15 and a second oligonucleotide having the sequence set forth in SEQ ID NO:16.

According to certain embodiments, the method comprises administering to the subject a construct capable of expressing in cells of said subject a therapeutically effective amount of at least one of the VDAC1-silencing oligonucleotides described herein.

It is to be understood that any combination of each of the aspects and the embodiments disclosed herein is explicitly encompassed within the disclosure of the present invention.

Further embodiments and the full scope of applicability of the present invention will become apparent from the description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1 shows VDAC1 expression in human A549 lung cancer cells and murine CT26 colon carcinoma cells treated with various modified and non-modified VDAC1-specific siRNAs.

FIG. 8 demonstrates that VDAC1 is highly expressed in bladder cancer cell line, and the effect of its silencing.

FIG. 10 shows urethane-induced lung cancer in A/J mice.

FIG. 13 D-C shows quantitative analysis of tumor volumes from PLAG-si-NT and PLAG-si-m/hVDAC1-B treated mice, analyzed from the MRI images 31 (FIG. 13C) and 34 (FIG. 13D) weeks after the urethane treatment.

FIG. 15 demonstrate that si-hVDAC1 inhibits MDA-MB-231 growth of breast cancer tumor in a xenograft mouse model.

FIG. 16 demonstrate that si-hVDAC1 treatment reverses the reprogrammed metabolism of MDA-MB-231-derived tumors.

FIG. 17 demonstrates that si-hVDAC1 treatment markedly reduced expression of cancer stem cell (CSC) markers in MDA-MB-231-derived tumors.

FIG. 18 show that treatment of MDA-MB-231-derived tumors with si-hVDAC1 induced expression of specific proteins, including ERBB2/Her2, estrogen receptor (ER) and progesterone receptor (PR).

DETAILED DESCRIPTION OF THE INVENTION

Figures 1A, 1B:
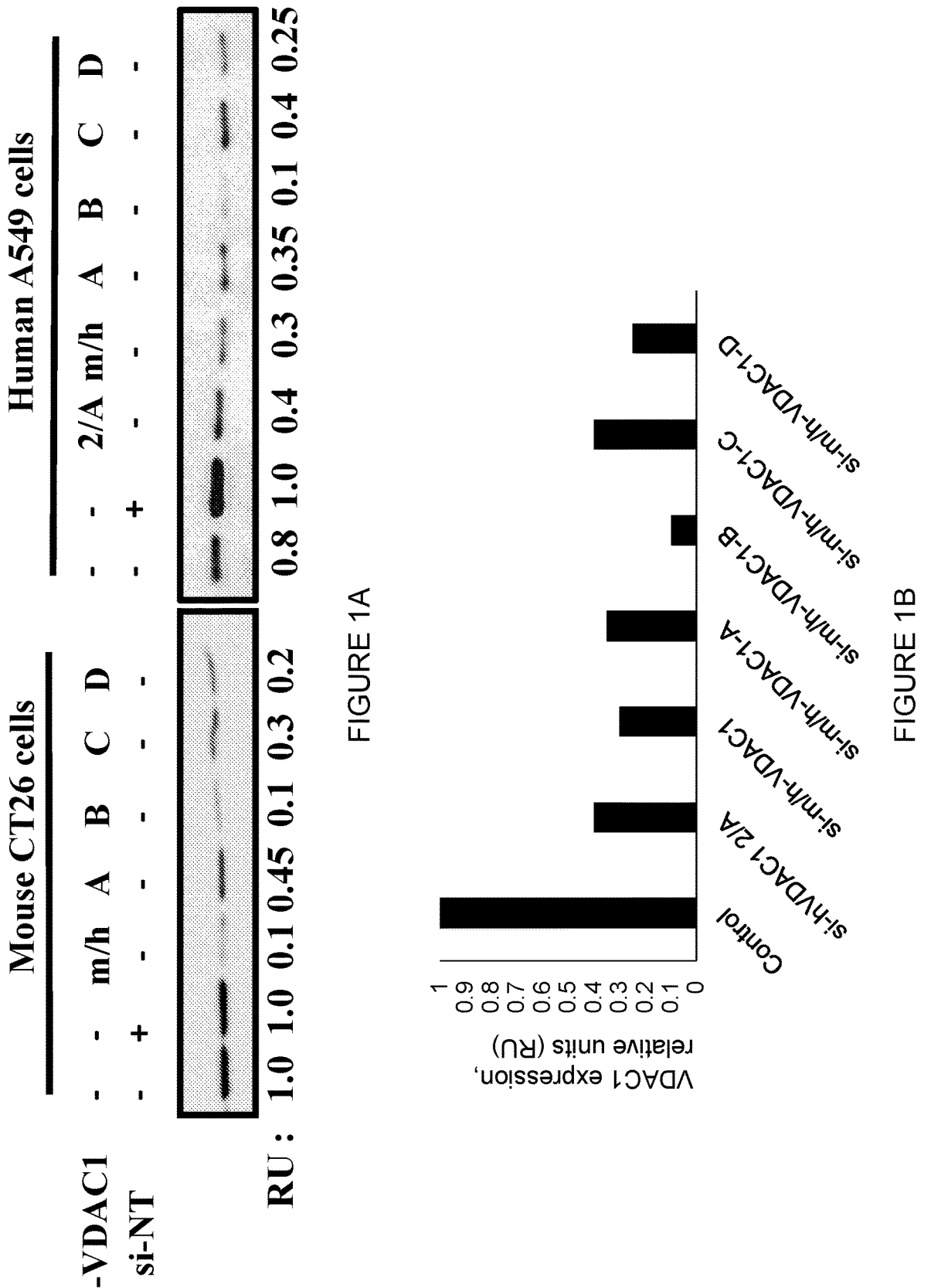
FIG. 1A shows immunoblot of VDAC1 expression in mouse colon carcinoma cell (CT26) and human lung cancer cells (A549) treated with 50 nM of the indicated siRNA molecule.
FIG. 1B demonstrated the quantitative analysis of VDAC1 expression in the human lung cancer cells presented in FIG. 1A. si-m/h VDAC1; 2/A—si-hVDAC1; A—si-m/h VDAC1-A; B—si-m/h VDAC1-B; C—si-m/h VDAC1-C; D—si-m/h VDAC1-D as presented in Table 3 hereinbelow.

The present invention related to the field of cancer therapy, particularly to improved gene silencing agents and use thereof for treating cancer diseases. More specifically, embodiments of the invention provide highly potent modified as well as unmodified VDAC1-silencing oligonucleotides, useful in cancer therapy. The present invention further discloses the use of VDAC1-silencing oligonucleotides for treating mesothelioma, a sever cancer disease with no effective therapy known, and a therapy for treating triple negative breast cancer comprising a combination of VDAC1-silencing oligonucleotides and anti-cancer drug having specific affinity to at least one of the ER, PR and ERBB2/Her2 receptor.

Definitions

As used herein, the term "hVDAC1" refers to the human voltage-depended anion channel isoform 1 (hVDAC1) of a highly conserved family of mitochondrial porin. hVDAC1 refers to a 283 amino acid protein having the amino acids sequence set forth in SEQ ID NO:17. According to certain embodiments of the invention, the VDAC1 protein is encoded by a polynucleotide having the nucleic acid sequence set forth in SEQ ID NO:18.

The terms "VDAC1-silencing oligonucleotide", "VDAC1-silencing oligonucleotide molecule", "VDAC1-silencing molecule" or "oligonucleotide that inhibits or reduces VDAC1 expression" are used herein interchangeably and refer to an oligonucleotide capable of specifically reducing the level or expression of the gene product, i.e. the level of VDAC1 mRNA, below the level that is observed in the absence of the oligonucleotide. In some embodiments, the VDAC1-silencing oligonucleotide promotes reduction of VDAC1 gene expression levels by at least 10%, by at least 50%, by at least 60%, by at least 70%, by at least 80%, by at least 90%, by at least 100%, or any value or range there-between, compared to control. In some embodiments, the VDAC1-silencing oligonucleotide promotes reduction of VDAC1 gene expression levels by 10-100%, 20-100%, 30-100%, 40-100%, 50-100%, 60-100%, or 40-90%, 50-90%, or 60-90% compared to control. Each possibility represents a separate embodiment of the invention.

The terms "oligonucleotide", "oligonucleotide sequence", "nucleic acid sequence", and "polynucleotide" are used herein interchangeably and refer to an oligomer or polymer of ribonucleic acid (ribo-oligonucleotide or ribo-oligo-nucleoside) or deoxyribonucleic acid comprising up to about 100-1,000 nucleic acid residues. In some embodiments, the nucleotide sequences strands are composed of naturally-occurring nucleobases, sugars and covalent inter-sugar link-ages as well as oligonucleotides having non-naturally-oc-curring portions which function similarly. Such modified or substituted oligonucleotides may be, in some embodiments, preferred over native forms because of the valuable charac-teristics including, for example, increased stability in the presence of plasma nucleases and enhanced cellular uptake. In some embodiments, an oligonucleotide is a polymer of RNA or DNA or a hybrid thereof, that is single- or double-stranded, linear or branched, and that optionally contains synthetic, non-natural or altered nucleotide bases. According to certain embodiments of the invention, at least one of the nucleotides s chemically modified by 2'-sugar modification. In a particular embodiment, said 2'-sugar modification is a 2'-O-methyl (2'-O-Me) modification, particularly on the nucleotides uracil and guanine.

The terms "complementary" or "complement thereof" are used herein to refer to the sequences of polynucleotides which is capable of forming Watson and Crick base pairing with another specified polynucleotide throughout the entirety of the complementary region. The terms "substan-tially complementary" and "essentially complementary" are used herein interchangeably. An oligomeric compound need not be 100% complementary to its target nucleic acid to be specifically hybridizable. Moreover, an oligomeric com-pound may hybridize over one or more segments such that intervening or adjacent segments are not involved in the hybridization (e.g., a bulge, a loop structure or a hairpin, structure). A "non-complementary nucleobase" means a nucleobase of an antisense oligonucleotide that is unable to undergo precise base pairing with a nucleobase at a corre-sponding position in a target nucleic acid. In some embodi-ments there are non-complementary positions, also known as "mismatches", between the oligomeric compound and the target nucleic acid, and such non-complementary positions may be tolerated between an oligomeric compound and the target nucleic acid provided that the oligomeric compound remains substantially complementary to the target nucleic acid.

As used herein, the term "reduced" or "reduce" with reference to gene expression (mRNA and/or protein) or with reference to tumor size is by at least 5%, 10%, 30%, 50%, 90%, 100%, or any value or range therebetween, less than control. In some embodiments, reduced or reduce is 5-15%, 10-35%, 30-75%, or 70-100% less than control. Each pos-sibility represents a separate embodiment of the invention.

As used herein, the term "increased" or "increase", par-ticularly in reference to expression of at least one of ER, PR and ERBB2/Her2 receptor is by at least 5%, 10%, 30%, 50%, 90%, 100%, 200%, 500%, 1,000%, or any value or range therebetween, more than control. In some embodi-ments, increased is 5-15%, 10-35%, 30-75%, 70-100%, 90-200%, 150-450%, 400-750%, or 700-1,000% more than control. Each possibility represents a separate embodiment of the invention.

According to a first aspect the present invention is directed to highly potent VDAC1-silencing oligonucle-otides.

According to certain exemplary embodiments, the present invention is directed to modified VDAC1-silencing oligo-nucleotides. The modified VDAC1-silencing oligonucle-otides according to advantageous embodiments of the inven-tion are targeted to (hybridizable with) positions 746-764 of human VDAC1 transcript (SEQ ID NO:18). The modified VDAC1-silencing oligonucleotides advantageously com-prise a sense strand comprising the nucleic acid sequence as set forth in SEQ ID NO:1, as follows: GAAUAGCAGC-CAAGUAUCAG. The modified VDAC1-silencing oligo-nucleotides comprise, according to additional advantageous embodiments, an antisense strand comprising the nucleic acid sequence as set forth in SEQ ID NO:2, as follows: UGAUACUUGGCUGCUAUUC.

The modified VDAC1-silencing oligonucleotides prefer-ably comprise at least one 2'-sugar modification. In a par-ticular embodiment, said 2'-sugar modification is a 2'-O-methyl (2'-O-Me) modification. The VDAC1-silencing oligonucleotides of the invention are advantageously modi-fied (typically by a 2'-O-Me) at least at position 14 of SEQ ID NO:1. Additionally or alternatively, the VDAC1-silenc-ing oligonucleotides of the invention are modified (typically by a 2'-O-Me) at positions 4 and 17 of SEQ ID NO:1. According to an exemplary embodiment, the VDAC1-si-lencing oligonucleotides comprise 2'-O-Me modifications at positions 4, 14 and 17 of SEQ ID NO:1. Additionally or alternatively, the modifications may contain nucleic acid analogs comprising e.g. a 2'-O, 4'-C methylene bridge, such as locked nucleic acids (LNA).

According to further exemplary embodiments, the present invention provides unmodified VDAC1-silencing oligo-nucleotide, unexpectedly found to be significantly more active in silencing VDAC1 expression and cancer cell proliferation compared to VDAC1-silencing molecule designed using similar programs.

According to certain currently exemplary embodiments, the VDAC1-silencing oligonucleotide comprising a first oligonucleotide having the sequence set forth in any one of SEQ ID NOs:21, 23, 25, and 27 and a second oligonucle-otide essentially complementary thereto.

According to certain embodiments, the second oligo-nucleotide is at least 70%, at least 80%, at least 90% or at least 95% complementary to the first oligonucleotide. Each possibility represents a separate embodiment of the present invention. According to some embodiments, the second oligonucleotide is at least 80%, at least 81%, at least 82%, at least 83%, at least 84%, at least 85%, at least 86%, at least 87%, at least 88%, at least 89%, at least 90%, at least 91%, at least 92%, at least 92%, at least 92%, at least 95%, at least 96%, at least 97%, at least 98%, or at least 99% comple-mentary to the first oligonucleotide. Each possibility repre-sents a separate embodiment of the present invention. According to some embodiments, the second oligonucle-otide is 100% complementary to the first oligonucleotide.

According to certain embodiments, each of the first and the second oligonucleotide independently is unmodified. According to certain embodiments, each of the first and the second oligonucleotide independently is modified. Accord-ing to certain exemplary embodiments, the modification is a nucleotide derivatized by 2'-O-methyl (2'-O-Me).

In various embodiments, the VDAC1-silencing oligo-nucleotide is an RNAi oligonucleotide, e.g. a modified double stranded (ds) RNA molecule selected from the group consisting of: small interfering RNA (siRNA), short-temporal RNA (stRNA), short-hairpin RNA (shRNA), and microRNA (miRNA), wherein each possibility represents a separate embodiment of the invention. In a particular embodiment said molecule is a siRNA.

In some embodiments, the modified VDAC1-silencing oligonucleotide is an siRNA comprising a first (sense) RNA strand and a second (antisense) RNA strand, wherein the first and the second RNA strands form an RNA duplex. These siRNA molecules typically further comprise 3' nucleotide overhangs on either or both strands, i.e. terminal portions of the nucleotide sequence that are not base paired between the two strands of the double stranded siRNA molecule. Preferably, the overhang is 1-5 nucleotides in length (e.g. 1-5 deoxythymidines), more preferably two nucleotides in length. In certain embodiments, said siRNA molecules advantageously comprise two 3' deoxythymidine overhangs, thus containing a sense strand having the nucleic acid sequence as set forth in SEQ ID NO:3, as follows: GAAUAGCAGCCAAGUAUCAGTT. Similarly, siRNA molecules according to advantageous embodiments of the invention contain an antisense strand having the nucleic acid sequence as set forth in SEQ ID NO:4, as follows: UGAUACUUGGCUGCUAUUCTT.

Accordingly, provided is a modified VDAC1-silencing oligonucleotide comprising a sense strand having the nucleic acid sequence as set forth in SEQ ID NO:1 and a 3' overhang of 1-5 nucleotides, derivatized by one or more 2'-O-Me modifications, said modifications including 2'-O-Me at position 14, and/or at positions 4 and 17, of SEQ ID NO:1. In a particular embodiment said oligonucleotide comprises two 3' deoxythymidine overhangs. Thus, the invention relates in some embodiments to a modified VDAC1-silencing oligonucleotide comprising a sense strand having the nucleic acid sequence as set forth in SEQ ID NO:3, derivatized by 2'-O-Me at position 14, and/or at positions 4 and 17.

In one advantageous embodiment, said oligonucleotide is preferably modified (derivatized) by a 2'-O-Me at position 14. In another embodiment, said oligonucleotide is further modified (preferably by a 2'-O-Me) at positions 4 and/or 17. In another embodiment said oligonucleotide is modified by 2'-O-Me at positions 4, 14 and 17. In another embodiment, said oligonucleotide does not include a 2'-O-Me at position 9. In another embodiment said oligonucleotide does not include a 2'-O-Me at position 6 and/or 15. In another embodiment said oligonucleotide does not include a 2'-O-Me at positions 6, 9 and 15. In another embodiment said oligonucleotide is modified by 2'-O-Me at positions 4, 14 and 17 and does not include a 2'-O-Me at positions 6, 9 and 15. In another embodiment said modifications consist of 2'-O-Me at positions 4, 14 and 17. All positions are indicated with respect to SEQ ID NO: 1 or 3, and each possibility represents a separate embodiment of the invention.

Additionally, or alternatively, said oligonucleotide is derivatized at positions 7 and/or 13 of its antisense strand. Thus, said oligonucleotide may comprise an antisense strand having the nucleic acid sequence as set forth in SEQ ID NO:2 and a 3' overhang of 1-5 nucleotides, derivatized by 2'-O-Me at positions 7 and 13 of SEQ ID NO: 2. Said oligonucleotide may comprise an antisense strand having the nucleic acid sequence as set forth in SEQ ID NO: 4 (UGAUACUUGGCUGCUAUUCTT), derivatized by 2'-O-Me at positions 7 and 13.

In another embodiment said oligonucleotide is derivatized at positions 4, 10 and 18 of its antisense strand. Thus, said oligonucleotide may comprise an antisense strand having the nucleic acid sequence as set forth in SEQ ID NO:2 and a 3' overhang of 1-5 nucleotides, derivatized by 2'-O-Me at positions 4, 10 and 18 of SEQ ID NO:2. Said oligonucleotide may comprise an antisense strand having the nucleic acid sequence as set forth in SEQ ID NO: 4 (UGAUACUUGGCUGCUAUUCTT), derivatized by 2'-O-Me at positions 4, 10 and 18.

Exemplary siRNA sequences used in the comparative experiments described herein are presented in Table 3 below. A currently preferred exemplary siRNA of the invention comprising 2'-O-Me at positions 4, 14 and 17 and lacking 2'-O-Me at positions 6, 9 and 15 comprises a sense strand as set forth in SEQ ID NO:5, as follows: GAAUAGCAGCCAAGUAUCAGTT (modifications are marked in bold and underlined). A further currently preferred exemplary siRNA of the invention may further comprise an antisense strand as set forth in SEQ ID NO:6, as follows: UGAUACUUGGCUGCUAUUCtt.

An exemplary siRNA comprising 2'-O-Me at positions 4 and 17 and lacking 2'-0-Me at positions 6, 9 and 15 comprises a sense strand as set forth in SEQ ID NO:9, as follows: GAAUAGCAGCCAAGUAUCAGTT. The exemplary siRNA comprises an antisense strand as set forth in SEQ ID NO:12, as follows: UGAUACUUGGCUGCUAUUCtt (modifications are marked in bold and underlined).

In some embodiments, the unmodified VDAC1-silencing oligonucleotide is an siRNA comprising a first (sense) RNA strand and a second (antisense) RNA strand, wherein the first and the second RNA strands form an RNA duplex. These siRNA molecules typically further comprise 3' nucleotide overhangs on either or both strands, i.e. terminal portions of the nucleotide sequence that are not base paired between the two strands of the double stranded siRNA molecule. Preferably, the overhang is 1-5 nucleotides in length (e.g. 1-5 deoxythymidines), more preferably two nucleotides in length.

In certain exemplary embodiments, the VDAC1-silencing oligonucleotide comprises a first oligonucleotide comprising the sequence set forth in SEQ ID NO:21 and a second oligonucleotide comprising the sequence set forth in SEQ ID NO:22.

In additional certain exemplary embodiments, the VDAC1-silencing oligonucleotide comprises a first oligonucleotide comprising the sequence set forth in SEQ ID NO:23 and a second oligonucleotide comprising the sequence set forth in SEQ ID NO:24.

In yet additional certain exemplary embodiments, the VDAC1-silencing oligonucleotide comprises a first oligonucleotide comprising the sequence set forth in SEQ ID NO:25 and a second oligonucleotide comprising the sequence set forth in SEQ ID NO:26.

In further certain exemplary embodiments, the VDAC1-silencing oligonucleotide comprises a first oligonucleotide comprising the sequence set forth in SEQ ID NO:27 and a second oligonucleotide comprising the sequence set forth in SEQ ID NO:28.

Delivery of RNAi molecule, particularly siRNA molecule in its intact and active form to its site of action within a cell, typically within a tumor cell of a subject affected with cancerous disease, is mandatory for using the silencing molecule as a therapy. The present invention demonstrates that encapsulating the siRNA molecules of the invention with PEI-PLGA nanoparticles enabled administration of the siRNA molecule by i.v. injection, such that the siRNA molecule exerted its silencing activity.

Thus, according to certain exemplary embodiments, the siRNA molecules of the invention are associated with PLGA-based nanoparticles, particularly PEI-PLGA nanoparticles.

The present invention further provides a pharmaceutical composition comprising at least one modified VDAC1-silencing oligonucleotide of the invention, PLGA-based nanoparticles comprising same and one or more pharmaceutically acceptable diluents, carriers or excipients. In certain embodiments, said compositions is formulated for topical, intratumoral or pulmonary administration. In other embodiments, the composition is formulated for administration as an aerosol or mist. In another embodiment said composition is formulated for use with a nebulizer or inhaler.

The potent modified VDAC1-silencing oligonucleotides of the present invention can be used for treating a variety of cancer diseases.

According to a further aspect, the present invention provides a method of treating a tumor in a subject in need thereof, comprising administering to the subject a therapeutically effective amount at least one unmodified and/or modified VDAC1-silencing oligonucleotide of the invention or a pharmaceutical composition comprising same. According to certain embodiments, the tumor is characterized by VDAC1 over-expression in at least a portion of the tumor cells. In various embodiments, said tumor is selected from the group consisting of lung, bladder, mesothelioma, colon, pancreatic, prostate, thyroid, breast, brain, renal, melanoma, hepatocarcinoma, B cell chronic lymphocytic leukemia (CLL), and acute myeloid leukemia (AML). Each possibility represents a separate embodiment of the present invention.

According to yet further aspect, the present invention provides the use of at least one unmodified and/or modified VDAC1-silencing oligonucleotide of the invention or a pharmaceutical composition comprising same for treating a tumor in a subject in need thereof. The tumor types are as described hereinabove.

According to certain embodiment, the modified VDAC1-silencing oligonucleotide is an siRNA molecule comprising:

a. a first oligonucleotide having the sequence as set forth in SEQ ID NO:1 (GAAUAGCAGCCAAGUAUCAG) derivatized by 2'-O-methyl (2'-O-Me) at position 14 and/or at positions 4 and 17 of SEQ ID NO: 1, and/or b. a second oligonucleotide having the sequence as set forth in SEQ ID NO:2 (UGAUACUUGGCUGCUAUUC) derivatized by 2'-O-Me at positions 7 and 13 of SEQ ID NO:2, and/or c. an oligonucleotide complementary to the first or the second oligonucleotide.

According to certain embodiments, the first and/or the second oligonucleotide further comprises a 3' overhang of 1-5 nucleotides.

According to certain exemplary embodiments, the modified VDAC1-silencing siRNA molecule is an siRNA molecule comprising a first nucleotide having the sequences as set forth in SEQ ID NO:5 and a second oligonucleotide having the sequence as set forth in SEQ ID NO:6.

According to certain embodiments, the unmodified VDAC1-silencing oligonucleotide is an siRNA molecule selected from the group consisting of:

1. an siRNA molecule comprising a first oligonucleotide having the sequence set forth in SEQ ID NO:21 and a second oligonucleotide having the sequence set forth in SEQ ID NO:22;

2. an siRNA molecule comprising a first oligonucleotide having the sequence set forth in SEQ ID NO:23 and a second oligonucleotide having the sequence set forth in SEQ ID NO:24;

3. an siRNA molecule comprising a first oligonucleotide having the sequence set forth in SEQ ID NO:25 and a second oligonucleotide having the sequence set forth in SEQ ID NO:26; and 4. an siRNA molecule comprising a first oligonucleotide having the sequence set forth in SEQ ID NO:27 and a second oligonucleotide having the sequence set forth in SEQ ID NO:28.

Each possibility represents a separate embodiment of the present invention.

According to yet other embodiments, said VDAC1-silencing oligonucleotides and compositions may further be used in combinations with additional drugs and/or therapies know for treating the particular cancer type.

According to certain exemplary embodiments, the present invention provides the use of at least one modified VDAC1-silencing oligonucleotide of the invention for treating lung cancer.

Lung cancer is the most frequent and lethal type of cancer accounting for 1.8 million new cases (12.9% of all new cancer cases) and leading to 1.59 million deaths (19.3%) in 2012. Lung cancer is heavily associated with tobacco exposure with about 90% of lung cancer patients being active or former smokers (Hecht, S. S. 2002. Lancet Oncol 3, 461-469). In about 10% there are other factors causing lung cancer (Thun, M. J., et al. 2008. PLoS Med 5, e185). The outcome for lung cancer patients is very poor—the five-year survival rate is only about 16% for all patients. Notably, the incidence rate for lung cancer in the United States of America from 1975 to 2015 of men has dropped by 24% while it doubled within the same time for women. While in recent years there has been a stream of new life-extending treatments for lung cancer, it still remains a deadly disease and it remains one of the most difficult-to-treat cancers.

The two main forms of lung cancer are non-small cell lung cancer (NSCLC) and small cell lung cancer (SCLC) (Travis, W. D., et al. 2011. Proc Am Thorac Soc 8, 381-385). NSCLC is the most common form and accounts for about 85% of all cases with patients receiving typically combined platinum-based chemotherapy and radiotherapy before and after surgery (Vansteenkiste, J., et al. 2013. Ann Oncol 24 Suppl 6, vi89-98). Patients that harbor a NSCLC with stage IIIb or IV cannot be cured any more using chemotherapy, radiotherapy or/and surgery. For these patients targeting druggable oncogenic driver mutations is recommended (Reck, M., et al. 2014. Ann Oncol 25 Suppl 3, iii27-39). Personalized medicine has been proven to lead to a better survival in some cases with mutated EGFR targeted by EGFR-inhibition as erlotinib or gefitinib (Maemondo, M., et al. 2010. N Engl J Med 362, 2380-2388) or EGFR tyrosine kinase inhibitors (TKI) (Reck, M., et al. 2014, ibid). SCLC patients typically respond very well to initial standard chemotherapy with platinum and etoposide but show very soon a resistance phenotype and tumor relapse. The tumor is characterized by early metastasis and patients show a very poor 2-year survival of 5% for extensive stage or ~15% for limited stage disease (Pleasance, E. D., et al. 2010. Nature 463, 184-190).

According to further certain exemplary embodiments, the present invention provides the use of at least one modified VDAC1-silencing oligonucleotide of the invention for treating bladder cancer.

Bladder cancer is the ninth most common cancer worldwide and is the most common cancer of the urinary tract with ~380,000 new cases and ~150,000 deaths per year worldwide. Male:female ratio of bladder cancer is 3:1, being the fifth common cancer in males of western countries (Burger M, et al. 2013. Eur Urol 63:234 241). There are at least 5 types of bladder cancers: urothelial carcinoma, squamous cell carcinoma, adenocarcinoma, small cell carcinoma, and sarcoma. Of the 5, urothelial carcinoma is the most common cancer type of the bladder and urinary tract. The majority of urothelial cancer cases are located in the bladder, with 5-10% formed in the upper urinary tract. Carcinomas are classified into three categories: non-invasive cancers (~70%), muscle-invasive cancers (~30%) and metastases-forming tumors (rare).

According to yet additional certain exemplary embodiments, the present invention provides the use of at least one modified VDAC1-silencing oligonucleotides of the invention for treating cancer diseases characterized by tumors comprising cancer stem cells (CSC). According to certain embodiments, the modified VDAC1-silencing oligonucleotides are useful in the prevention CSC invasion and of tumor recurrence.

Mesothelioma is an aggressive form of cancer that develops from the thin layer of simple squamous epithelium that wraps internal organs such as lungs (Pleural mesothelioma), abdomen (Peritoneal mesothelioma) and in rare cases, the heart (Pericardial mesothelioma). Human malignant mesothelioma is a chemo-resistant tumor associated with exposure to pollutants, particularly asbestos. Recently, exposure to carbon nanotubes used to produce TVs, tennis rackets, sports cars and computer motherboards were also reported as a potential cause for mesothelioma. Rates of malignant mesothelioma occurrence are still rising in European countries. Australia is one of the highest burdens of malignant mesothelioma on a population basis in the world (Alfaleh, M. A., et al., PLoS One, 2017. 12(10):e0186137). According to the World Health Organization (WHO), 125 million workers are exposed to asbestos on a daily basis and it is estimated that 107,000 deaths occur annually (Ramazzini, C., J Occup Health, 2016. 58(2):220-223).

There are three primary types of mesothelioma: Pleural mesothelioma (lungs): 75% 80% of all cases; Peritoneal mesothelioma (abdomen): 20%-25% of all cases, and Pericardial mesothelioma (heart): less than 1% of all cases.

The median survival of patients with mesothelioma from time of diagnosis ranges between 1 and 2 years. Mesothelioma is mostly diagnosed in advanced stages and is refractory to conventional therapy, as chemotherapy (Alfaleh et al., 2017, ibid). In malignant pleural mesothelioma, treatment with standard treatment, such as cisplatinum/pemetrexed resulted in a survival benefit of only 3 months. Recently, it was shown that the treatment with anti-PD-L1 resulted in a benefit response of nearly 12 months (Alley, E. W., et al., Lancet Oncol, 2017. 18(5):623-630). The reported disadvantage of the anti-PD-L1-based therapy is the low (10-20%) positive response in patients, and the disease control being only about 50-60% (Hassan, R., et al., 2016. *Journal of Clinical Oncology* 34(15) suppl.:8503-8503).

The present invention demonstrates for the first time that silencing the expression of VDAC1 within mesothelioma tumor cells inhibited tumor development.

Thus, the present invention further provides a method for treating mesothelioma in a subject in need thereof, the method comprising administrating to the subject a therapeutically effective amount of at least one VDAC1-silencing oligonucleotide.

According to certain embodiments, the present invention provides use of a therapeutically effective amount of at least one VDAC1-silencing oligonucleotide or a composition comprising same for treating mesothelioma.

According to certain embodiments, treating comprises reducing cancer cell metabolic rate, cancer cell proliferation rate, tumor volume, or any combination thereof.

Breast cancer is one of the most common malignant tumors in women and is a heterogeneous disease that exhibits various biological characteristics and clinical behaviors. Breast cancers subtypes are defined on the basis of the presence or absence of estrogen receptors (ERs), progesterone receptors (PRs), and epidermal growth factor receptor-2, the receptor tyrosine-protein kinase erbB-2 (ERBB2/Her2). The majority (>60%) of breast cancers are ER-positive, whereas about 20% are defined as triple-negative breast cancer (TNBC), negative for ER, PR, and HER2 expression. Brest cancer stem cell-specific markers include BMI-1, CD44, CD24, CD49f, aldehyde dehydrogenase (ALDHA1), and EpCAM. CD24low/CD44+/ALDH bright cells have been consistently identified as having high tumorigenic potential in both human primary tumors and cell lines.

TNBC are known to be resistant to anti-cancer drugs, such as but not limited to herceptin, which target any one of abovementioned receptors. The present invention now shows that unexpectedly, treatment of TNBC MDA-MB-231 cell line, in culture or in xenograft mouse model, using siRNA targeting VDAC1, increased the levels of ER, PR, and ERBB2/Her2 receptors, as well as that of prolactin. Without wishing to be bound by ant specific theory or mechanism of action, the increased receptor expression suggests differentiation of the cancer cells into less malignant lineages. The induced expression of these receptors in TNBC cells upon reduction of VDAC1 expression may provide the means for a combination therapy of VDAC1 targeted siRNA with hormonal receptors (ER and PR)-and/or Her2-based therapy.

Thus, according to additional aspect the present invention provides a method for treating breast cancer in a subject in need thereof, comprising: administering to a subject having low or undetectable expression levels of estrogen receptor (ER), progesterone receptor (PR), and ERBB2/Her2 receptor compared to control an effective amount of VDAC1-silencing oligonucleotide, wherein the effective amount is sufficient to sensitize cancer cells of the subject to at least one anti-cancer drug having specific affinity to at least one of the ER, PR and ERBB2/Her2 receptor; and administering to said subject a therapeutically effective amount of the at least one anti-cancer drug, thereby treating breast cancer in said subject.

According to certain embodiments, the effective amount of the VDAC1-silencing oligonucleotide is sufficient to increase the expression level of at least one of the ER, PR and ERBB2/Her2 receptor in at least 1% of the cancer cells. According to some embodiments, the effective amount of the VDAC1-silencing oligonucleotide is sufficient to increase the expression level of at least one of the ER, PR and ERBB2/Her2 receptor in at least 2%, 3%, 4%, 5%, 6%, 7%, 8%, 9%, 10%, 15%, 20%, 25%, 30%, 35%, 40%, 45% or 50% of the cancer cells. Each possibility represents a separate embodiment of the present invention.

According to certain embodiments, the expression is increased compared to the expression detected in cancer cells of the subject before administering the VDAC1-silencing oligonucleotide. According to certain exemplary embodiments, the expression is increased to define the cancer cell as ER, PR, or ERBB2/Her2 receptor positive.

According to some exemplary embodiments, the effective amount of the VDAC1-silencing oligonucleotide reduces the expression level of VDAC1 mRNA or protein by from about 50% to about 100% compared to VDCA1 expression level in corresponding breast cancer cells not treated with said VDAC1-silencing oligonucleotide. According to certain embodiments, the effective amount reduces VDAC1 mRNA or protein expression level by from about 60% to about 90%.

Methods for determining gene expression levels are common and would be apparent to one of ordinary skill in the art. Non-limiting examples include, but are not limited to, quantitative real time RT-PCR (qRT-PCR) and immunoblotting, as exemplified hereinbelow.

According to certain embodiments, the VDAC1-silencing oligonucleotide is administered to the subject concurrently (e.g., in one composition or in two separate compositions) to administering the at least one anti-cancer drug having specific affinity to at least one of ER, PR and ERBB2/Her2 receptor.

According to certain embodiments, the VDAC1-silencing oligonucleotide is administered to the subject prior to administering the at least one anti-cancer drug having specific affinity to at least one of ER, PR and ERBB2/Her2 receptor. According to these embodiments, the method optionally further comprises detecting the expression level of the at least one ER, PR and ERBB2/Her2 receptor in cancer cells of the treated subject. In some embodiments, the at least one drug is administered to the subject when the expression level of the at least one ER, PR and ERBB2/Her2 receptor is increased compared to the expression detected in cancer cells of said subject before administering the VDAC1-silencing oligonucleotide. According to some embodiments, the at least one anti-cancer drug is administered from about 24 h to about 30 days after administering the VDAC1-silencing molecule. According to some exemplary embodiments, the at least one anti-cancer drug is administered from about 5 days to about 20 days after administering the VDAC1-silencing molecule.

As used herein, "specific affinity" to one or more targets selected from the group consisting of: estrogen receptor, progesterone receptor, and ERBB2/Her2 receptor refers to binding with a dissociation constant lower (Kd) than 10 nanomolar, lower than 1 nanomolar, lower than 100 picomolar, lower than 10 picomolar, lower than 1 picomolar, lower than 100 femtomolar, or any range or value therebetween. In some embodiments, specific affinity is binding with a Kd of 50-200 femtomolar, 100-800 femtomolar, 750-1,500 femtomolar, 1-50 picomolar, 40-150 picomolar, 100-500 picomolar, 350-1,050 picomolar, or 1-10 nanomolar. Each possibility represents a separate embodiment of the invention.

According to certain embodiments, an anti-cancer drug has specific affinity to aromatase. In some embodiments, the anti-cancer drug is an aromatase inhibitor. As used herein, the term "aromatase inhibitor" refers to a molecule inhibiting the activity of the aromatase enzyme, i.e., converting androgens to estrogens. In some embodiments, the aromatase inhibitor is steroidal or non-steroidal aromatase inhibitor. In some embodiments, the aromatase inhibitor reduces the amount of estrogen in a cell or a subject contacted therewith.

According to certain embodiments, the anti-cancer drug is a selective hormone-receptor modulator (e.g., estrogen receptor, progesterone receptor, and Her2). In some embodiments, the hormone-receptor modulator (i.e., the anti-cancer drug) is a hormone competitive inhibitor. In some embodiments, the hormone-receptor modulator is a hormone non-competitive inhibitor. In some embodiments, the competitive inhibitor binds to the hormone receptor as specified hereinabove with greater affinity than the native ligand/hormone. In some embodiments, the competitive inhibitor binds to the hormone receptor and further promotes or accelerates its degradation.

In some embodiments, the anti-cancer drug is selected from the group consisting of: trastuzumab (herceptin), trastuzumab emtansine, ado-trastuzumab emtansine (Kadcyla), neratinib (Nerlynx), pertuzumab (Perj eta), and lapatinib (Tykerb) and any other herceptin-based drug. Each possibility represents a separate embodiment of the present invention.

According to certain embodiments, treating comprises reducing cancer cell metabolic rate, cancer cell proliferation rate, tumor size, or any combination thereof. In some embodiments, treating comprises reducing the number of breast cancer stem cells, reducing the frequency of breast cancer stem cells, or any combination thereof.

As used herein, the term "size" comprises one or more measures, selected from the group consisting of: weight, volume, and surface area. In one embodiment, tumor size can be measured by any method known in the art.

As used herein, the term "cancer stem cell" refers to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cancer stem cells have the ability for self-renewal, multipotent differentiation and vigorous proliferative capacity.

According to certain embodiments, treating comprises reducing the expression of one or more proteins in cells of the cancer tumor, wherein the one or more biomarkers are selected from the group consisting of: Ki67, GLUT-1, HK-1, GAPDH, LDH-A, CS, ATPsyn5A, SOX2, KLF,4, CD133, EPCAM, CD44, c-Myc, HIF1-α, and phosphorylated NF-κB (p65).

According to certain additional or alternative embodiments, treating comprises increasing the expression levels of one or more additional biomarkers in the cells of the cancer tumor, wherein the one or more biomarkers are selected from the group consisting of: prolactin (PRLR), STAT5, p53, and CD24. Each possibility represents a separate embodiment of the present invention.

Various VDAC1-silencing oligonucleotides as are known in the art can be used for treating mesothelioma or TNBC according to the teachings of the present invention.

According to certain embodiments, the RNAi molecule is an unmodified and/or modified double stranded (ds) RNA molecules including, but not limited to, short-temporal RNA (stRNA), small interfering RNA (siRNA), short-hairpin RNA (shRNA), and microRNA (miRNA). According to certain currently exemplary embodiments, the RNAi is siRNA.

According to certain embodiments, the siRNA comprises a first oligonucleotide sequence identical to at least 15 nucleotides of SEQ ID NO:18 or to a mRNA encoded by same and a second oligonucleotide sequence essentially complementary to the first oligonucleotide. According to some embodiments, the first and/or the second oligonucle-otide comprise at least 15 nucleotides of SEQ ID NO:29 or mRNA encoded by same, encoding murine VDAC1. According to these embodiments, the siRNA molecule can silence both human and murine VDAC1. In some embodi- ments the first and second oligonucleotide sequences are annealed to each other to form the siRNA molecule.

According to certain embodiments, the VDAC1 silencing oligonucleotide molecules of the present invention for use in treating mesothelioma or TNBC are of at least 10, at least 15, at least 17 bases, or at least 20 bases specifically hybridiz-able with hVDCA1 encoding polynucleotide (SEQ ID NO:18). According to some embodiments, the VDAC1 silencing oligonucleotide molecules of the present invention are of at least 10, at least 15, at least 17 bases, or at least 20 bases specifically hybridizable with hVDCA1 encoding polynucleotide (SEQ ID NO:18) and with mVDAC1 encod-ing polynucleotide (SEQ ID NO:29). In some embodiments, the silencing oligonucleotide molecules are of 10-15 bases, 13-17 bases, or 15-20 bases specifically hybridizable with hVDAC1 mRNA (SEQ ID NO:18) and optional also with mVDAC1 (SEQ ID NO:29). Each possibility represents a separate embodiment of the invention.

According to certain embodiments, the siRNA is a single-stranded short hairpin RNA (shRNA) wherein the first oligonucleotide sequence is separated from the second oli-gonucleotide sequence by a linker which forms a loop structure upon annealing of the first and second oligonucle-otide sequences. In some embodiments the linker comprises 3, 5, 7, 10, 13, 15, 17, 21, 26, 30, 33, 38, 43, 47, 49, 51, 55, 58, 60 nucleotides, or any value or range therebetween. Each possibility represents a separate embodiment of the inven-tion.

According to certain embodiments, the siRNA is at least 15-50 nucleotides in length (e.g., each complementary sequence of the double stranded siRNA is about 15-50 nucleotides in length, and the double stranded siRNA is about 15-50 base pairs in length). In some embodiments, the siRNA is at least 19-30 nucleotides in length. In some embodiments, the siRNA is at least 19-25 nucleotides in length. In some embodiments, the siRNA is 15, 16, 17, 18, 19, 20, 21, 22, 23, 24, 25, 26, 27, 28, 29, 30 nucleotides in length, or any value or range there between. Each possibility represents a separate embodiment of the invention.

As used herein, the first and the second oligonucleotides are complementary to one another at a level of at least 70%, at least 80%, at least 90%, 100% complementary, or any value or range there between. In some embodiments, the first and the second oligonucleotides are complementary to one another at a level of 70-80%, 75-85%, 80-95%, or 90-100% complementary. Each possibility represents a separate embodiment of the invention.

According to certain exemplary methods the at least one VDAC1-silencing oligonucleotide for use in treating meso-thelioma or TNBC is selected from the group consisting of:

According to certain embodiments, the VDAC1-silencing siRNA molecule is selected from the group consisting of:
1. an siRNA comprising a first nucleotide having the sequences as set forth in SEQ ID NO:1 (GAAUAGCAGCCAAGUAUCAG) and a second oli-gonucleotide having the sequence as set forth in SEQ ID NO:2 (UGAUACUUGGCUGCUAUUC);
2. an siRNA comprising a first nucleotide having the sequences as set forth in SEQ ID NO:3 (GAAUAGCAGCCAAGUAUCAGtt) and a second oligonucleotide having the sequence as set forth in SEQ ID NO:4 (UGAUACUUGGCUGCUAUUCtt);

3. an siRNA comprising a first nucleotide having the sequences as set forth in SEQ ID NO:5 (GAAUAGCAGCCAAGUAUCAGtt) and a second oligonucleotide having the sequence as set forth in SEQ ID NO:6 (UGAUACUUGGCUGCUAUUCtt);
4. an siRNA comprising a first nucleotide having the sequences as set forth in SEQ ID NO:7 (GAAUAGCAGCCAAGUAUCAGtt) and a second oligonucleotide having the sequence as set forth in SEQ ID NO:10 (UGAUACUUGGCUGCUAUUCtt);
5. an siRNA comprising a first nucleotide having the sequences as set forth in SEQ ID NO:8 (GAAUAGCAGCCAAGUAUCAGtt) and a second oligonucleotide having the sequence as set forth in SEQ ID NO:11 (UGAUACUUGGCUGCUAUUCtt);
6. an siRNA comprising a first nucleotide having the sequences as set forth in SEQ ID NO:9 (GAAUAGCAGCCAAGUAUCAGtt) and a second oligonucleotide having the sequence as set forth in SEQ ID NO:12 (UGAUACUUGGCUGCUAUUCtt);
7. an siRNA comprising a first nucleotide having the sequences as set forth in SEQ ID NO:15 (ACAC-UAGGCACCGAGAUUA) and a second oligonucle-otide having the sequence as set forth in SEQ ID NO:16 (UAAUCUCGGUGCCUAGUGU);
8. an siRNA comprising a first nucleotide having the sequences as set forth in SEQ ID NO:19 (ACAC-UAGGCACCGAGAUUA) and a second oligonucle-otide having the sequence as set forth in SEQ ID NO:20 (UAAUCUCGGUGCCUAGUG);
9. an siRNA molecule comprising a first oligonucleotide having the sequence set forth in SEQ ID NO:21 (CUUGAUUUGAAAACAAAAUCU) and a second oligonucleotide having the sequence set forth in SEQ ID NO:22 (AUUUUGUUUUCAAAUCAAGCU);
10. an siRNA molecule comprising a first oligonucleotide having the sequence set forth in SEQ ID NO:23 (GAAUGGAUUGGAAUUUACAAG) and a second oligonucleotide having the sequence set forth in SEQ ID NO:24 (UGUAAAUUCCAAUCCAUUCUC);
11. an siRNA molecule comprising a first oligonucleotide having the sequence set forth in SEQ ID NO:25 (CGUUUACAGAGAAAUGGAAUA) and a second oligonucleotide having the sequence set forth in SEQ ID NO:26 (UUCCAUUUCUCUGUAAACGUC); and
12. an siRNA molecule comprising a first oligonucleotide having the sequence set forth in SEQ ID NO:27 (CAAAAUCUGAGAAUGGAUUGG) and a second oligonucleotide having the sequence set forth in SEQ ID NO:28 (AAUCCAUUCUCAGAUUUUGUU);
wherein nucleotides derivatized by 2'-O-Me are marked in bold and underlined.

Each possibility represents a separate embodiment of the present invention.

The silencing oligonucleotide molecules designed accord-ing to the teachings of the present invention can be generated according to any nucleic acid synthesis method known in the art, including both enzymatic syntheses and solid-phase syntheses. Any other means for such synthesis may also be employed; the actual synthesis of the nucleic acid agents is well within the capabilities of one of ordinary skill in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Maryland; Perbal, B. (1988), "A Practical Guide to Molecular Cloning," John Wiley & Sons, New York; and Gait, M. J., ed. (1984).

It will be appreciated that silencing oligonucleotides of the present invention can be also generated using an expression vector as is further described hereinbelow.

For example, the silencing oligonucleotide molecules of the present invention may comprise heterocylic nucleosides consisting of purines and the pyrimidines bases, bonded in a 3'-to-5' phosphodiester linkage. In some embodiments, the nucleic acid agents are modified either in backbone, internucleoside linkages, or bases, as is broadly described hereinbelow.

Specific examples of silencing oligonucleotide molecules useful according to this aspect of the present invention include oligonucleotides or polynucleotides containing modified backbones or non-natural internucleoside linkages.

Oligonucleotides or polynucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

In some embodiments, modified oligonucleotide backbones include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; and boranophosphates having normal 3'-5' linkages, 2'-5' linked analogues of these, and those having inverted polarity wherein the adjacent pairs of nucleoside units are linked 3'-5' to 5'-3' or 2'-5' to 5'-2'. Various salts, mixed salts, and free acid forms of the above modifications can also be used.

Alternatively, modified oligonucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437 and 5,677,439.

Other silencing oligonucleotide molecules which may be used according to the present invention are those modified in both sugar and the internucleoside linkage, i.e., the backbone of the nucleotide units is replaced with novel groups. The base units are maintained for complementation with the appropriate polynucleotide target. An example of such an oligonucleotide mimetic includes a peptide nucleic acid (PNA). A PNA oligonucleotide refers to an oligonucleotide where the sugar-backbone is replaced with an amide-containing backbone, in particular an aminoethylglycine backbone. The bases are retained and are bound directly or indirectly to aza-nitrogen atoms of the amide portion of the backbone. United States patents that teach the preparation of PNA compounds include, but are not limited to, U.S. Pat. Nos. 5,539,082; 5,714,331; and 5,719,262. Other backbone modifications which may be used in the present invention are disclosed in U.S. Pat. No. 6,303,374.

Silencing oligonucleotide molecules of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 2'-O-methyl-modified nucleotides, particularly uracil and guanine; 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. 1990, "The Concise Encyclopedia of Polymer Science and Engineering" pages 858-859, John Wiley & Sons; Englisch et al. 1991. Angewandte Chemie, International Edition, 30, 613; and Sanghvi, Y. S., "Antisense Research and Applications," Chapter 15, pages 289-302, S. T. Crooke and B. Lebleu, eds., CRC Press, 1993. Such modified bases are particularly useful for increasing the binding affinity of the oligomeric compounds of the invention. These include 5-substituted pyrimidines, 6-azapyrimidines, and N-2, N-6, and O-6-substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S. et al. 1993, "Antisense Research and Applications," pages 276-278, CRC Press, Boca Raton), and are presently preferred base substitutions, even more particularly when combined with 2'-O-methoxyethyl sugar modifications.

It will be appreciated that the VDAC1 silencing oligonucleotides of the present invention may be expressed directly in the subject (i.e. in vivo gene therapy) or may be expressed ex vivo in a cell system (autologous or nonautologous) and then administered to the subject.

To express such an agent (i.e., to produce an RNA molecule) in mammalian cells, a nucleic acid sequence encoding the agents of the present invention is ligated into a nucleic acid construct suitable for a host cell expression. Non-limiting examples of a host cell include, mammalian cell, yeast cell, bacteria, and a plant cell.

Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the tetracycline-inducible promoter (Zabala M, et al., 2004. Cancer Res., 64(8), 2799-804).

The nucleic acid construct (also referred to herein as an "expression vector") includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Various methods can be used to introduce the expression vector as mentioned hereinabove into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. 1989; Chang et al., Somatic Gene Therapy, CRC Press, Ann Arbor, Mich. 1995; Vega et al, Gene Targeting, CRC Press, Ann Arbor Mich. 1995; Vectors: A Survey of Molecular Cloning Vectors and Their Uses, Butterworths, Boston Mass. 1988; and Gilboa et al. 1986 Biotechniques 4(6), 504-512) and include, for example, stable or transient transfection, lipofection, electroporation and infection with recombinant viral vectors. In addition, see U.S. Pat. Nos. 5,464,764 and 5,487,992 for positive-negative selection methods.

Other than containing the necessary elements for the transcription of the inserted coding sequence, the expression construct can also include sequences engineered to enhance stability, production, purification, yield or effective activity of the expressed RNA.

Pharmaceutical Compositions

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism. According to the present invention, "an active ingredient" refers to VDAC1-silencing oligonucleotide.

Suitable routes of administration may, for example, include parenteral, transmucosal, especially transnasal, intestinal, rectal, or oral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into the tumor (i.e. in situ).

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredient into preparations which, can be used pharmaceutically. Proper formulation is dependent upon the route of administration chosen.

For injection, the active ingredient of the pharmaceutical composition may be formulated in aqueous solutions, including physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compound with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropyknethyl-cellulose, sodium carbomethylcellulose; and/or physiologically acceptable polymers such as polyvinylpyrrolidone (PVP), Polylactide/Poly(lactide-co-glycolide) (PLGA), lipid-based nanoparticles. If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredient for use according to the present invention is conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredient may be prepared as appropriate oily or water-based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water-based solution, before use.

Pharmaceutical compositions suitable for use in context of the present invention include compositions wherein the active ingredient is contained in an amount effective to achieve the intended purpose. More specifically, a therapeutically effective amount means an amount of active ingredient (naked silencing oligonucleotides and/or encapsulated or shielded silencing oligonucleotides) effective in reducing VDAC1 expression and in preventing, alleviating or ameliorating tumor progression, invasion and recurrence, or prolonging the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredient described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide the active ingredient sufficiently to induce or suppress the biological effect.

Depending on the severity and responsiveness of the condition to be treated, dosing can be of a single or a plurality of administrations, with course of treatment lasting from several days to several weeks or until cure is affected or diminution of the disease state is achieved.

The amount of a composition to be administered will, of course, be dependent on the subject being treated, the severity of the affliction, the manner of administration, the judgment of the prescribing physician, etc.

Compositions of the present invention, if desired, can be presented in a pack or dispenser device, such as an U.S. Food and Drug Administration (FDA) approved kit, which may contain one or more unit-dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials

The cell transfection agents JetPRIME and JetPEI were from PolyPlus transfection (Illkirch, France), VDAC1-siRNA was obtained from Genepharma (Suzhou, China). Propidium iodide (PI), sulforhodamine B (SRB), Triton X-100, and Tween-20 were obtained from Sigma (St. Louis, MO). Paraformaldehyde was purchased from Emsdiasum (Hatfield, PA). Dulbecco's modified Eagle's medium (DMEM) and Roswell Park Memorial Institute (RPMI) 1640 growth media were obtained from Gibco (Grand Island, NY). Normal goat serum and the supplements fetal calf serum (FCS), L-glutamine and penicillin-streptomycin were obtained from Biological Industries (Beit Haemek, Israel). Horseradish peroxidase (HRP)-conjugated anti-mouse, anti-rabbit and anti-goat antibodies were from KPL (Gaithersburg, MD). Antibodies against the indicated protein, their catalogue number, source, and the dilutions used in IHC, immunoblot and immunofluorescence experiments are presented in Table 1 hereinbelow. 3,3-diaminobenzidine (DAB) was obtained from ImmPact-DAB (Burlingame, CA). Tissue array slides were purchased from Biomax (Derwood, US Biomax).

Biomax, Inc. USA), formalin-fixed and paraffin-embedded tumor sections were immunohistochemically (IHC) stained. Sections were deparaffinized using xylene and a graded

TABLE 1

|  | | Dilution | | |
| --- | --- | --- | --- | --- |
| Antibody | Source and Cat. No. | IHC | WB | IF |
| Mouse monoclonal anti-β-actin | Millipore, Billerica, MA, MAB1501 | — | 1:10000 | |
| Rabbit polyclonal anti-citrate synthase | Abcam, Cambridge, UK ab96600 | 1:200 | 1:4000 | |
| Rabbit monoclonal anti-Ki67 | Thermo Scientific, NY RM-9106-s1 | 1:100 | — | |
| Rabbit monoclonal anti-VDAC1 | Abcam, Cambridge, UK, ab154856 | 1:500 | 1:5000 | |
| Rabbit monoclonal anti-Glut1 | Abcam, Cambridge, UK ab40084 | — | 1:1500 | — |
| Mouse monoclonal anti-GAPDH | Abcam, Cambridge, UK, ab9484 | — | 1:1000 | — |
| Mouse monoclonal anti-ATP synthase 5a | Abcam, Cambridge, UK, ab14748 | — | 1:1000 | — |
| Mouse monoclonal anti-HK-I | Abcam, Cambridge, UK ab105213 | — | 1:2000 | — |
| Goat polyclonal anti-LDH-A | Santa Cruz Biotechnology, Inc. Dallas, TX, sc-27230 | — | 1:1500 | — |
| Mouse monoclonal anti-ABCG2 | GeneTex, Irvine, CA, cat: GTX60447 | — | 1:2000 | — |
| Goat polyclonal anti-Sox2 | Santa Cruz Biotechnology, Inc. Dallas, TX, sc-17320 | 1:300 | 1:1500 | |
| Rabbit polyclonal anti-KLF4 | IMGENX Littleton, USA, IMG-6081-A | 1:200 | 1:1000 | — |
| Mouse monoclonal anti-CD133 | Miltenyi Biotec GmbH , AC133 | — | 1:1500 | |
| Alexa Fluor 488 anti-mouse/human CD44 | Biolegend, San Diego, CA, cat: 103015 | — | — | 1:500 |
| Mouse monoclonal anti-erb B2/HER-2 | Biolegend, San Diego, CA, cat: 324401 | — | — | 1:500 |
| Mouse monoclonal anti-CD24 | Biolegend, San Diego, CA, cat: 311101 | — | — | 1:500 |

Cell Culture and Transfection

Cell line used were A549 (human non-small cell lung adenocarcinoma); U-87MG (human glioblastoma); CT26 (mouse colon carcinoma); 3LL, (Lewis lung carcinoma); AB1, (mouse malignant mesothelioma); H226 (human Squamous Cell Carcinoma; Mesothelioma); UMUC-3 (human bladder transitional cell carcinoma); HepG2 (liver hepatocellular) and MDA-MB-231 (human breast carcinoma). Cells were grown in the appropriate medium and maintained in a humidified atmosphere at 37° C. with 5% $CO_2$.

siRNAs were synthesized by Genepharma (Suzhou, China). Cells were seeded (150,000 cells/well) in 6-well culture plates, cultured to 40-60% confluence and transfected with 10-100 nM si-NT, si-hVDAC1 or si-m/hVDAC1 using the JetPRIME transfection reagent (Illkirch, France), or the indicated reagent, including TurbFect, Lipid R and Genemute according to the manufacturer's instructions.

Sulforhodamine B (SRB) Cell Proliferation Assay

Twenty-four hours post-transfection with si-NT, si-hVDAC1 or si-m/hVDAC1 or other version of siVDAC1, cells were counted and seeded in 96-well plates (10,000/well). After an additional 48, 72 or 96 h, the cells were washed with PBS, fixed with 10% trichloroacetic acid, and stained with SRB. SRB was extracted from the cells using 100 mM Tris-base and absorbance at 510 nm was determined using an Infinite M1000 plate μ

Immunohistochemistry

Tissue microarrays (MC5003, LC807) containing cancer and normal tissues purchased from US Biomax (US ethanol series. Endogenous peroxidase activity was blocked by incubating the sections in 3% $H_2O_2$ for 10 minutes. Antigen retrieval was performed in 0.01 M citrate buffer (pH 6.0) at 95° C.-98° C. for 20 minutes. After washing sections with PBS containing 0.1% Triton-X100 (pH 7.4), non-specific antibody binding was reduced by incubating the sections in 10% normal goat serum for 2 h. After decanting excess serum, sections were incubated overnight at 4° C. with primary antibodies (sources and dilutions are detailed in Table 1). Sections were washed with PBST. For IHC, endogenous peroxidase activity was blocked by incubating the sections in 3% $H_2O_2$ for 15 min. After washing thoroughly with PBST, the sections were incubated for 2 h with anti-mouse or anti rabbit (1:250) secondary antibodies conjugated to HRP, as appropriate. Sections were washed five times in PBST and the peroxidase reaction was subsequently visualized by incubating with DAB. After rinsing in water, the sections were counterstained with hematoxylin, and mounted with Vectashield mounting medium (Vector Laboratories, Burlingame, CA). Finally, the sections were observed under a microscope (Leica DM2500) and images were collected at 20× magnification with the same light intensity and exposure time.

Immunoblot

For immunostaining, membranes containing electro-transferred proteins following SDS-PAGE were blocked with 5% non-fat dry milk and 0.1% Tween-20 in TBS, incubated with the primary antibodies (sources and dilutions as detailed in Table 1) and then with HRP-conjugated anti-mouse or anti-rabbit (1:10,000) or anti-goat (1:20,000) IgG. Enhanced chemiluminiscent substrate (Pierce Chemical, Rockford, IL) was used for detection of HRP activity. Band intensity was quantified using FUSION-FX (Vilber Lourmat, France).

Xenograft Experiments

Xenografts Derived from H226 Human Mesothelioma Cells

H226 human mesothelioma cells ($5 \times 10^6$ in 0.1 ml PBS with 20% Matrigel) were inoculated sub-cutaneously (s.c.) into the hind leg flanks of 7-week-old athymic male nude mice (Envigo). When the tumor volume reached 50-75 mm$^3$, the mice were randomized into 2 groups (8 animals/group) and treated with -si-NT or si-m/hVDAC1-B mixed with in vivo JetPEI reagent, injected into the established s.c. tumors (100 nM final concentration, 2 boluses) every 3 days.

Mouse mesothelioma AB1 cells ($5 \times 10^5$ in 0.1 ml PBS) were sub-cutaneously inoculated into the hind leg flanks of 6-week-old BALB/c female mice (Envigo). When the tumor volume reached 50-75 mm$^3$, the mice were randomized into 2 groups (8 animals/group) and treated with si-NT or si-m/hVDAC1-B mixed with in vivo JetPEI reagent, injected into the established s.c. tumors (100 nM final concentration, 2 boluses) every 3 days.

At the end of the experiment, the mice were sacrificed, tumors were excised and half of each tumor was either fixed and processed for immunohistochemistry (IHC) or frozen in liquid nitrogen for later immunoblot analysis.

Xenografts Derived from MDA-MB-231 Cells

MDA-MB-231 ($2 \times 10^6$) were subcutaneously (s.c.) inoculated into the hind leg flanks of athymic eight-week-old male nude mice (Envigo). Fourteen days after inoculation, the volume of the tumour was measured (50-80 mm$^3$) and the mice were randomised into two groups (8 animals/group), treated with si-NT or si-hVDAC1 mixed with in vivo JetPEI reagent and injected into the established s.c. tumors (50 nM final, 2 boluses) once every three days. At the end of the experiment, the mice were sacrificed, tumors were excised, and half of each tumor was either fixed and processed for immunohistochemistry (IHC) or frozen in liquid nitrogen for later immunoblot and RNA isolation.

RNA Preparation and Quantitative Real-Time PCR (qRT-PCR)

Total RNA was isolated from si-NT-treated tumours (TTs), and si-hVDAC1-TTs (from 4 mice each) or from MDA-MB-231 cells following first, second, third or fourth transfection with si-NT or si-hVDAC1. Isolated total RNA was used for complementary DNA synthesis, and further amplified by real-time RT-PCR using specific primers (Table 2). Copy numbers for each sample were calculated by the CT-based calibrated standard curve approach. The mean fold change ($\pm$SEM) of the three replicates was calculated.

TABLE 2

Real-Time RT-PCR primers used in this study

| Gene | Primer sequences | SEQ ID NO. |
|---|---|---|
| β-Actin | Forward 5'-ACTCTTCCAGCCTTCCTTCC-3' | 78 |
| | Reverse 5'-TGTTGGCGTACAGGTCTTTG-3' | 79 |
| VDAC1 | Forward 5'-AATGACGGGACAGAGTTTGG-3' | 80 |
| | Reverse 5'-AGCGCGTGTTACTGTTTCCT-3' | 81 |
| GLUT1 | Forward 5'-GGCCATCTTTTCTGTTGGGG-3' | 82 |
| | Reverse 5'-TCAGCATTGAATTCCGCCG-3' | 83 |

TABLE 2-continued

Real-Time RT-PCR primers used in this study

| Gene | Primer sequences | SEQ ID NO. |
|---|---|---|
| GAPDH | Forward 5'-TGGAAGGACTCATGACCACA-3' | 84 |
| | Reverse 5'-ATGATGTTCTGGAGAGCCCC-3' | 85 |
| LDH-A | Forward 5'-GCAGGTGGTTGAGAGTGCTT-3' | 86 |
| | Reverse 5'-GCACCCGCCTAAGATTCTTC-3' | 87 |
| CS | Forward 5'-AGGAACAGGTATCTTGGCTCT-3' | 88 |
| | Reverse 5'-GGGGTGTAGATTGGTGGGAA-3' | 89 |
| ATP syn5α | Forward 5'-TCAGTCTACGCCGCACTTAC-3' | 90 |
| | Reverse 5'-GACATCTCAGCAGTCCCACA-3' | 91 |
| HK-1 | Forward 5'-GTCTCAGTCCAGCACGTTTG-3' | 92 |
| | Reverse 5'-GAAACGCCGGGAATACTGTG-3' | 93 |
| KLF4 | Forward 5'-TGCCCCGAATAACCGCTG-3' | 94 |
| | Reverse 5'-CGTTGAACTCCTCGGTCTCT-3' | 95 |
| SOX2 | Forward 5'-CCATGCAGGTTGACACCGTTG-3' | 96 |
| | Reverse 5'-TCGGCAGACTGATTCAAATAA-3' | 97 |
| PRLR | Forward 5'-AATCTTGGCAGAGGCAGAAA-3' | 98 |
| | Reverse 5'-TTTGGAGCTATTCCCATTGC-3' | 99 |
| HER2 | Forward 5'-ACAGTGGCATCTGTGAGCTG-3' | 100 |
| | Reverse 5'-CCCACGTCCGTAGAAAGGTA-3' | 101 |
| PR | Forward 5'-GTCTACCCGCCCTATCTCAAC-3' | 102 |
| | Reverse 5'-ACCATAATGACAGCCTGATGC-3' | 103 |
| ER | Forward 5'-TGGAGATCTTCGACATGCTG-3' | 104 |
| | Reverse 5'-TCCAGAGACTTCAGGGTGCT-3' | 105 |
| CD24 | Forward 5'-CCTGCAGTCAACAGCCAGT-3' | 106 |
| | Reverse 5'-TTTTCCTTGCCACATTGGA-3' | 107 |
| STAT5 | Forward 5'-GTTGGTGGAAATGAGCTGGT-3' | 108 |
| | Reverse 5'-AGGCTCTGCAAAAGCATTGT-3' | 109 |
| CD133 | Forward 5'-TGGGCTTGTCATAACAGGAT-3' | 110 |
| | Reverse 5'-TTGCGGTAAAACTGGCTAAG-3' | 111 |
| ALDH1 | Forward 5'-CCAAAGTCCTGGAGGTTGAA-3' | 112 |
| | Reverse 5'-TAACTCCAGGCCATCACACA-3' | 113 |
| EPCAM | Forward 5'-CTGGCCGTAAACTGCTTTGT-3' | 114 |
| | Reverse 5'-TCCCAAGTTTTGAGCCATTC-3' | 115 |

Urethane-Induced Lung Cancer in A/J Mice

A/J mice are widely used to model cancer and for carcinogen testing given their high susceptibility to carcinogen-induced tumors. Urethane caused tumors in several rodent species at several different tissue sites and by several different routes of exposure. It was carcinogenic following administration of a single dose and by prenatal exposure. Malignant and/or benign tumors of the lung, liver, and blood vessels were seen in many studies, along with lymphoma, leukemia, or melanoma.

Urethane-induced lung cancer mode of action involves induction of mutation during DNA replication including KrasQ61L mutation and other genetic and epigenetic events leading to lung tumors (Gurley, K. E., et al., 2015. Cold Spring Harb Protoc. doi:10.1101/pdb.prot077446).

The protocol used for inducing lung tumors by urethane is as described previously (Redente, E. F., et al., 2007. The American journal of pathology, 170(2):693-708).

Figure 9:
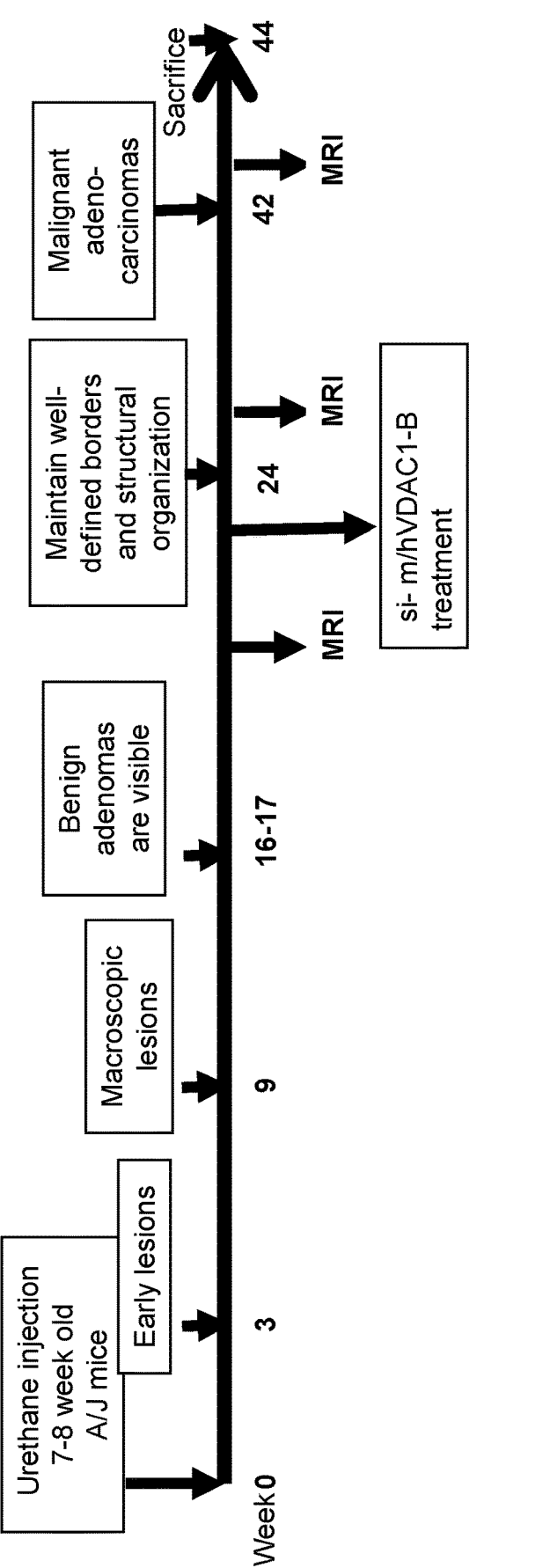
FIG. 9 is a non-limiting schematic presentation of the protocol for urethane-induced lung cancer, including time course of tumors development, treatment with si-m/hVDAC1-B encapsulated in PLGA nano-particles and MRI imaging.
Figure 10A:
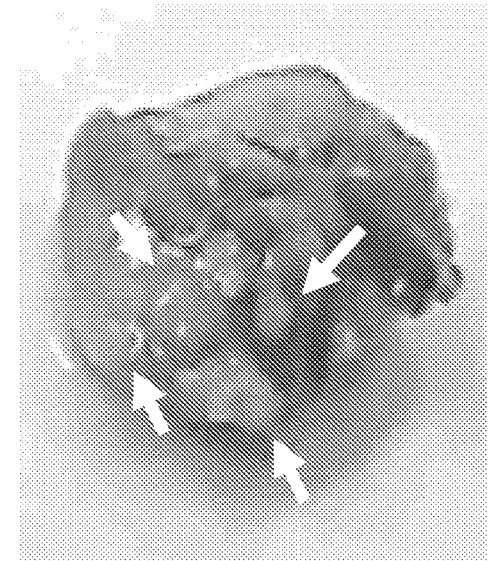
FIG. 10A shows photographs of lungs from mice subjected to urethane. Arrows point to the tumors.
Figure 10A:
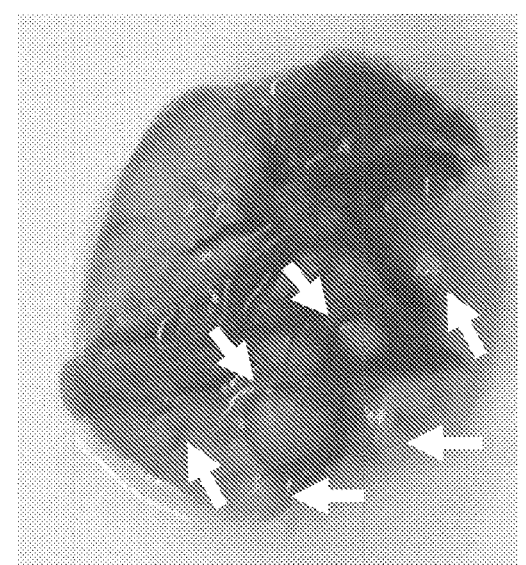
Figure 10A:
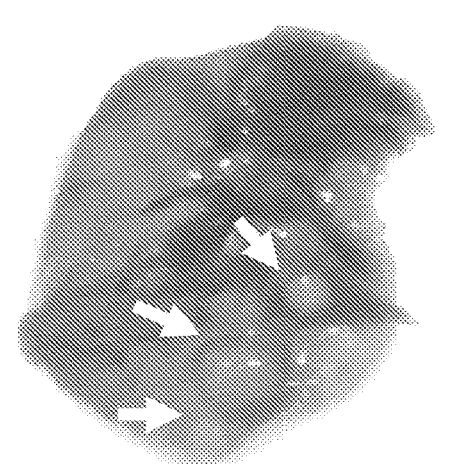
Figure 10B:
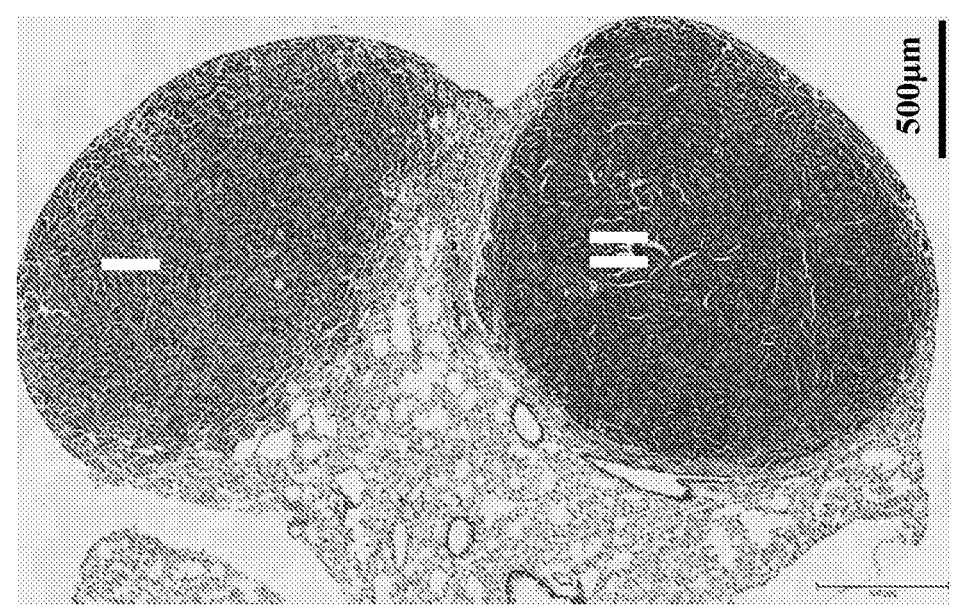
FIG. 10B-D show lung tumors sections from mice subjected to urethane with FIGS. 10C and 10D representing enlargements of sections (I) and (II) of FIG. 10B, respectively. The two types of tumors represent small and non-small-cell lung carcinoma
Figures 10C, 10D:
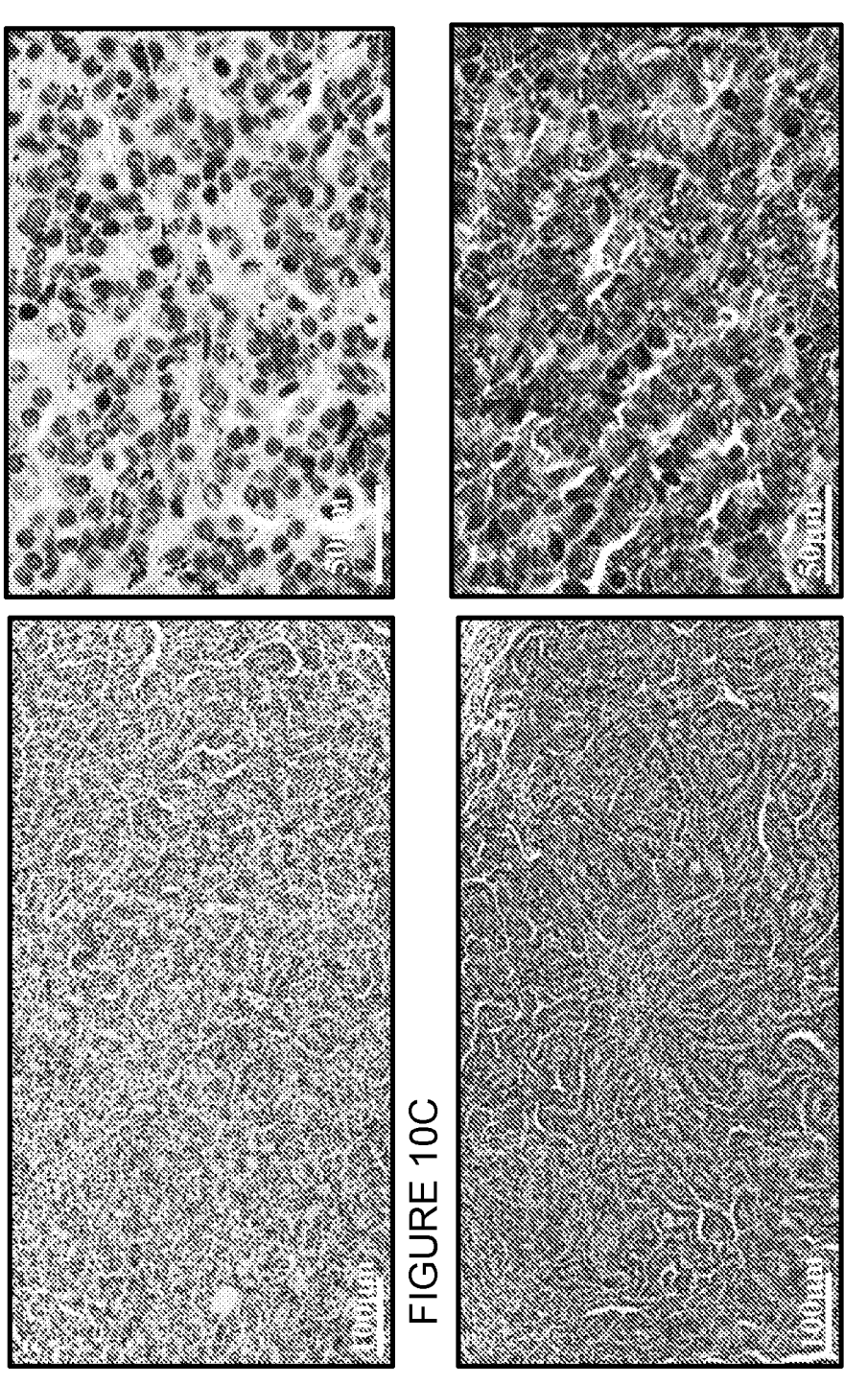

Urethane in 0.9% NaCl (saline) was injected IP (1 mg urethane/gr body weight). Protocol for urethane-induced lung cancer, time course of tumors development and treatment with siRNA and MRI imaging is described in FIG. 9. si-m/hVDAC1-B and si-NT encapsulation in PEI-PLGA nano-particles was performed by the solvent displacement method (Das J, et al., 2014. Toxicol Lett. 225(3):454-466). At the end of the experiments, the mice were sacrificed and the tumors were excised and processed for immunohistochemistry or frozen in liquid nitrogen for immunoblotting and RNA isolation.

Example 1: Unexpectedly Improved Modified siRNAs

Human A549 lung cancer cells and murine CT26 colon carcinoma cells were incubated with the siRNAs listed in Table 3 below (50 nM for 48 hours). VDAC1 expression was subsequently analyzed by immunoblotting using VDAC1-specific antibodies as detailed in Table 1.

TABLE 3 siRNAs used in the comparative experiments

| Description | siRNA sequence | SEQ ID NO. |
|---|---|---|
| Human specific VDAC1 siRNA (si-hVDAC1, 2/A), | S: ACACUAGGCACCGAGAUUA<br>AS: UAAUCUCGGUGCCUAGUGU | 15<br>16 |
| Scrambled siRNA, with no specific target (si-NT; si-SCR) | S: GCAAACAUCCCAGAGGUAU<br>AS: AUACCUCUGGGAUGUUUGC | 13<br>14 |
| Human and mouse cross-reactive VDAC1 siRNA, non-modified (si-m/hVDAC1) | S: GAAUAGCAGCCAAGUAUCAGtt<br>AS: UGAUACUUGGCUGCUAUUCtt | 3<br>4 |
| Modified si-m/hVDAC1-A | S: GAAUAGCAGCCAAGUAUCAGtt<br>AS: UGAUACUUGGCUGCUAUUCtt | 7<br>10 |
| Modified Si-m/hVDAC1-B, | S: GAAUAGCAGCCAAGUAUCAGtt<br>AS: UGAUACUUGGCUGCUAUUCtt | 5<br>6 |
| Modified Si-m/hVDAC1-C | S: GAAUAGCAGCCAAGUAUCAGtt<br>AS: UGAUACUUGGCUGCUAUUCtt | 8<br>11 |
| Modified si-m/hVDAC1-D | S: GAAUAGCAGCCAAGUAUCAGtt<br>AS: UGAUACUUGGCUGCUAUUCtt | 9<br>12 |

Table 3: nucleotides derivatized by 2'-O-Me are marked in bold and underline.
S-sense oligonucleotide.
AS-Antisense oligonucleotide.

As can be seen in FIG. 1, VDAC1-specific siRNAs reduced the expression of VDAC1 in the transfected cell lines. Unexpectedly, a human and mouse cross-reactive VDAC1 siRNA specifically modified by 2'-O methylation (2'-O Me) at positions 4, 14 and 17 of its sense strand, and at positions 7 and 13 of its antisense strand (B, SEQ ID NOs:5 and 6, respectively), was significantly more effective in reducing VDAC1 expression than the non-modified sequence, compared to siRNAs modified at other positions. This finding is particularly surprising under the experimental conditions employed.

It is noted that siRNA molecules B-D all contain modifications at positions 4 and 17 of their sense strand, and differ only by a single modification (modification at position 14 in siRNA B compared to modification at position 9 in siRNA C and no further modification in siRNA D). Thus, the modification at position 14 of the sense strand may be of particular importance to the efficacy of the siRNAs. In addition, siRNAs A and C, both modified inter alia at position 9 of their sense strand, were less effective than the other siRNAs, including the non-modified sequence. Of note, siRNA C, modified at positions 4, 9 and 17 of the sense strand, was significantly less effective than siRNA D, modified at positions 4 and 17 only. Thus, modifications at position 9, and possibly also at positions 6 and/or 15 of the sense strand, may be associated with decreased efficacy of the siRNAs.

It is further noted that siRNAs A-C all contain modifications at position 13 of their antisense strand. Thus, the modification at position 7 of the antisense strand present in siRNA B may be of particular importance to the efficacy of the siRNAs. In addition, it is noted that siRNA D, exhibiting enhanced efficacy compared to siRNAs A and C, is modified at positions 4, 10 and 18 of its antisense strand.

As exemplified herein, VDAC1-silencing oligonucleotides comprising a sense strand having the nucleic acid sequence as set forth in SEQ ID NO:3, comprising 2'-O-Me modifications preferably at positions 4, 14, and 17, in the absence of a 2'-O-Me modification at position 9 (SEQ ID NO:5), and comprising an antisense strand having the nucleic acid sequence as set forth in SEQ ID NO:4, comprising 2'-O-Me modifications preferably at positions 7 and 13 (SEQ ID NO:6), exhibit unexpectedly improved anticancer properties.

Example 2: Unexpectedly Potent siRNA Molecules

The unexpected discovery that specific siRNA molecules targeted to silence VDAC1 expression are more potent that others, additional molecules were designed and examined.

The siRNA molecules were designed using 2 different programs (GenScript siRNA Target Finder and siDirect version 2.0). Table 4 below presents the designed molecules, including the position of the selected sequence in human mRNA (SEQ ID NO:18), and the sequence of each molecule sense and antisense oligonucleotides. The term si-hVDAC1 refers to siRNA molecules recognizing only the human VDAC1 target sequence and si-m/hVDAC1 to siRNA molecules recognizing both murine and human VDAC1.

Figure 2:
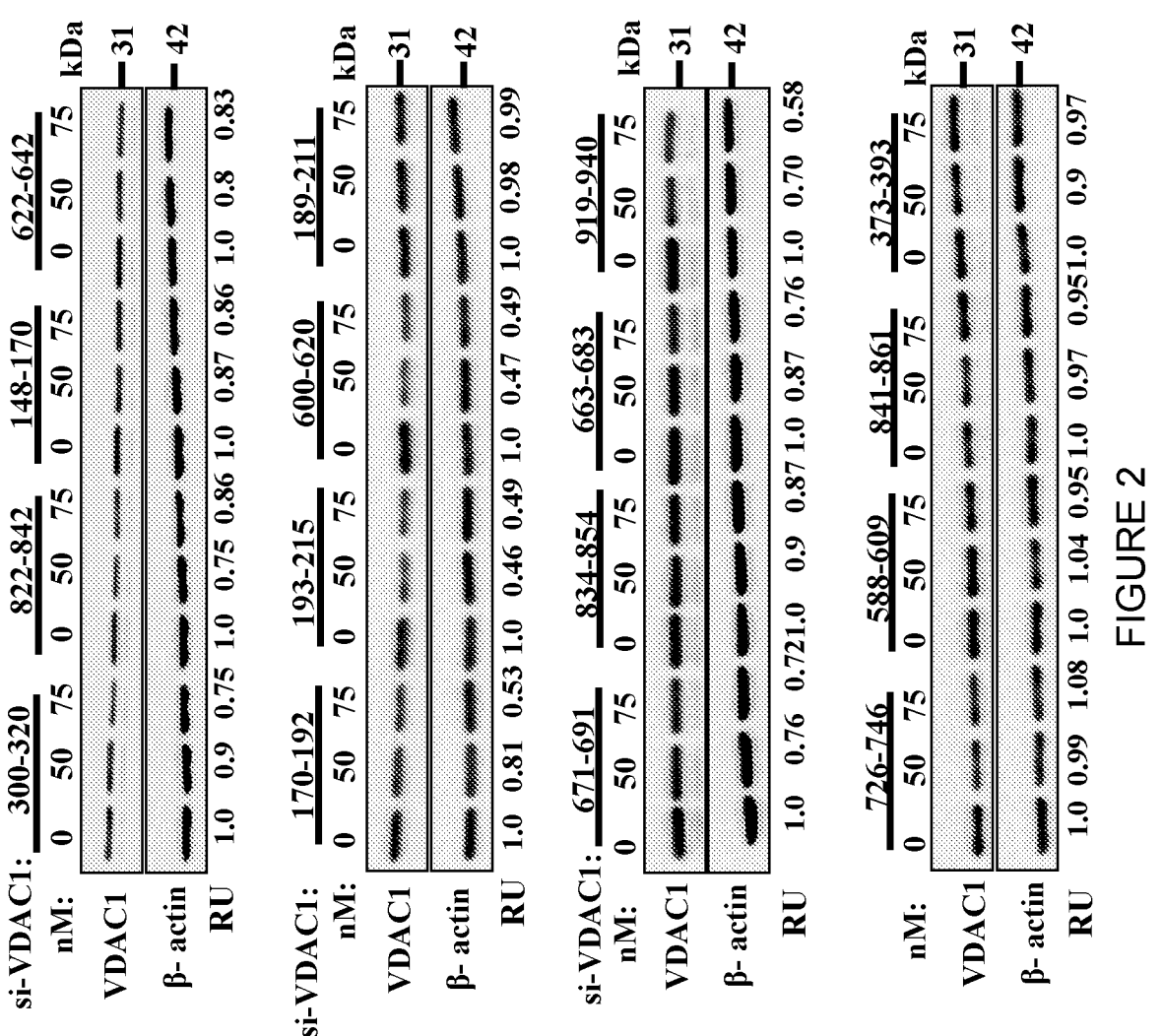
FIG. 2 shows VDAC1 protein expression in A549 lung cancer cells treated with 50 or 75 nM of si-RNA molecules designed to be specific to human VDAC1 (hVDAC1) or to recognize both human and mouse VDAC1 (si-m/hVDAC1).
Figure 2:
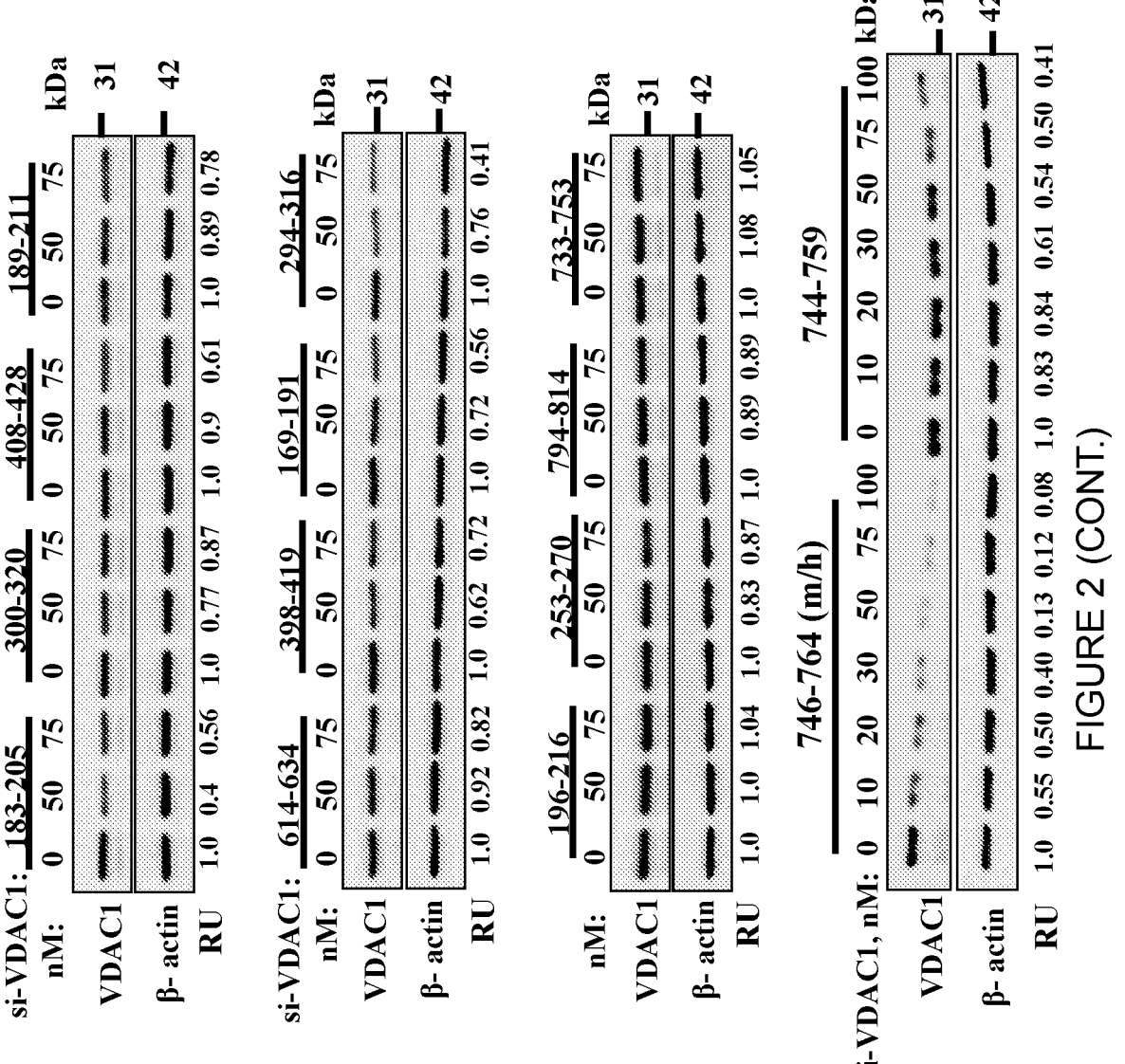

A549 cells were maintained at 37° C. and 5% $CO_2$ in the recommended culture medium and supplements. Cells were transfected with the indicated si-VDAC1 (50 or 75 nM) using JetPRIME as described herein above. 72 h post-transfection, cells were analyzed for VDAC1 expression levels (FIG. 2) and for cell growth using the SRB method as described above (Table 4). The results are presented as % of cell growth relative to control cells treated with si-NT.

TABLE 4

Effect of siRNA molecules targeted to hVDAC1
or m/hVDAC1 on cell proliferation

| siRNA type (Position on VDAC1 transcript) | Sequence | | Cell Growth, % of control | |
|---|---|---|---|---|
| | sense (5'-3') | antisense (5'-3') | 50 nM | 75 nM |
| si-hVDAC1 (148-170) | CUAUGGAUUUGGCUUAA UAAA SEQ ID NO: 30 | UAUUAAGCCAAAUCCAU AGCC SEQ ID NO: 31 | 78.3 | 82.8 |
| si-hVDAC1 (169-191) | GCUUGAUUUGAAAACAA AAUC SEQ ID NO: 32 | UUUUGUUUUCAAAUCAA GCUU SEQ ID NO: 33 | 76.8 | 67.5 |
| Si-m/ hVDAC1 (170-192) | CUUGAUUUGAAAACAAA AUCU SEQ ID NO: 21 | AUUUUGUUUUCAAAUCA AGCU SEQ ID NO: 22 | 62.8 ± 9.6 | 47.8 ± 6.1 |
| si-hVDAC1 (183-205) | CAAAAUCUGAGAAUGGA UUGG SEQ ID NO: 27 | AAUCCAUUCUCAGAUUU UGUU SEQ ID NO: 28 | 43.9 | 47.4 |
| Si-VDAC1 (189-211) | CUGAGAAUGGAUUGGAA UUUA SEQ ID NO: 34 | AAUUCCAAUCCAUUCUC AGAU SEQ ID NO: 35 | 84 | 91.5 |
| si-hVDAC1 (193-215) | GAAUGGAUUGGAAUUUA CAAG SEQ ID NO: 23 | UGUAAAUUCCAAUCCAU UCUC SEQ ID NO: 24 | 60.9 ± 4.2 | 51.3 ± 7.3 |
| si-hVDAC1 (294-316) | CGUUUACAGAGAAAUGG AAUA SEQ ID NO: 25 | UUCCAUUUCUCUGUAAA CGUC SEQ ID NO: 26 | 80.1 ± 5.7 | 52.4 ± 2.6 |
| si-hVDAC1 (300-320) | CAGAGAAAUGGAAUACC GACA SEQ ID NO: 36 | UCGGUAUUCCAUUUCUC UGUA SEQ ID NO: 37 | 91.3 | 73.8 |
| si-hVDAC1 (398-419) | CCUAACACUGGGAAAAA AAAU SEQ ID NO: 38 | UUUUUUUCCCAGUGUUA GGUG SEQ ID NO: 39 | 79.5 | 80.3 |
| Si-m/ hVDAC1 (408-428) | GGAAAAAAAUGCUAAA AUCA SEQ ID NO: 40 | AUUUUAGCAUUUUUUUU CCCA SEQ ID NO: 41 | 92.9 | 72.2 |
| si-hVDAC1 (600-620) | GCUACAAGACUGAUGAA UUCC SEQ ID NO: 42 | AAUUCAUCAGUCUUGUA GCCA SEQ ID NO: 43 | 86.2 | 79.4 |
| si-hVDAC1 (663-683) | CCAUUUACCAGAAAGUG AACA SEQ ID NO: 44 | UUCACUUUCUGGUAAAU GGAG SEQ ID NO: 45 | 83.5 | 86.7 |
| si-hVDAC1 (671-691) | CAGAAAGUGAACAAGAA GUUG SEQ ID NO: 46 | ACUUCUUGUUCACUUUC UGGU SEQ ID NO: 47 | 93 | 96.2 |
| si-hVDAC1 (822-842) | GAUACACUCAGACUCUA AAGC SEQ ID NO: 48 | UUUAGAGUCUGAGUGUA UCCU SEQ ID NO: 49 | 84.7 ± 7.6 | 61.9 ± 3.2 |
| Si- m/hVDAC1 (834-854) | CUCUAAAGCCAGGUAUU AAAC SEQ ID NO: 50 | UUAAUACCUGGCUUUAG AGUC SEQ ID NO: 51 | 100 | 100 |
| Si- m/hVDAC1 (190-209) | CAGAGAAUGGAUUGGAA UUUA SEQ ID NO: 52 | AAUUCCAAUCCAUUCUC UGAC SEQ ID NO: 53 | 86.5 | 77.4 |
| Si-m/ hVDAC1 (614-634) | GAAUUCCAGCUUCAUAC UAAU SEQ ID NO: 54 | UAGUAUGAAGCUGGAAU UCAU SEQ ID NO: 55 | 100 | 77.3 |
| Si-m/ hVDAC1 (622-642) | GCUUCAUACUAAUGUGA AUGA SEQ ID NO: 56 | AUUCACAUUAGUAUGAA GCUG SEQ ID NO: 57 | 93.2 | 88.3 |

TABLE 4-continued

Effect of siRNA molecules targeted to hVDAC1
or m/hVDAC1 on cell proliferation

| siRNA type (Position on VDAC1 transcript) | Sequence | | Cell Growth, % of control | |
|---|---|---|---|---|
| | sense (5'-3') | antisense (5'-3') | 50 nM | 75 nM |
| Si-m/ hVDAC1 (919-940) | CUGGAAUUUCAAGCAUA AAUG SEQ ID NO: 58 | UUUAUGCUUGAAAUUCC AGUC SEQ ID NO: 59 | 82.1 | 72.6 |
| Si-m/ hVDAC1 (794-814) | AAGUGAACAACUCUAGC CUGA SEQ ID NO: 60 | UCAGGCUAGAGUUGUUC ACUU SEQ ID NO: 61 | 95.7 | 79.1 |
| Si-m/ hVDAC1 (253-270) | AACGGCAGCCUGGAAAC CAAG SEQ ID NO: 62 | CUUGGUUUCCAGGCUGC CGUU SEQ ID NO: 63 | 100 | 100 |
| Si-m/ hVDAC1 (733-753) | AACACUCGCUUCGGAAU AGCA SEQ ID NO: 64 | UGCUAUUCCGAAGCGAG UGUU SEQ ID NO: 65 | 100 | 82 |
| Si-m/ hVDAC1 (196-216) | AAUGGAUUGGAAUUUAC CAGC SEQ ID NO: 66 | GCUGGUAAAUUCCAAUC CAUU SEQ ID NO: 67 | 100 | 100 |
| Si-m/ hVDAC1 (588-609) | AACUUCGCAGUUGGCUA UAAG SEQ ID NO: 68 | CUUAUAGCCAACUGCGA AGUU SEQ ID NO: 69 | 90.3 | 88.5 |
| Si-hVDAC1 (841-861) | AAGCCAGGUAUUAAACU GACA SEQ ID NO: 70 | UGUCAGUUUAAUACCUG GCUU SEQ ID NO: 71 | 100 | 100 |
| si-hVDAC1 (373-393) | AAGCUGACCUUCGAUUC AUCC SEQ ID NO: 72 | GGAUGAAUCGAAGGUCA GCUU SEQ ID NO: 73 | 100 | 97 |
| Si- m/hVDAC1 (726-746) | AAACAGUAACACGCGCU UCGG SEQ ID NO: 74 | CCGAAGCGCGUGUUACU GUUU SEQ ID NO: 75 | 67.7 ± 7.5 | 57.9 ± 6.9 |
| Si- m/hVDAC1 (744-759)* | CGGAAUAGCAGCCAAGU UU SEQ ID NO: 76 | AAACUUGGCUGCUAUUC CG SEQ ID NO: 77 | 47.9 ± 4.5 | 42.7 ± 7.1 |
| Si-m/ hVDAC1 (746-764)** | GAAUAGCAGCCAAGUAU CAGtt SEQ ID NO: 3 | UGAUACUUGGCUGCUAU UCtt SEQ ID NO: 4 | 30.9 ± 4.5 | 24.5 ± 3.7 |
| Si-hVDAC12/ A(325-344) | ACACUAGGCACCGAGAU UA SEQ ID NO: 15 | UAAUCUCGGUGCCUAGU GU SEQ ID NO: 16 | 52.9 ± 10.8 | 54.3 ± 4.7 |

TABLE 4: nucleotides derivatized by 2'-O-Me are marked in bold and underline.
*disclosed in WO 2013/012806,
**disclosed in WO 2017/081686.

Example 3: Si-m/hVDAC1 Affect Mesothelioma Cells Growth In Vitro and In Vivo VDAC1 Silencing Reduces Mouse (AB1) and Human (H226) Mesothelioma Cell Growth In Vitro Human (H226) and mouse (AB1) mesothelioma cells were seeded (120,000 cells/well) on six-well dishes separately. Following incubation for 24 h, the cells were transfected with different concentrations (25, 50, 75, 100 nmol/l) of siRNA-m/hVDAC1-B using several transfection reagents (TurboFect, LipidR, GenMute, TurboFect, siLentFect and jetprime). siRNA-m/hVDAC1-B concentration of 50 nM was selected for further experiments, using siLentFect reagent for transfection of murine mesothelioma AB1 cells and jetprime reagent for transfection of human mesothelioma H226 cells.

For time course of VDAC1 silencing, cells were transfected with 50 nM of siRNA-m/hVDAC1-B and VDAC1 expression level was analyzed 36, 48, 72 or 96-hours post-transfection with si-m/hVDAC1-B, cells were washed twice with PBS, harvested and analyzed for VDAC1 expression using specific anti-VDAC1 antibodies.

Figures 3A, 3B:
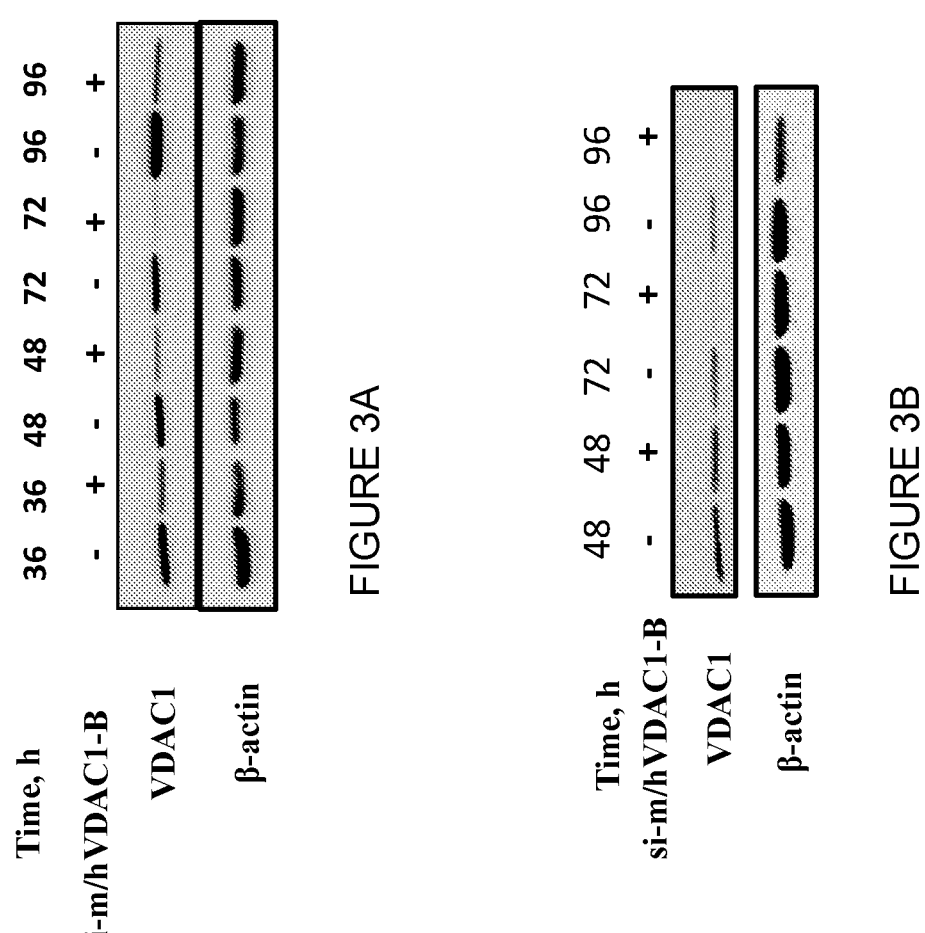
FIG. 3 shows VDAC1 expression in mouse (AB1) (FIG. 3A) and human (H226) (FIG. 3B) mesothelioma cells treated with 50 nM si-m/hVDAC1-B.

FIGS. 3A and 3B show that VDAC1 expression in mouse as well as human mesothelioma cell lines was highly inhibited by the si-m/hVDAC1-B molecule after 72 and 96 h post transfection.

Figure 4:
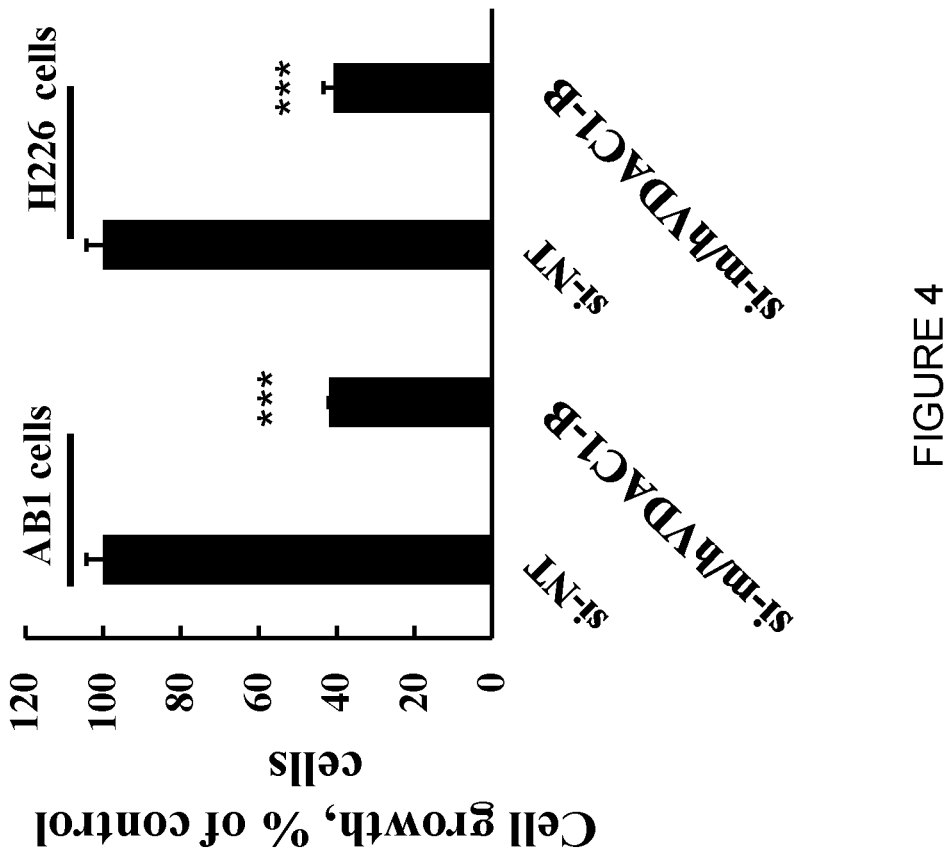
FIG. 4 shows the effect of VDAC1 silencing by si-m/hVDAC1-B on the growth of mesothelioma human (H226) and mouse (AB1) cells in vitro. Non targeted si-RNA (si-NT)

The effect of si-m/hVDAC1-B on cell growth was assayed using the SRB method (FIG. 4). 24-hours post-transfection with si-NT or si-m/hVDAC1-B as described above, cells were washed twice with PBS and fixed with 10% trichloroacetic acid (TCA) for 1-2 hours, and then stained with SRB. SRB was extracted from the cells using 100 mmol/1 Tris base, and absorbance at 510 nm was determined using a plate reader. As is clearly demonstrated in FIG. 4, growth of both human and mouse mesothelioma cell lines was significantly inhibited when the cells were transfected with the si-m/hVDAC1-B molecule compared to cells transfected with siRNA with no specific target.

VDAC1 Silencing Reduces Mouse (AB1) and H226 (Human) Mesothelioma Cell Growth In Vivo Human (H226) and mouse (AB1) mesothelioma cells were subcutaneously inoculated into nude mice and BALB/c mice, respectively. When tumor size reached 50-100 mm$^3$, the mice were divided into matched 2 groups and xenografts were injected intratumorally every 3 days with si-NT (8 mice) or si-m/hVDAC1-B (8 mice) to a final concentration of 50-60 nM.

Figures 5A, 5B:
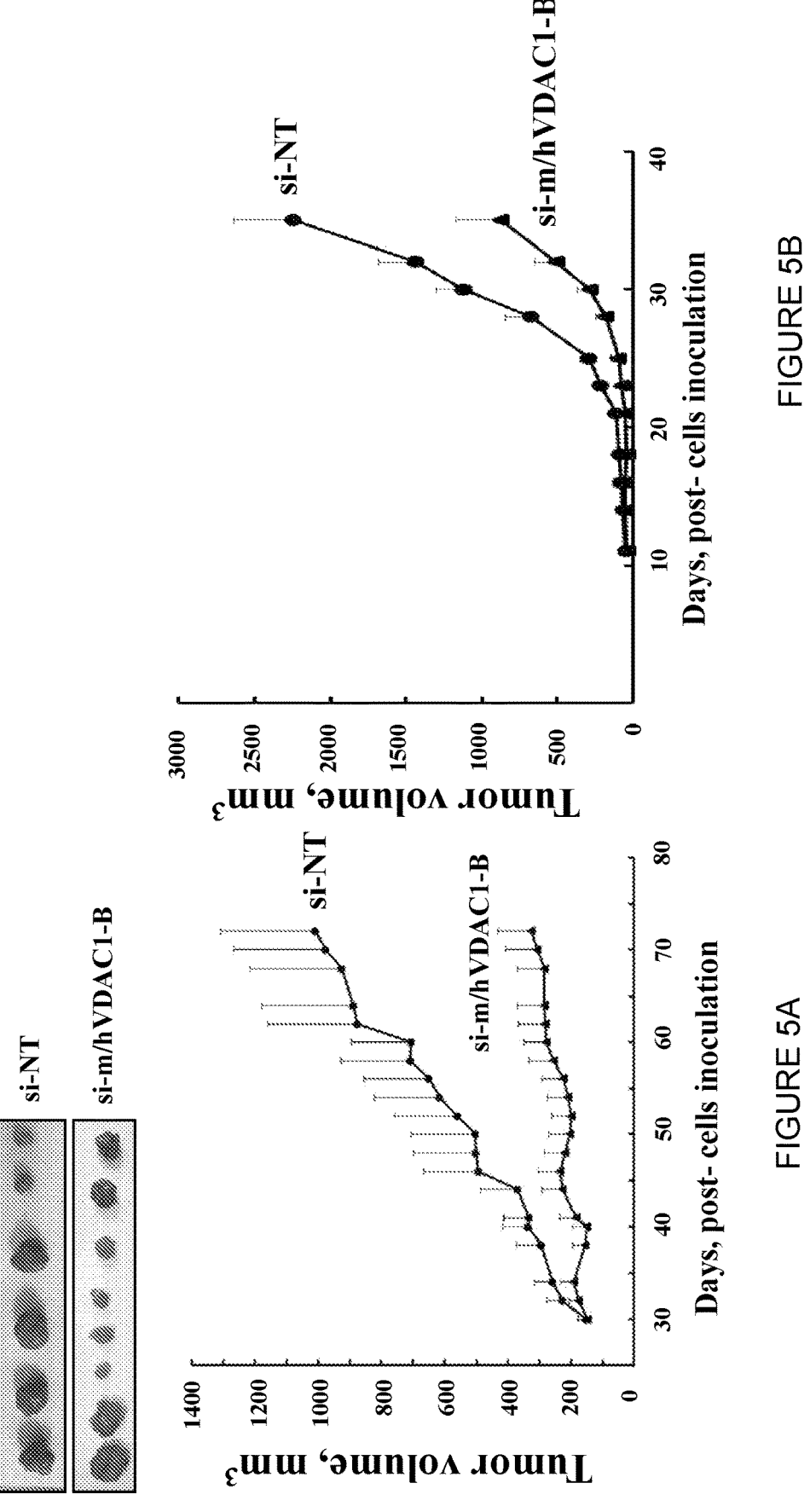
FIG. 5 demonstrates that si-m/hVDAC1-B inhibits tumor growth in vivo. Volume of human (FIG. 5A) and mouse (FIG. 5B) mesothelioma tumors is presented as function of time post-subcutaneous cell inoculation into nude mice. Non targeted si-RNA (si-NT) served as a control.

FIG. 5 shows the calculated average tumor volumes presented as means±SEM for human (FIG. 5A) and mouse (FIG. 5B) mesothelioma tumors, as function of time post-cells inoculation. The H226 cells-derived tumors treated with si-NT– grew linearly with time, and their volume increased about 10-fold in 43 days. However, when treated with si-m/h-VDAC1-B, tumor volume increased only by about 2-fold, pointing to strong inhibition of tumor growth (FIG. 5A). The AB1 cells-derived tumor volume increased exponentially, by about 40-fold, 25 days post-cells inoculation (FIG. 5B). si-m/h-VDAC1-B delayed tumor growth and the tumor volume increased only by about 13-fold after 25 days. The results show that in the synegeneic model (mouse cells into mouse) the tumor grows faster and reach larger volume than in the xenograft model (human cells into nude mice). Nevertheless, significant reduction of the tumor volume in the presence of si-m/hVDAC1-B was observed in both models.

Figures 6A, 6B:
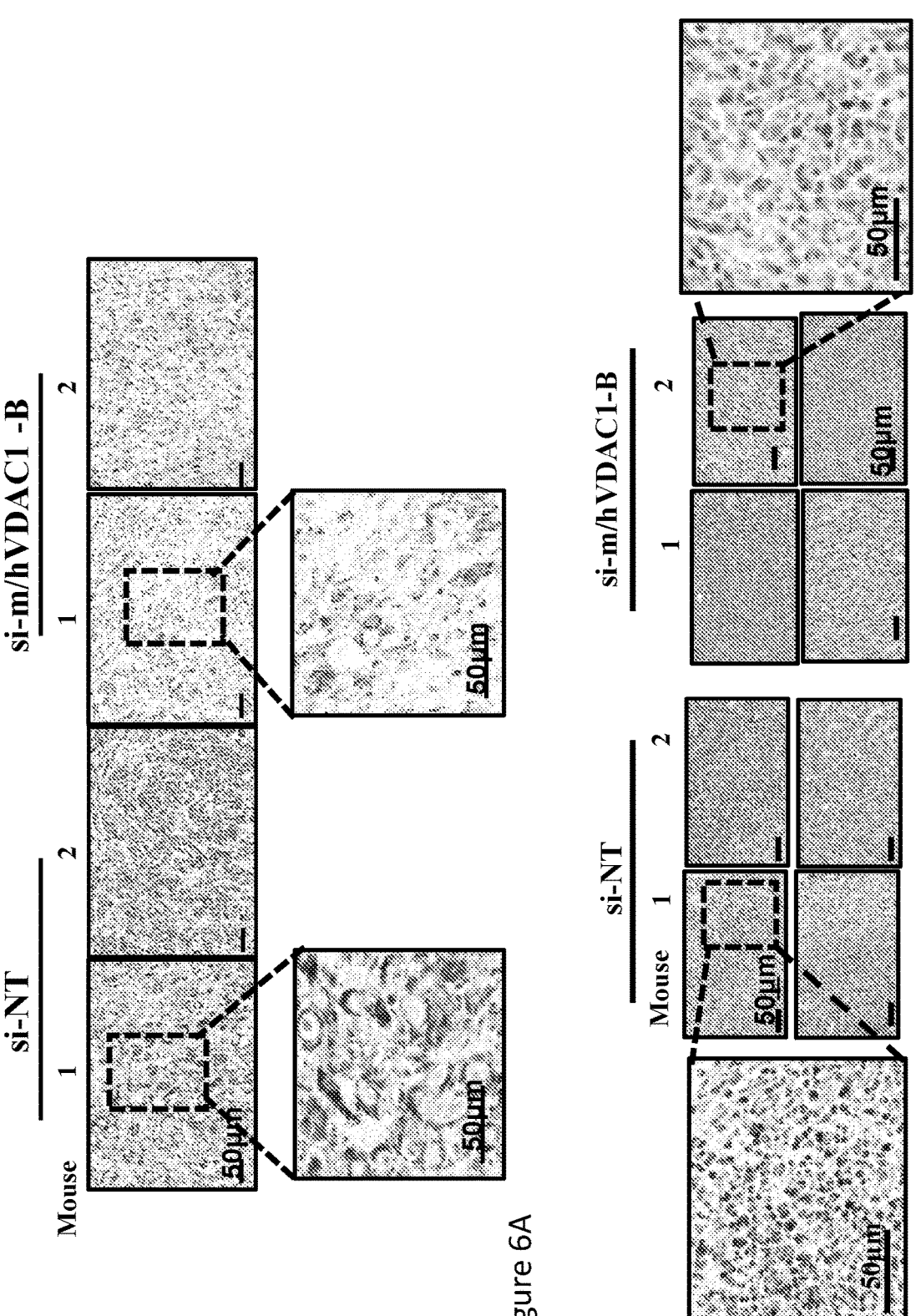
FIG. 6 shows representative IHC staining of sections derived from H226 (FIG. 6A) and AB1 (FIG. 6B) mesothelioma xenografts, treated with si-NT or si-m/h-VDAC1-B, stained for VDAC1 using specific antibodies.

FIG. 6 shows representative IHC staining of sections derived from xenograft tumors of human mesothelioma H266 cells (FIG. 6A) and murine mesothelioma AB1 cells (FIG. 6B), treated with si-NT or si-m/hVDAC1-B, stained for VDAC1 using specific antibodies. The results show that si-m/h-VDAC1-B silenced VDAC1 expression in both tumors, but the level of VDAC1 silencing in the cells derived from mouse-AB1 xenograft was lower than the silencing level observed in cells of the human H226-derived tumors. These results are concomitant with the more significant growth inhibition of human H226-derived tumors, showing that more significant inhibition of VDAC1 expression results in higher inhibition of tumor growth.

Figure 7:
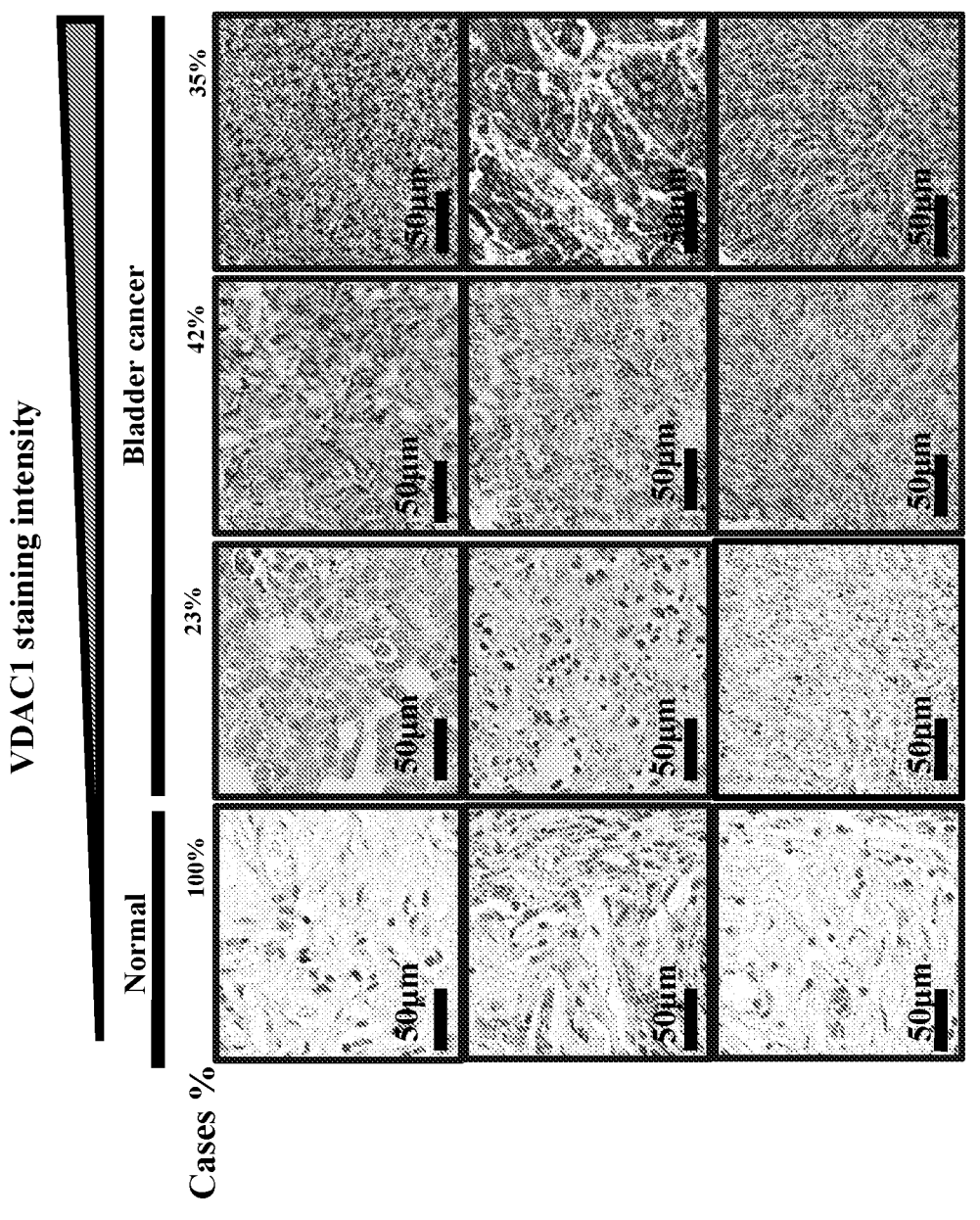
FIG. 7 shows IHC staining of VDAC1 in human healthy tissue (n=10), and of bladder cancer tissues comprising transitional cell carcinoma (n=35 patients); squamous cell carcinoma (4 patients); and adenocarcinoma (1 patients) in microarray slide (Biomax). The number in each lane represents the percentage of patient samples that stained at the relative intensity presented by a gradient line on the top.

Example 4: Bladder Cancer Express Very High Levels of VDAC1 and Si-m/hVDAC1—Affect Bladder Cancer Cell Growth In Vitro VDAC1 expression levels analyzed in tumor sections obtained from 40 patients with bladder cancer and in 10 sections obtained from healthy tissue, clearly show that VDAC1 is highly expressed in all patients relative to healthy tissues (FIG. 7).

Figures 8A, 8B, 8C:
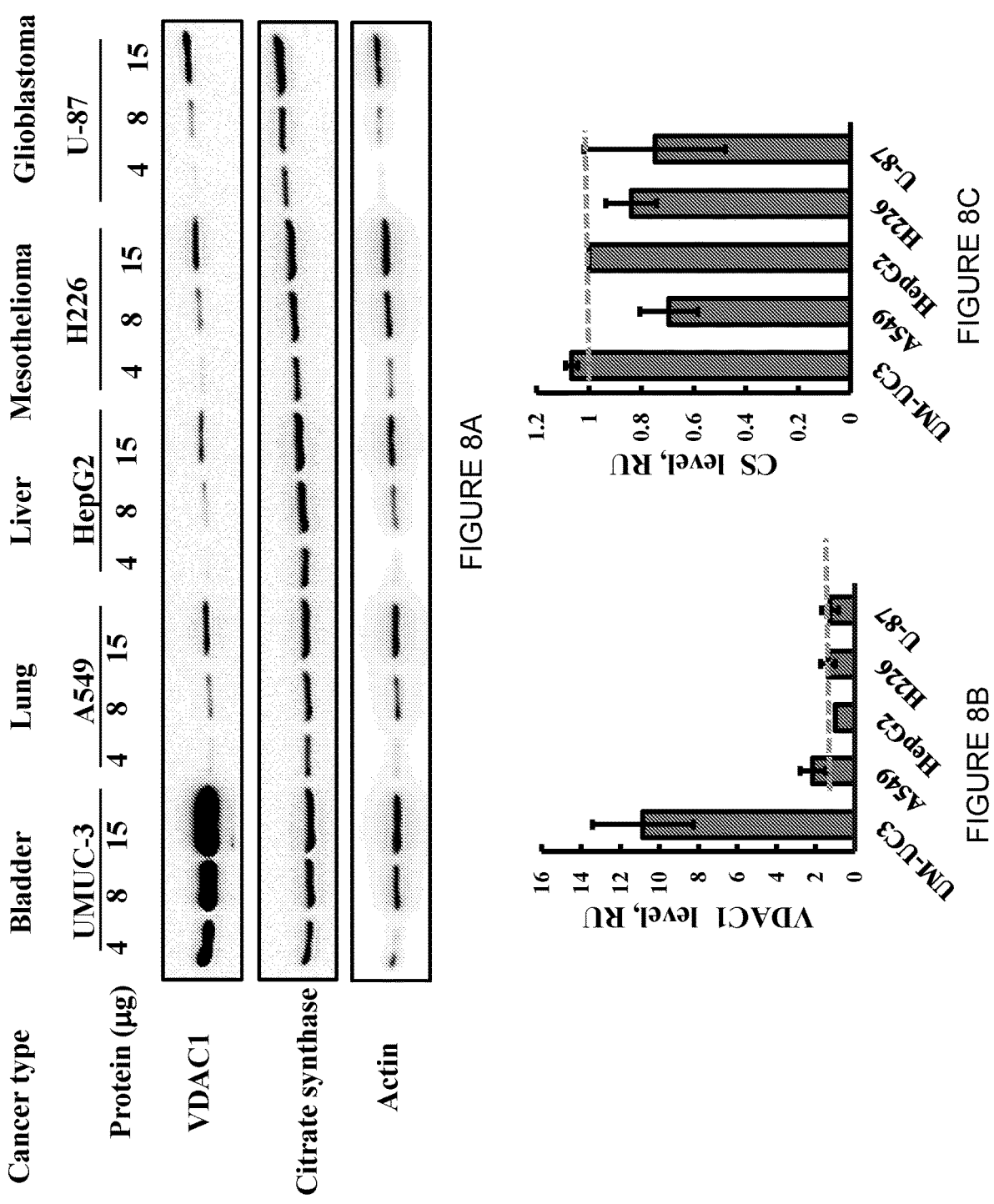
FIG. 8A shows VDAC1 levels analyzed at 3 different protein concentration in various cancer cell lines by immunoblotting.
FIG. 8B show quantitative analysis of VDAC1 and FIG. 8C of citrate synthase (CS) expression levels presented as relative unit (RU).

FIG. 8A-C shows that VDAC1 is highly expressed in bladder cancer cell line. VDAC1 expression at 3 different total protein concentrations was examined by immunoblotting in various human cancer cell lines (UMUC-3, bladder cancer; A549-lung cancer; HepG2, liver cancer; H226-mesothelioma; U-87MG, glioblastoma). It is clearly shown the bladder cancer cell line, UMUC3 expresses the highest levels of VDAC1 being about 10-fold higher than in the other cancer cell line. The expression levels of citrate synthase and actin in the same samples was also examined (FIG. 8A). FIG. 8B and FIG. 8C show quantitative analysis of VDAC1 and citrate synthase expression levels presented as relative unit (RU). The increase in the expression level of VDAC1 in UMUC3 cells but not of citrate synthase (CS) suggests that the observed increase in VDAC1 is per mitochondrion and is not a result of an increase in the number of mitochondria.

Interestingly, although cancer cells and tumors express high levels of VDAC1, (Shoshan-Barmatz V, et al. Biochim Biophys Acta. 2015. October; 1848(10 Pt B):2547-75), bladder tumors and cell line as UMUC-3, express the highest level of VDAC1.

Figure 8D:
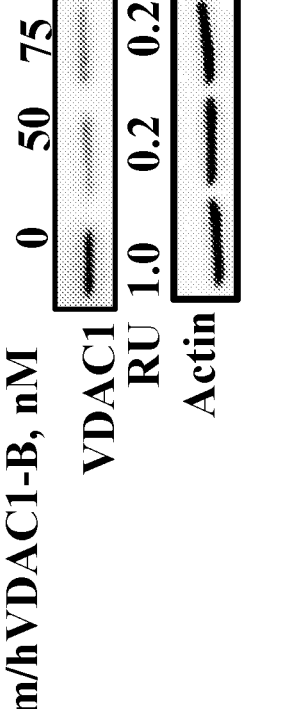
FIGS. 8D and 8E show UMUC-3 cells treated with 50 or 75 nM si-m/hVDAC1-B and analyzed 72 h post treatment with si-m/hVDAC1-B for VDAC1 levels by immunoblotting (FIG. 8D) and cell growth using the SRB assay (FIG. 8E) (mean±SEM; n=3).
Figure 8E:
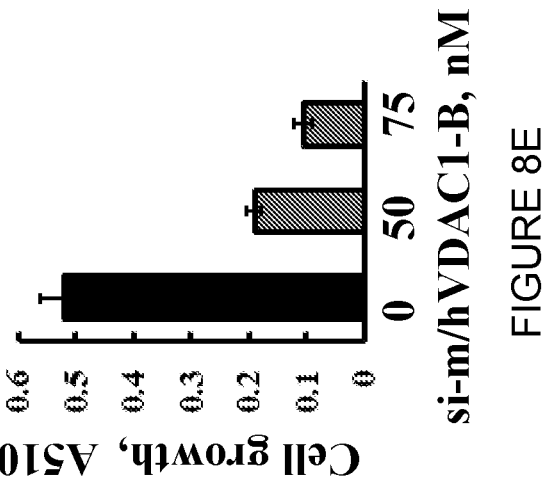

UMUC-3 bladder cancer cells were treated with 50 or 75 nM si-m/hVDAC1-B. 72 h post-treatment the cells were analyzed for VDAC1 levels by immunoblotting (FIG. 8D) and cell growth using the SRB assay (FIG. 8E) (means±SEM; n=3). The decrease in VDAC1 expression was concomitant with a decrease in the bladder cancer cell growth, indicating that the siRNA molecule may be effective in treating bladder cancer.

Example 5: Si-m/hVDAC1 is Effective in Treating Urethane-Induced Lung Cancer in A/J Mice A/J mice are widely used to model cancer and for carcinogen testing given their high susceptibility to carcinogen-induced tumors. Urethane caused tumors in several rodent species at several different tissue sites and by several different routes of exposure. It was found to be carcinogenic following administration of a single dose and by prenatal exposure. Malignant and/or benign tumors of the lung, liver, and blood vessels were seen in many studies, along with lymphoma, leukemia, or melanoma.

In this study urethane was used to induce lung cancer essentially as described in Redente, E F et al. (Redente, E F et al., 2007. The American Journal of Pathology 170(2):693-708). The protocol of lung cancer induction in A/J mice is described in FIG. 9.

After the establishment lung tumors, about 22-23 weeks after urethane injection, 200 nM of si-m/h-VDAC1-B (n=8) or of the non-targeted control siRNA (si-NT, n=7) as a control encapsulated within PEI-PLGA-based nanoparticles (Das J, et al., 2014, ibid), or with the free silencing molecule, were injected i.v. to the mice 2 times a week for 20 weeks. Then mice were sacrificed and thereafter lungs were removed, fixed and paraffin-embedded and H & E stained or immune-stained with specific antibodies.

As is demonstrated in FIG. 10, i.v. administration of urethane at 1 mg/g mouse body weight (BW) induced the formation of lung cancer. The majority of the cancer cells had the appearance of non-small cell lung cancer (FIG. 10B(I)), but small cell carcinoma could also be observed (FIG. 10B(II), and its enlargement presented in FIG. 10C-D). Small lung cancer cells are composed of diffuse sheets of small malignant cells with scant cytoplasm and finely granular nuclear chromatin (Travis, W D. 2012. Modern Pathology 25:S18-S30).

Figures 11A, 11B:
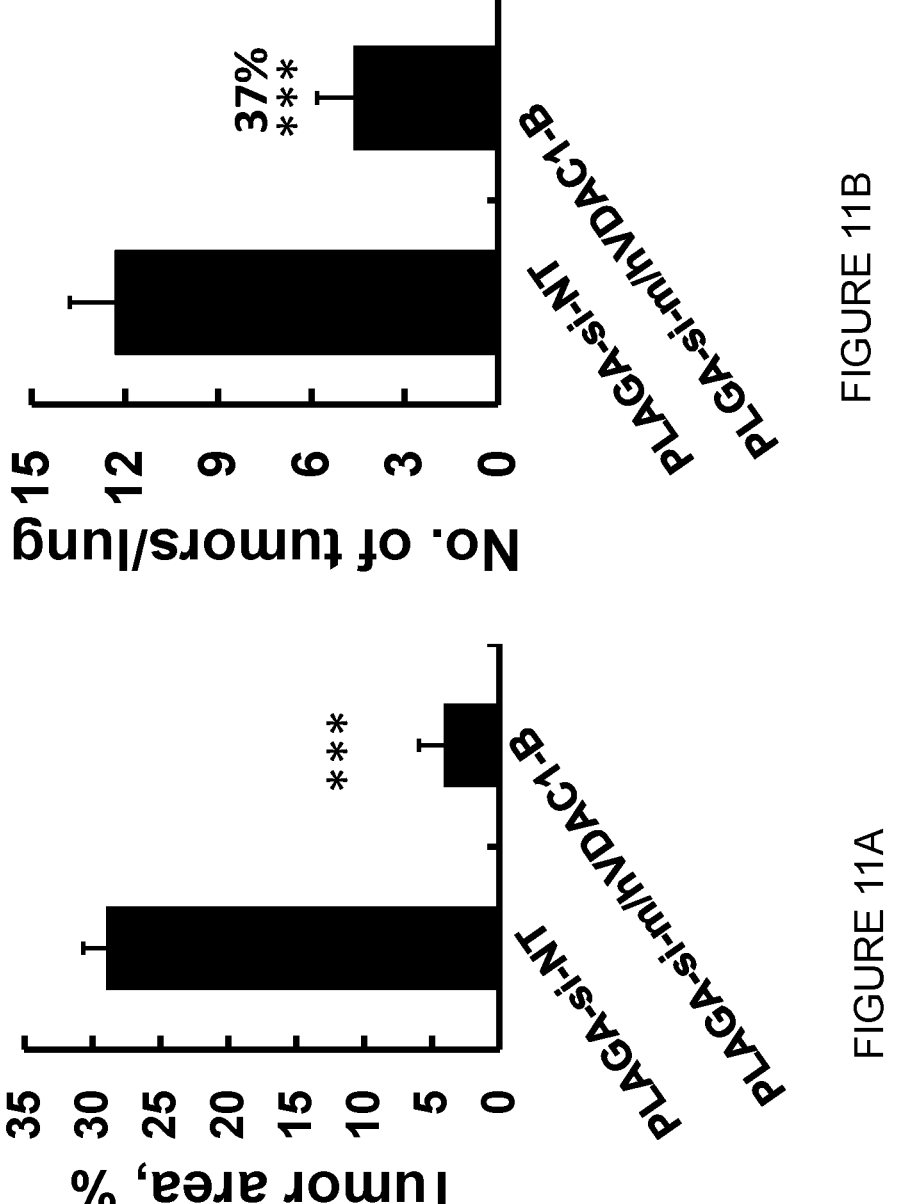
FIG. 11 shows tumors area (FIG. 11A) and number of tumors per lung (FIG. 11B) of urethane-induced lung tumors in A/J mice treated with encapsulated si-m/hVDAC1-B (PLGA-si-m/hVDAC1-B) or with the control si-NT (PLGA-si-NT).

H&E staining allows tumors identification and the tumor area and number per lung were measured. Tumor area (FIG. 11A) and number of tumor per lung (FIG. 11B) were reduced by 86% and 63% in mice that received PEI-PLGA-si-m/hVDAC1-B, respectively, in relative to mice treated with PEI-PLGA-si-NT.

Figure 12:
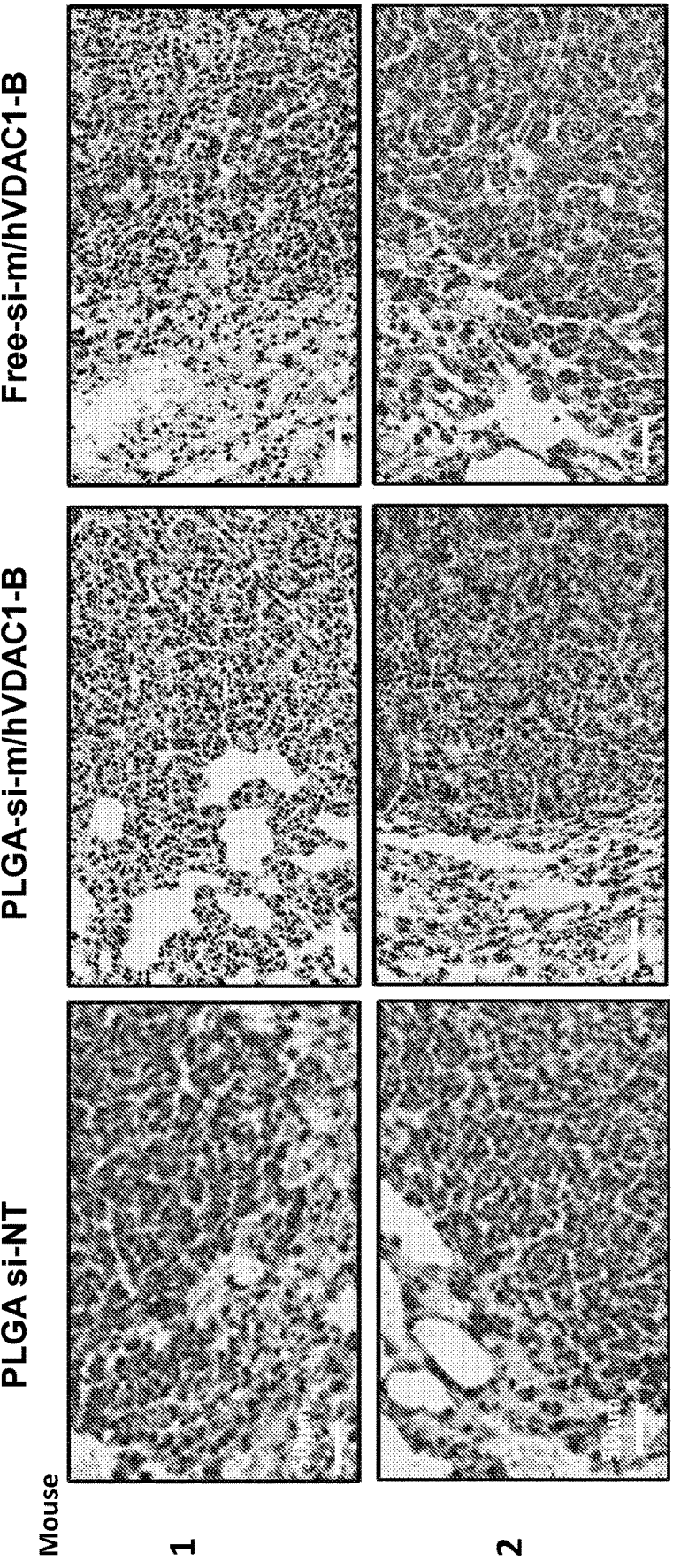
FIG. 12 shows VDAC1 expression in urethane-induced lung tumors in A/J mice treated with encapsulated si-m/hVDAC1-B (PLGA-si-m/hVDAC1-B), free si-m/hVDAC1-B or with the control encapsulated si-NT (PLGA-si-NT).

VDAC1 expression level was evaluated in lung sections obtained from mice treated with PEI-PLGA-si-m/hVDAC1-B, PEI-PLGA-si-NT, or free si-m/hVDAC1-B, using specific antibodies (FIG. 12). The results show that the tumors treated with PEI-PLGA-si-NT or with free si-m/hVDAC1-B express high levels of VDAC1, that were highly reduced in lung sections from PEI-PLGA-si-m/hVDAC1-B treated mice. The effect of the encapsulated VDAC1 silencing molecule resulted in significant lower staining of VDAC1, indicating that it was protected in the blood, translocation to the lung and reaching its cellular target. Further experiments were therefore performed with the encapsulated si-m/h-VDAC1-B.

Figures 13A, 13B:
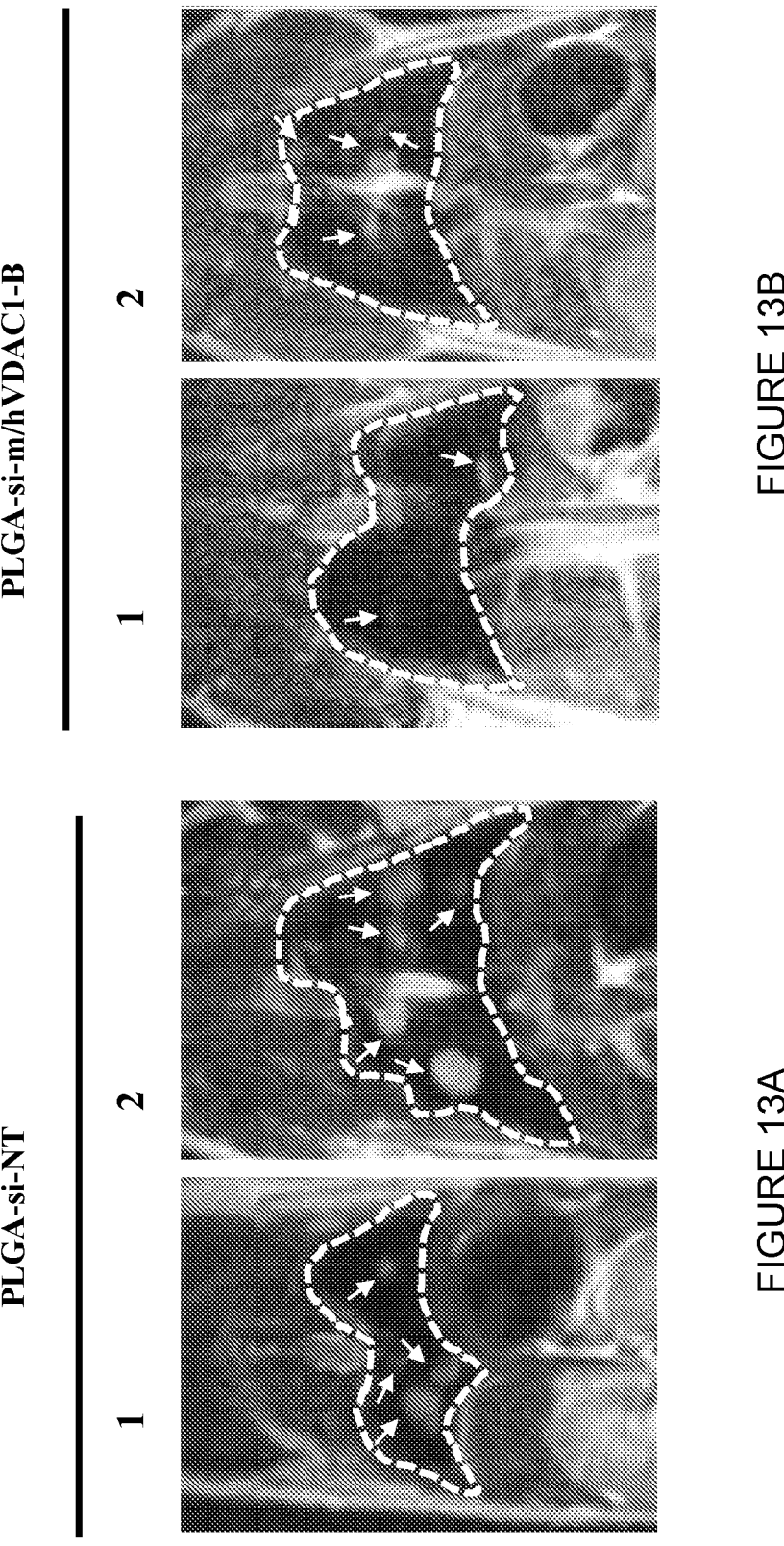
FIG. 13 A-B shows representative MM images of mice subjected to treatment with encapsulated si-NT (PLAG-si-NT, FIG. 13A) or si-m/hVDAC1-B (PLAG-si-m/hVDAC1-B, FIG. 13B) via i.v. administration. The lungs are labeled by dashed lines and arrows point to tumors.
Figure 13D:
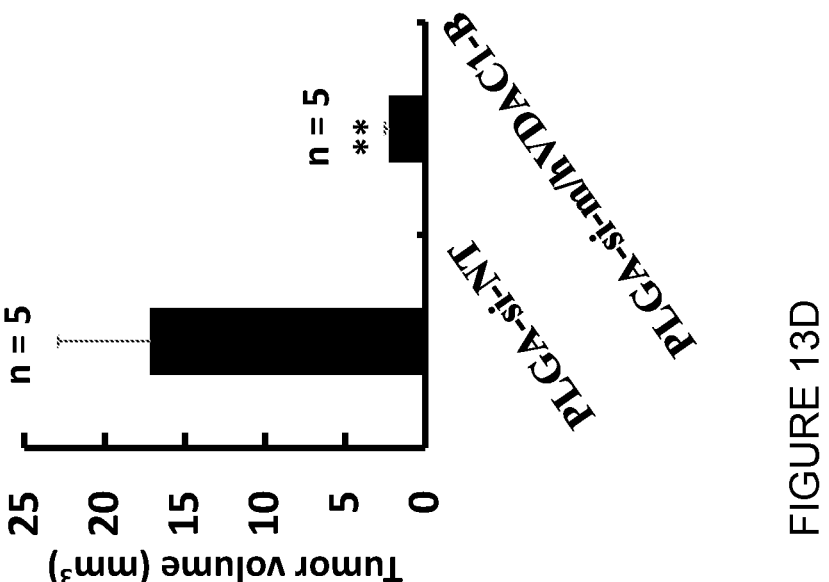
Figure 13C:
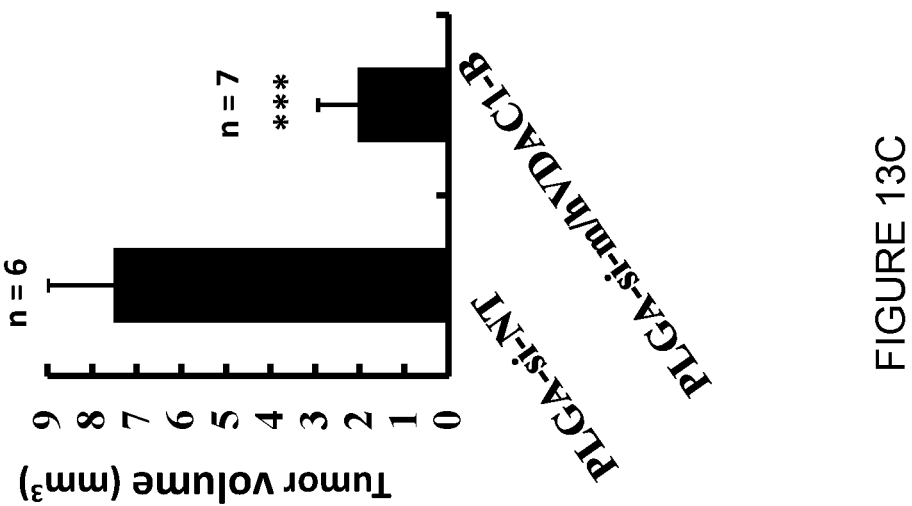

In another experiment, the effect of VDAC-1 silencing by the PEI-PLGA-si-m/h-VDAC1-B molecule on the urethane-induced lung tumors was further demonstrated by MRI imaging. FIG. 13A and FIG. 13B show representative MRI images of lungs of mice subjected to PEI-PLGA-si-NT or PEI-PLGA-si-m/hVDAC1-B treatment (i.v.), respectively. Quantitative analysis of the volume of tumors from the MRI images of the PEI-PLGA-si-NT- and PEI-PLGA-si-m/hV-DAC1-B-treated mice, analyzed after 31 (FIG. 13C) and 34 (FIG. 13D) weeks from urethane treatment, show significant reduction in the tumor volume in the PEI-PLGA-si-m/h-VDAC1-B-treated mice. Results=means±SEM (n=5-7), ($P \leq 0.01$, *$P \leq 0.001$).

The effect of silencing VDAC1 expression by PEI-PLGA-si-m/hVDAC1-B on the tumor cells was examined by analyzing the expression levels of the cell proliferation factor Ki-67 and on the metabolism associated enzymes hexokinase-1 (HK1) and glucose transporter 1 (Glut1).

Figures 14A, 14B:
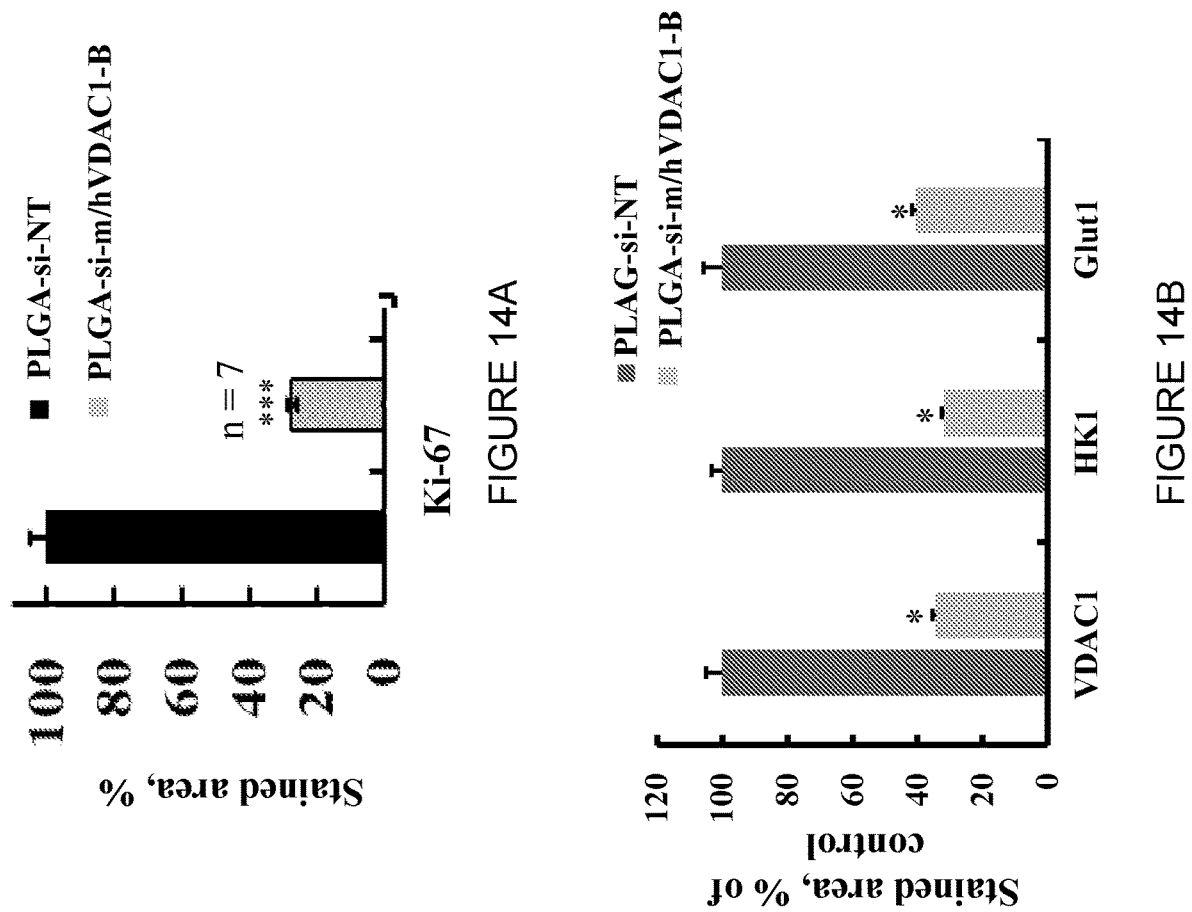
FIG. 14 shows quantitative analysis, using a Panoramic microscope, of immuno-stained tumor sections from representative lung sections obtained from mice treated with encapsulated si-NT (PLGA-si-NT) or with encapsulated si-m/hVDAC1-B (designated PLGA-si-m/hVDAC1-B) using specific Ki-67 antibodies (FIG. 14A), and using anti-VDAC1, anti-HK1 and anti-Glut1 specific antibodies (FIG. 14B). Results of FIG. 14A are the means±SEM (n=7), (*P≤0.001). Results of FIG. 14**B are the means±SEM (n=3), (*P≤0.05).

FIG. 14 shows quantitative analysis, using a Panoramic microscope, of immuno-stained tumor sections from representative lung sections obtained from mice treated with PEI-PLGA-si-NT or with PEI-PLGA-m/h-si-VDAC1-B using specific Ki-67 antibodies (FIG. 14A), and using VDAC1, HK1 and Glut1 specific antibodies (FIG. 14B). Staining intensity at the lungs from PLAG-si-NT-treated mice was considered as 100%. Results of FIG. 14A are the means±SEM (n=7), (*$P \leq 0.001$). Results of FIG. 14**B are the means±SEM (n=3), (*$P \leq 0.05$).

Reduction of VDAC1 expression was associated with significant reduction in the expression of the cell proliferation marker Ki-67 as well as of the metabolic enzymes HK-1 and the transporter Glut1, suggesting metabolic reprograming in the tumor cells as induced by VDAC1 depletion and leading to inhibited cell proliferation.

Figures 15A, 15B, 15C:
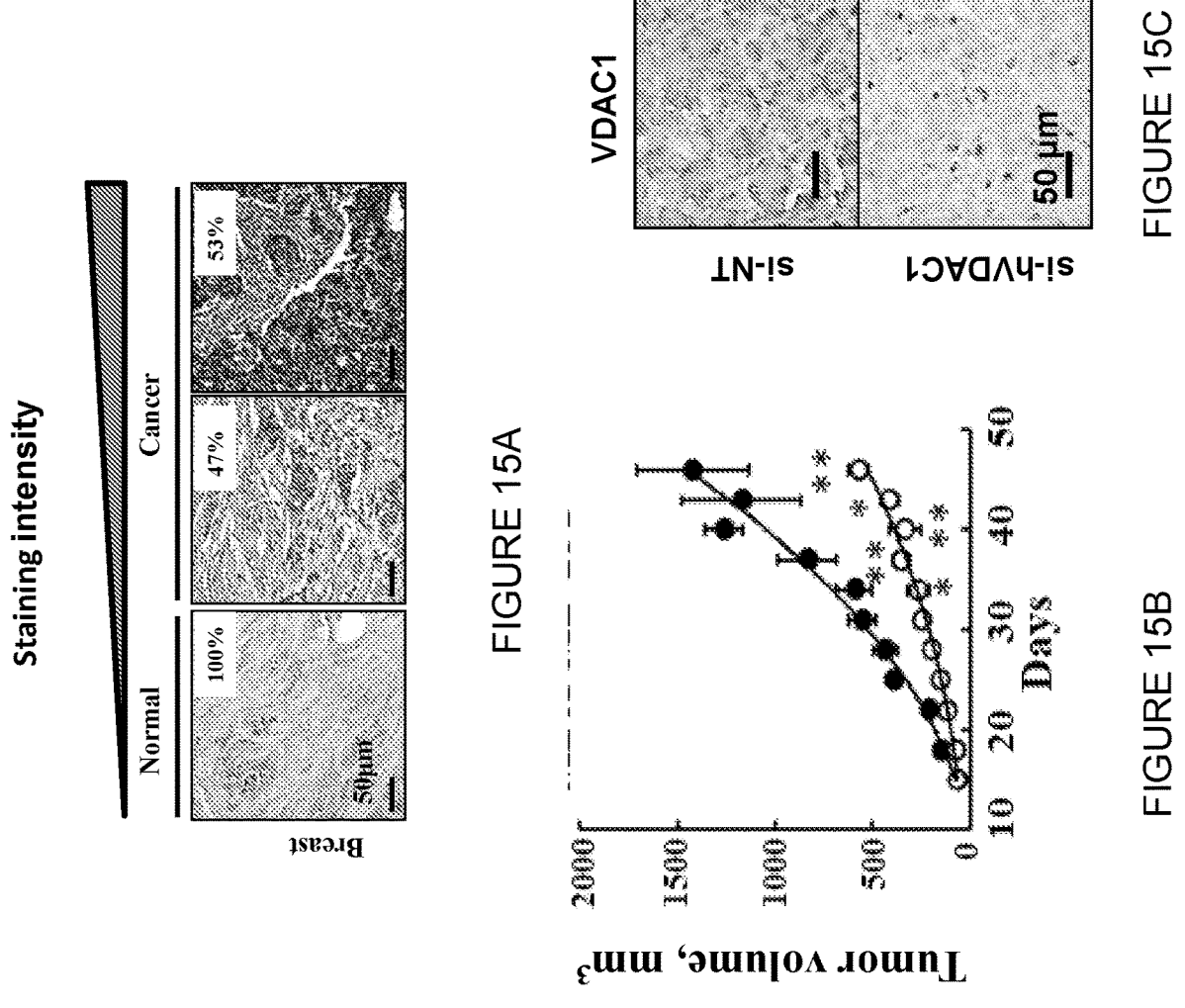
FIG. 15A shows immunohistochemistry (IHC) staining of VDAC1 in human normal cells (n=13) and breast cancer (n=20) in tissue microarray slides (Biomax). Percentages of sections stained at the indicated intensities are shown.
FIG. 15B shows calculated average tumor volumes presented as means±SEM. MDA-MB-231 cells were subcutaneously inoculated into nude mice. When tumor size reached 50-100 mm$^3$, the mice were divided into matched 2 groups and xenografts were injected intratumorally every 3 days with si-NT (●, 8 mice) or si-hVDAC1 (○, 8 mice) at a final concentration of 50-60 nM.
FIG. 15C and FIG. 15D show immuno-staining of VDAC1. Sections of si-NT-treated tumors (TT) and si-hVDAC1-TT from MDA-MB-231 xenograft mice were stained for VDAC1 by IHC (15C) or immunoblot (15D), using specific antibodies. RU=average relative unit of VDAC1 staining in si-hVDAC1-TTs (n=4) relative to the staining in si-NT-TTs (n=3). β-actin served as an internal loading control.
Figure 15D:
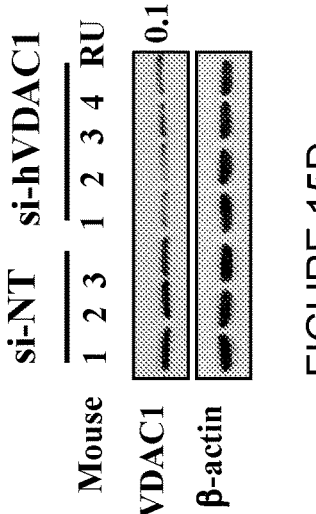
Figure 15F:
FIG. 15F show quantitative analyses of Ki-67-positive cells in MDA-MB-231-derived tumors. Results show the mean±SEM (n=5), p*≤0.05; p**≤0.01.
Figure 15E:
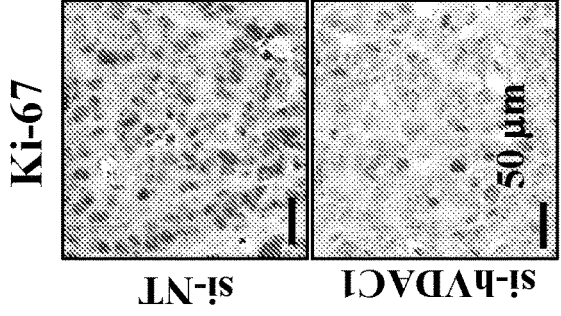
FIG. 15E is micrographs of representative IHC staining of si-NT-TTs and si-hVDAC1-TTs derived from MDA-MB-231 cells with anti-Ki-67 antibodies.

Example 6: Si-hVDAC1 Affects Triple-Negative Breast Cancer Cells In Vitro and In Vivo As VDAC1 was over-expressed in patient-derived breast cancer samples (FIG. 15A). The effect of si-hVDAC1 on sub-cutaneous (s.c) tumor xenografts derived from MDA-MB-231, established in athymic nude mice was tested. After development of the tumor, the inventors separated the mice into two matched groups, injected them intratumorally every 3 days with si-NT or si-hVDAC1-2A (comprising SEQ ID NO:15 and SEQ ID NO:16 to a final concentration of 50 nM, and followed their tumor growth. In si-NT-treated tumors (si-NT-TT), tumor volume was increased by 22-fold. However, the growth of si-hVDAC1-treated tumors (si-hV-DAC1-TTs) was inhibited (FIG. 15B). After the mice were sacrificed, the tumors were excised and either frozen or fixed in formalin, and sections were IHC-stained for VDAC1 expression. si-NT-TTs were strongly immuno-stained, while, as expected, si-hVDAC1-TTs staining was very weak (FIG. 15C). Similar results were obtained by immunoblotting (FIG. 15D), where decreased VDAC1 levels (80-90%) were observed. Treating the tumors with si-hVDAC1-2A also decreased the expression of the cell proliferation marker Ki-67 by about 70-80% as shown by IHC staining (FIG. 15E) and quantitative analysis (FIG. 5F).

Figure 16A:
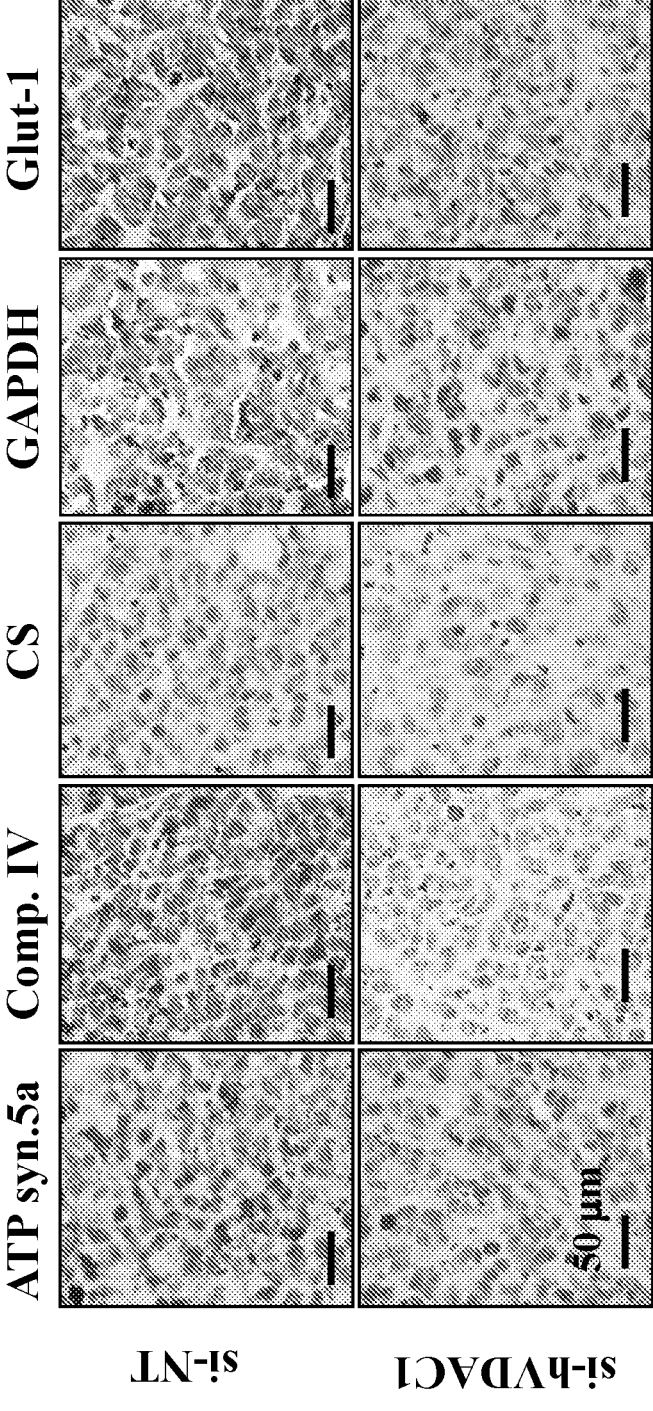
FIG. 16A is a representative IHC staining using specific antibodies against glucose transporter 1 (Glut1), glyceraldehyde dehydrogenase (GAPDH), citrate synthase (CS), electron transfer complex IV (Comp. IV) and ATP synthase 5a (ATPsyn.5a) from sections derived from MDA-MB-231 xenograft tumors treated with si-NT or si-hVDAC1.
Figure 16C:
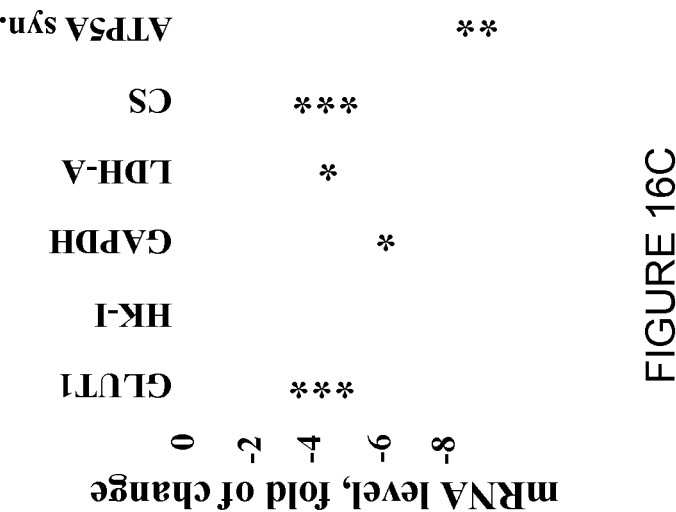
FIG. 16C shows mRNA levels of metabolic enzymes in si-hVDAC1-TTs, relative to those in si-NT-TTs derived from MDA-MB-231 tumors, represented as fold change. Results are means±SEM (n=5 tumors for each), p*≤0.05; p≤0.01; p*≤0.001.
Figure 16B:
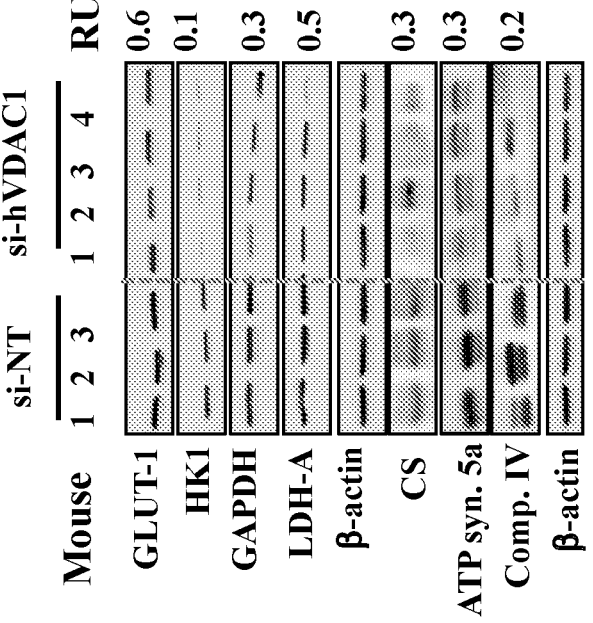
FIG. 16B shows immunoblot of selected metabolism-related proteins from sections of MDA-MB-231 xenograft tumors treated with si-NT or si-hVDAC1. Quantitative analysis is presented as average of the staining intensity in si-hVDAC1-TTs relative to si-NT-TTs presented in relative units (RUs). β-actin served as an internal loading control.

Example 7: VDAC1 Depletion by siRNA Reversed Reprogramed MDA-MB-231 Cancer Cell Metabolism and Eliminated Cancer Stem Cells The metabolic alterations seen during malignant transformation involved a spectrum of functional aberrations and mutations which contributed to elevated glycolysis and increased expression levels of glucose transporters (Glut-1) and glycolytic enzymes (FIG. 16). IHC of si-hVDAC1-treated tumors derived from MDA-MB-231 cells showed dramatic decreases of Glut-1 and glyceraldehyde dehydrogenase (GAPDH) levels, as compared to si-NT-TTs (FIG. 16A). Similar results were obtained for the above proteins and hexokinase (HK-I) and lactate dehydrogenase-A (LDH-A) by immunoblotting (FIG. 16B) and qRT-PCR (FIG. 16C). Expression levels of the Krebs cycle enzyme citrate synthase (CS), the mitochondrial electron transport complex IVc (Comp. IV), and ATP synthase 5a (ATPsyn5a) were also highly reduced in si-hVDAC1-TTs, as analyzed by IHC (FIG. 16A), immunoblotting (FIG. 16B) or qRT-PCR (FIG. 16C), consistent with alterations in oxidative phosphorylation (OXPHOS). The decreased expression of Krebs cycle and OXPHOS enzymes also agrees with the concept that cancer cells combine glycolysis and mitochondria to produce energy, according to normoxic or hypoxic conditions.

Figure 17A:
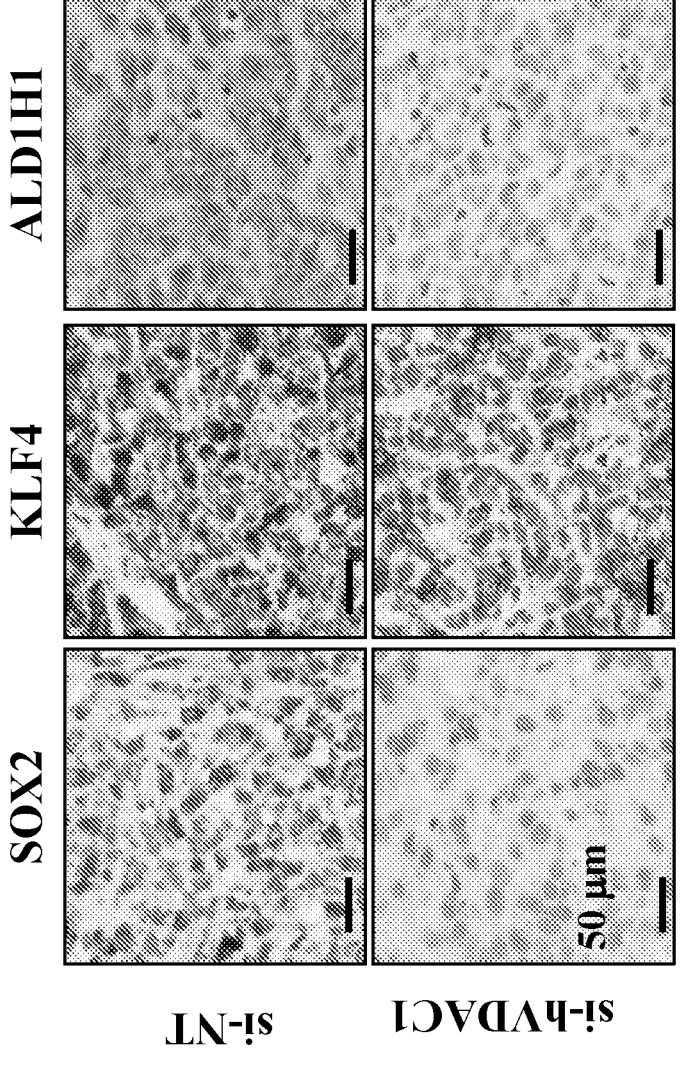
FIG. 17A shows representative IHC staining with cell line-specific CSC markers using specific antibodies in sections derived from MDA-MB-231 xenograft tumors treated with si-NT or si-hV-DAC1.
Figures 17B, 17C:
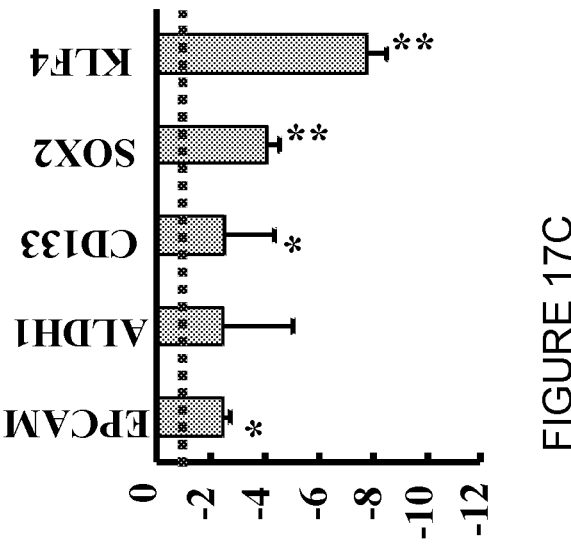
FIG. 17B shows an immunoblot analysis of protein extracts obtained from MDA-MB-231 xenograft tumors treated with si-NT or si-hVDAC1, using the specific antibodies indicated. Quantitative analysis of immunoblots is presented as average relative units (RU) (staining intensity in si-hVDAC1-TTs (n=4) relative to the staining in si-NT-TTs, (n=3), and β-actin as an internal loading control is shown.
FIG. 17C shows mRNA levels of the indicated genes in si-hVDAC1-TTs relative to those in si-NT-TTs of MDA-MB-231 derived tumors. Results are means±SEM (n=5 tumors), p*≤0.05; p**≤0.001. Dashed line indicates the control level.

The effects of VDAC1 silencing on cancer stem cells (CSCs) was analyzed by following the expression of CSC-associated markers specific to MDA-MB-231 cells (FIG. 17). In tumors derived from MDA-MB-231 breast cancer cells and treated with si-hVDAC1-2A, the expression of ALDH1, KLF4, SOX2, CD133 and EPCAM were highly reduced, as analyzed by IHC (FIG. 17A), Western blot with specific antibodies (FIG. 17B) or qRT-PCR (FIG. 17C), showing decrease in the CSC markers expression of about 3-8-fold.

Example 8: Effect of VDAC1-Silencing on Triple-Negative Breast Cancer Cells

MDA-MB-231 human breast cancer cells correspond to a poorly differentiated triple negative breast cancer (TNBC) cell line that does not express the progesterone and estrogen receptors or the receptor tyrosine-protein kinase erbB-2 (ERBB2/Her2). Altered cancer metabolism could affect cell differentiation, and the possibility that VDAC1 silencing may derive MDA-MB-231 cells to differentiation was analyzed by monitoring the expression of several markers proposed as reflecting differentiation.

Figure 18A:
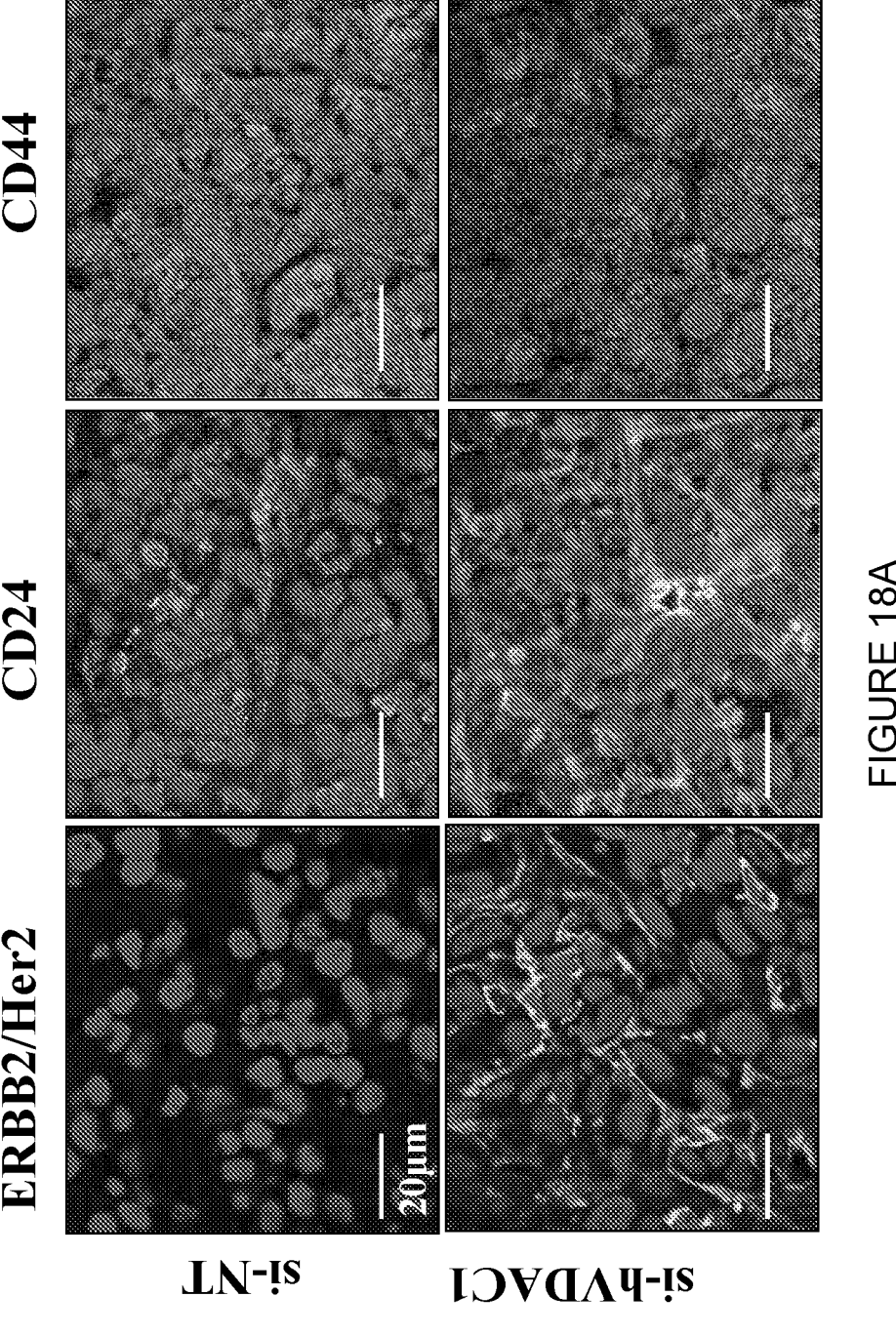
FIG. 18A show immuno-fluorescence (IF) staining of MDA-MB-231 cell-derived hVDAC1-TTs or si-NT-TTs stained with anti-CD44, anti-CD24 or anti-ERBB2/Her2 antibodies.
Figure 18B:
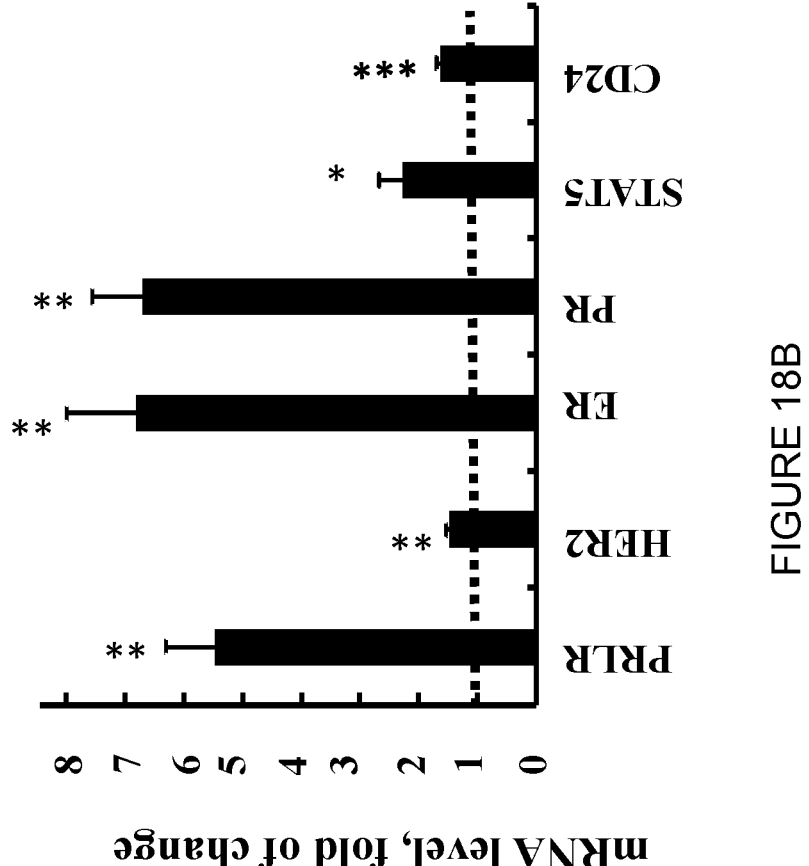
FIG. 18B shows mRNA levels of the indicated genes which were analyzed in si-hVDAC1-TTs and are presented relative to the levels in si-NT-TTs as fold change. Results are means±SEM (n=3); p*≤0.05; p≤0.01; p*≤0.001. Dashed line indicates the control level.

CD44$^+$/CD24$^-$ breast cancer cells possess stem/progenitor cell properties. CD44, a receptor of hyaluronan and other ligands, such as collagen types I and IV, as well as metalloproteinases of the extracellular matrix, are highly expressed in such cells. At the same time, the absence or low expression of CD24 by these cells was detected. The present invention now shows that in si-hVDAC1-TTs, the levels of CD44 were down-regulated and those of CD24 were up-regulated, when evaluated by immunofluorescence (IF) (FIG. 18A). IF staining of Her2 showed increased expression levels in si-hVDAC1-TTs, relative to the expression noted in NT-TTs (FIG. 18A). Furthermore, the expression levels of prolactin, estrogen and progesterone receptors (PRLR, ER, PR), and of Her2, CD24 and STATS, associated with prolactin receptor activity, were all increased in si-hV-DAC1-TTs, as analyzed by q-RT-PCR (FIG. 18B). These results show that silencing the expression of VDAC1 can reverse the characterization of MBA-MA-231 breast cancer cells from triple-negative to cells amenable to treatment with anti-cancer drugs having affinity to at least one of the estrogen receptor, progesterone receptor and ERBB2/Her2 receptor.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

---

The invention claimed is:

1. A VDAC1-silencing RNA interference (RNAi) molecule comprising:
   a. a first oligonucleotide comprising the nucleic acid sequence as set forth in SEQ ID NO:1 derivatized by 2'-O-methyl (2'-O-Me) at positions 14, 4, and 17, and not 2'-O-Me derivatized at positions 2, 6, 9, 15, and 20 of SEQ ID NO: 1, and
   b. a second oligonucleotide comprising the nucleic acid sequence as set forth in SEQ ID NO: 2 derivatized by 2'-O-Me at positions 7 and 13, and not 2'-O-Me derivatized at positions 2 and 20 of SEQ ID NO:2.

2. The VDAC1-silencing RNA interference (RNAi) molecule of claim 1, wherein the first and/or the second oligonucleotide further comprises a 3' overhang of 1-5 nucleotides.

3. The VDAC1-silencing RNA interference (RNAi) molecule of claim 2, wherein said oligonucleotide is an siRNA comprising a first oligonucleotide having the sequence as set forth in SEQ ID NO:5 and a second oligonucleotide having the sequence as set forth in SEQ ID NO:6.

* * * * *